(12) United States Patent
Fukushima et al.

(10) Patent No.: US 7,696,325 B2
(45) Date of Patent: Apr. 13, 2010

(54) POLYPEPTIDE INDUCING APOPTOSIS

(75) Inventors: Naoshi Fukushima, Gotemba (JP); Masayuki Tsuchiya, Gotemba (JP); Masayoshi Oh-Eda, Gotemba (JP); Shinsuke Uno, Gotemba (JP); Yasufumi Kikuchi, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1225 days.

(21) Appl. No.: 10/221,131

(22) PCT Filed: Mar. 12, 2001

(86) PCT No.: PCT/JP01/01912

§ 371 (c)(1), (2), (4) Date: Oct. 2, 2002

(87) PCT Pub. No.: WO01/66737

PCT Pub. Date: Sep. 13, 2001

(65) Prior Publication Data

US 2004/0073013 A1    Apr. 15, 2004

Related U.S. Application Data

(63) Continuation-in-part of application No. 09/523,095, filed on Mar. 10, 2000, now abandoned.

(30) Foreign Application Priority Data

Apr. 17, 2000 (JP) ............................... 2000-115246
Oct. 20, 2000 (JP) ............................... 2000-321822

(51) Int. Cl.
*C07K 16/00* (2006.01)
(52) U.S. Cl. .................... 530/387.7; 530/388.1
(58) Field of Classification Search ........................ None
See application file for complete search history.

(56) References Cited

U.S. PATENT DOCUMENTS

| | | | |
|---|---|---|---|
| 4,946,778 A | 8/1990 | Ladner et al. | |
| 5,618,920 A * | 4/1997 | Robinson et al. | 530/387.1 |
| 5,837,242 A | 11/1998 | Holliger et al. | |
| 5,837,821 A | 11/1998 | Wu | |
| 5,840,344 A | 11/1998 | Fukushima | |
| 5,877,291 A | 3/1999 | Mezes et al. | |
| 5,885,574 A | 3/1999 | Elliott | |
| 5,977,322 A | 11/1999 | Marks et al. | |
| 6,126,980 A | 10/2000 | Smith et al. | |
| 6,183,744 B1 | 2/2001 | Goldenberg | |
| 6,323,000 B2 | 11/2001 | Briggs et al. | |
| 6,342,220 B1 | 1/2002 | Adams et al. | |
| 6,368,596 B1 | 4/2002 | Ghetie et al. | |
| 6,579,692 B1 | 6/2003 | Fukushima | |
| 6,683,157 B2 | 1/2004 | Briggs et al. | |
| 6,699,686 B1 | 3/2004 | Brocard et al. | |
| 6,719,972 B1 | 4/2004 | Gribben et al. | |
| 6,759,043 B2 | 7/2004 | Fukushima | |
| 7,262,278 B2 | 8/2007 | Tawara et al. | |
| 2001/0006796 A1 | 7/2001 | Briggs et al. | |
| 2002/0028178 A1 | 3/2002 | Hanna et al. | |
| 2002/0193571 A1 | 12/2002 | Carter et al. | |
| 2002/0197706 A1 | 12/2002 | Nadkarni et al. | |
| 2003/0073161 A1 | 4/2003 | Briggs et al. | |
| 2003/0082612 A1 | 5/2003 | Snodgrass et al. | |
| 2003/0147894 A1 | 8/2003 | Fukushima | |
| 2003/0148409 A1 | 8/2003 | Rossi et al. | |
| 2003/0157100 A1 | 8/2003 | Fukushima et al. | |
| 2003/0157577 A1 | 8/2003 | Fukushima et al. | |
| 2003/0202975 A1 | 10/2003 | Tedder | |
| 2003/0211108 A1 | 11/2003 | Fukushima et al. | |
| 2004/0001828 A1 | 1/2004 | Tuscano | |
| 2004/0058393 A1 | 3/2004 | Fukishima et al. | |
| 2004/0073013 A1 | 4/2004 | Fukushima et al. | |
| 2004/0091475 A1 | 5/2004 | Tsuchiya et al. | |
| 2004/0242847 A1 | 12/2004 | Fukushima et al. | |
| 2005/0130224 A1 | 6/2005 | Saito et al. | |
| 2006/0222643 A1 | 10/2006 | Tsunoda et al. | |
| 2006/0275301 A1 | 12/2006 | Ozaki et al. | |
| 2007/0003556 A1 | 1/2007 | Tsuchiya et al. | |
| 2007/0280951 A1 | 12/2007 | Kimura et al. | |

(Continued)

FOREIGN PATENT DOCUMENTS

AU           755822          3/1999

(Continued)

OTHER PUBLICATIONS

Vernon-Wilson et al, Eur J Immunol 20:2130-2137, 2000 ).*

(Continued)

*Primary Examiner*—Misook Yu
*Assistant Examiner*—Mark Halvorson
(74) *Attorney, Agent, or Firm*—Foley & Lardner LLP

(57) ABSTRACT

This invention relates to reconstructed polypeptides which have properties of inducing apoptosis of nucleated blood cells having Integrin Associated Protein (IAP) and causing no hemagglutination. The reconstructed polypeptides comprise two or more H chain V regions and two or more L chain V regions of a monoclonal antibody which induces apoptosis of nucleated blood cells having IAP. The reconstructed polypeptides are useful as a therapeutic agent for blood dyscrasia such as leukemia.

19 Claims, 38 Drawing Sheets

U.S. PATENT DOCUMENTS

| | | | |
|---|---|---|---|
| 2007/0281327 | A1 | 12/2007 | Nakano et al. |
| 2008/0009038 | A1 | 1/2008 | Ohtomo et al. |
| 2008/0206229 | A1 | 8/2008 | Ono et al. |
| 2008/0274110 | A1 | 11/2008 | Ozaki et al. |
| 2009/0022687 | A1 | 1/2009 | Matsumoto et al. |
| 2009/0028854 | A1 | 1/2009 | Igawa et al. |
| 2009/0117097 | A1 | 5/2009 | Igawa et al. |

FOREIGN PATENT DOCUMENTS

| | | | |
|---|---|---|---|
| EP | 0 721 015 A1 | | 7/1996 |
| EP | 0 903 149 | | 3/1999 |
| EP | 903149 A1 | | 3/1999 |
| EP | 1 035 132 | | 9/2000 |
| EP | 1 327 680 | | 7/2003 |
| EP | 1 369 431 | | 12/2003 |
| EP | 1 396 500 | | 3/2004 |
| EP | 1 561 759 | | 8/2005 |
| EP | 1 712 565 | | 10/2006 |
| EP | 1 757 686 A1 | | 2/2007 |
| EP | 1 262 548 B1 | | 10/2008 |
| JP | 7503622 | | 4/1995 |
| JP | 7236475 | | 9/1995 |
| JP | 97/32601 A1 | | 9/1997 |
| JP | 10-505231 | | 5/1998 |
| JP | 11-500916 | | 1/1999 |
| JP | 11-092500 | | 4/1999 |
| JP | 2001-506135 | | 5/2001 |
| JP | 2001-513999 | | 9/2001 |
| JP | 2001-518930 | | 10/2001 |
| JP | 2002-544173 | | 12/2002 |
| JP | 2004-086862 | | 3/2004 |
| MX | 9905856 | | 7/2000 |
| WO | WO 91/16928 | | 11/1991 |
| WO | WO 92/19759 | | 11/1992 |
| WO | WO 96/04925 | | 2/1996 |
| WO | WO 96/26648 | | 9/1996 |
| WO | WO 96/36360 A | | 11/1996 |
| WO | WO 97/01633 | | 1/1997 |
| WO | WO 97/31108 | | 8/1997 |
| WO | WO 97/32601 A1 | | 9/1997 |
| WO | WO 98/28331 | | 7/1998 |
| WO | WO 98/41641 | | 9/1998 |
| WO | WO 98/42378 | | 10/1998 |
| WO | WO 98/44001 A1 | | 10/1998 |
| WO | WO 99/02567 | | 1/1999 |
| WO | WO 99/03495 A | | 1/1999 |
| WO | PCT/JP98/04118 | * | 3/1999 |
| WO | WO 99/10494 | | 3/1999 |
| WO | WO 99 12973 A1 | | 3/1999 |
| WO | WO 99/17364 | | 4/1999 |
| WO | WO 00/23593 | | 4/2000 |
| WO | WO 00 53634 A1 | | 9/2000 |
| WO | WO 00/67795 | | 11/2000 |
| WO | WO 00/75191 | | 12/2000 |
| WO | WO 01/64713 | | 9/2001 |
| WO | WO 01/66737 | | 9/2001 |
| WO | WO 01/74388 | | 10/2001 |
| WO | WO 01/77342 | | 10/2001 |
| WO | WO 01/79494 | | 10/2001 |
| WO | WO 01/87337 | | 11/2001 |
| WO | WO 01/97858 | | 12/2001 |
| WO | WO 02/04021 | | 1/2002 |
| WO | WO 02/22212 | | 3/2002 |
| WO | WO 02/33072 | | 4/2002 |
| WO | WO 02/33073 | | 4/2002 |
| WO | WO 02/078612 A | | 10/2002 |
| WO | WO 02/094880 | | 11/2002 |
| WO | WO 02/097033 | | 12/2002 |
| WO | WO 03/033654 | | 4/2003 |
| WO | WO 03/104425 | | 12/2003 |
| WO | WO 03/107218 | | 12/2003 |
| WO | WO 2004/033499 | | 4/2004 |
| WO | WO 2004/087763 | | 10/2004 |
| WO | WO 2005/056602 | | 6/2005 |
| WO | WO 2005/056603 | | 6/2005 |
| WO | WO 2005/056604 | | 6/2005 |
| WO | WO 2005/056605 | | 6/2005 |
| WO | WO 2005/056798 | | 6/2005 |
| WO | WO 2005/100560 | | 10/2005 |

OTHER PUBLICATIONS

Brooke et al, J Immunol 173:2562-2570, 2004.*
Mateo et al, Nature Medicine 5:1277-84 1999.*
Kikuchi et al, Biochem Biophys Res Comm 315:912-918, 2004.*
Goel et al Cancer Res 60:6964-6971, 2000.*
Mateo, V. et al., "CD47 Ligation Induces Caspase-Independent Cell Death in Chronic Lymphocytic Leukemia", *Nature Medicine*, 5(11):1277-1284, Nov. 1999.
Peterson, R.D., et al., "CD47 Signals T Cell Death", *J. Immunol.*, 162(12):7031-7040, Jun. 15, 1999.
Lindberg et al., "Molecular Cloning of Integrin-Associated Protein: An Immunoglobulin Family Member with Multiple Membrane-Spanning Domains Implicated in $\alpha_v\beta_3$-Dependent Ligand Binding," The Journal of Cell Biology, vol. 123, No. 2, The Rockefeller University Press, Oct. 1993, pp. 485-496.
Mateo et al., "Induction of Apoptosis in B-Cells From Chronic Lymphocytic Leukemia (B-CLLs) by CD47," FASEB Journal, vol. 12, No. 5, Mar. 20, 1998, p. A1082.
Fukushima et al., "Apoptosis of Bone Marrow Cells Via Integrin Associated Protein by the Novel Monoclonal Antibody," Blood, vol. 94, No. 10, Nov. 15, 1999, p. 479A.
Bartley, T., et al., "Identification and Cloning of a Megakaryocyte Growth and Development Factor That is a Ligand for the Cytokine Receptor Mpl," Cell, vol. 77, pp. 1117-1124 (1994).
Bazil, V. et al., "Apoptosis of Human Hematopoietic Progenitor Cells Induced by Crosslinking of Surface CD43, the Major Sialoglycoprotein of Leukocytes," pp. 502-511 (1995).
Bazzoni et al., "Chimeric tumor necrosis factor receprors with constitutive signaling activity," *Proc. Natl. Acad. Sci. USA* (Jun. 6, 1995), vol. 92, No. 12, pp. 5376-5580.
Berger, S. L., et al., "Inhibition of Intractable Nucleases with Ribonucleoside-Vanadyl Complexes: Isolation of Messenger Ribonucleic Acid From Resting Lymphocytes", *Biochemistry*, vol. 18, No. 23, pp. 5143-5149 (1979).
Burthem, et al., "Hairy Cell Interactions with Extracellular Matrix: Expression of Specific Integrin Receptors and Their Role in the Cell's Response to Specific Adhesive Proteins," Blood, vol. 84, No. 3, pp. 873-882 (1994).
Caldas, C., et al., Mol. Immunol., vol. 39. No. 15, pp. 941-952 (2003).
Chien, N. C., et al., Proc. Natl. Acad. Sci. USA, vol. 84, No. 14, pp. 5532-5536 (1989).
Chirgwin, J. M., et al., "Isolation of Biologically Active Ribonucleic Acid from Sources Enriched in Ribonuclease", *Biochemistry*, vol. 18, No. 24, pp. 5294-5299 (1979).
Cooper, D., et al., "Transendothelial migration of neutrophils involves integrin-associated protein (CD47)," Proc. Natl. Acad. Sci. USA, pp. 3978-3982 (1995).
de Sauvage, F., et al., "Stimulation of Megakaryocytopoiesis and Thrombopoiesis by the c-Mpl Ligand," Nature, vol. 369, pp. 533-538 (1994).
de St. Groth, S. F., et al., "Production of Monoclonal Antibodies: Strategy and Tactics," Journal of Immunological Methods, vol. 35, pp. 1-21 (1980).
Deng, B., et al., "An Agonist Murine Monoclonal Antibody to the Human c-Mpl Receptor Stimulates Megakaryocytopoiesis," Blood, vol. 92, No. 6, pp. 1981-1988 (1991).
Felgenhauer, M., et al., "Nucleotide Sequences of the cDNAs Encoding the V-Regions of H- and L-Chains of a Human Monoclonal Antibody Specific to HIV-1 —gp41," Nucleic Acids Research, vol. 18, No. 16, p. 4927 (1990).
Fujimoto, T., et al., Blood, vol. 86, No. 6, pp. 2174-2182 (1995).

Fukushima, N., et al., "Enhanced Hematopoiesis In Vivo and In Vitro by Splenic Stromal Cells Derived From the Mouse With Recombinant Granulocyte Colony-Stimulating Factor", Blood. vol. 80, No. 8, pp. 1914-1922 (1992).

Galfre, G., et al., "Preparation of Monoclonal Antibodies: Strategies and Procedures," Methods in Enzymology, vol. 73, pp. 3-46 (1981).

Galfre, G., et al., "Rat x rat hybrid myelomas and a monoclonal anti-Fd portion of mouse IgG," Nature, vol. 277, pp. 131-133 (1979).

Genestier, L., et al., "Antibodies to HLA Class I α 1 Domain Trigger Apoptosis of CD 40-Activated Human B Lymphocytes," Blood, vol. 90, No. 2, pp. 726-735 (1997).

Giusti, A. M., et al., Proc. Natl. Acad. Sci. USA, vol. 84, No. 9, pp. 2926-2930 (1987).

Goding, Monoclonal Antibodies: Principles and Practice, Academic Press, second Ed, pp. 125-129 (1986).

Grell, M., et al., "TR50 and TR80 Tumor Necrosis Factor (TNF)-Receptors Can Independently Mediate Cytolysis", Lymphokine and Cytokine Research, vol. 12, No. 3, pp. 143-148 (Jun. 1993).

Gussow, D., et al., Methods in Enzymology, vol. 203, pp. 99-121 (1991).

Hopp, T., et al., "A Short Polypeptide Marker Sequence Useful for Recombinant Protein Identification and Purification," Bio/Technology, vol. 6, pp. 1204-1210 (1988).

Hudson, P. J., et al., "High avidity scFv multimers; diabodies and triabodies" J. Immunol. Methods, Elsevier Science Publishers, vol. 231, No. 1-2, pp. 177-189 (1999).

Huston, J., et al., "Protein Engineering of Antibody Binding Sites: Recovery of Specific Activity in an Anti-Digoxin Single-Chain Fv Analogue Produced in *Escherichia coli*," Proc. Natl. Acad. Sci. USA, vol. 85, pp. 5879-5883 (1988).

Itoh, N., et al., "The Polypeptide Encoded by the cDNA for Human Cell Surface Antigen Fas Can Mediate Apoptosis," Cell, vol. 66, pp. 233-243 (1991).

Kearney, J. F., et al., "A New Mouse Myeloma Cell Line That Has Lost Immunoglobulin Expression But Permits The Construction of Antibody-Secreting Hybrid Cells Lines," The Journal of Immunology, vol. 123, No. 4, pp. 1548-1550 (1979).

Kipriyanov, S., et al., "Bispecific CD3 X CD19 Diabody for T Cell-Mediated Lysis of Malignant Human B Cells," Int. J. Cancer, vol. 77, pp. 763-772 (1988).

Kohler, G., et al., "Derivation of specific antibody-producing tissue culture and tumor lines by cell fusion," Eur. J. Immunol., vol. 6, pp. 511-519 (1976).

Larrick, J. W., et al., "Polymerase Chain Reaction Using Mixed Primers: Cloning of Human Monoclonal Antibody Variable Region Genes From Single Hybridoma Cells", Bio/Technology, vol. 7, pp. 934-938 (1989.

Law, L. W., et al., "Observations On the Effect Of A Folic-Acid Anatagonist On Transplantable Lymphoid Leukemias In Mice", Journal of the National Cancer Institute, vol. 10, pp. 179-193 (1949).

Lei, S. et al., "Characterization of the *Erwinia carotovora pelB* Gene and Its Product Pectate Lyase," J. Bacteriol., pp. 4379-4383 (1987).

Lindberg, et al., "Rh-Related Antigen CD47 is the Signal-Transducer Integrin-Associated Protein," J. Biol. Chem., vol. 269, pp. 1567-1570(1994).

Margulies, D. H., et al., "Somatic Cell Hybridization of Mouse Myeloma Cells," Cell, vol. 8, pp. 405-415 (1976).

Mariuzza, R. A., et al., Annu. Rev. Biophys. Biophys. Chem., vol. 16, pp. 139-159(1987).

Mawby, W. J., et al., "Isolation and characterization of CD47 glycoprotein: a multispanning membrane protein which is the same as integrin-associated protein (IAP) and the ovarian tumor marker OA3," Biochem. J., vol. 304, pp. 525-530 (1994).

Methia, N., et al., "Oligodeoxynucleotides Antisense to the Proto-Oncogene *c-Mpl* Specifically Inhibit In Vitro Megakaryocytopoiesis," Blood, vol. 82, No. 5, pp. 1395-1401 (1993).

Milili, M., et al., "The VDJ Repertoire Expressed in Human preB Cells Reflects the Selection of *Bona Fide* Heavy Chains," Eur. J. Immunol. vol. 26, pp. 63-69 (1996).

Nakayama, et al., J. Mole. Med., vol. 83, pp. 316-320 (2005).

O'Brien et al., "Monoclonal antibodies for the human insulin receptor stimulate intrinsic receptor-kinase activity," *Biochim. Soc. Trans.* (1986), vol. 14, No. 6, pp. 1021-1023.

Paul, Fundamental Immunology, Raven Press, NY, Chapter 8, p. 242 (1993).

Petterson, "CD47 and death signaling in the immune system," Apoptosis vol. 5, pp. 299-306 (2000).

Riechmann, L., et al., "Reshaping Human Antibodies for Therapy", Nature, vol. 332, pp. 323-327 (1988).

Roue, G., et al., Biochimie, vol. 85, pp. 741-746 (2003).

Rozsnyay et al., "Phenylarsine oxide (PAO) blocks antigen receptor-induced calcium response and tyrosine phosphroylation of a distinct group of proteins," *Immunology Lett.* (Aug. 1993), vol. 37, Nos. 2-3, pp. 197-205.

Rudikoff, et al., Proc. Natl. Acad. Sci. USA vol. 79, p. 1979 (1982).

Schickel, et al., "Gene for Integrin-Associated Protein (IAP, CD47): Physical Mapping, Genomic Structure, and Expression Studies in Skeletal Muscle," Biochem. Cell. Biol., vol. 80, No. 2, pp. 169-176 (2002).

Schwartz, M. A., et al., "A 50-kDa Integrin-associated Protein Is Required for Integrin-regulated Calcium Entry in endothelial Cells," J. Biol. Chem., vol. 268, No. 27, pp. 19931-19934 (1993).

Shigeta, M., et al., "Sperm-immobilizing monoclonal antibody to human seminal plasma antigens," Clin. Exp. Immunol., vol. 42, pp. 458-462 (1980).

Shulman, M., et al., "A better cell line for making hybridomas secreting specific antibodies," Nature, vol. 276, pp. 269-270 (1978).

Skolnick, et al., "From Genes to Protein Structure and Function: Novel Applications of Computational Approaches in the Genomic Era," Trends in Biotechnology, vol. 18, pp. 34-39 (2000).

Souyri, M., et al., "A Putative Truncated Cytokine Receptor Gene Transduced by the Myeloproliferative Leukemia Virus Immortalizes Hematopoietic Progenitors," Cell, vol. 63, Dec. 21, pp. 1137-1147 (1990).

Spaargaren, M., et al., "Antibody-induced Dimerization Activates the Epidermal Growth Factor Receptor Tyrosine Kinase", The J. Biol. Chem., vol. 266. No. 3, pp. 1733-1739 (1981).

Trowbridge, I. S., "Interspecies Spleen-Myeloma Hybrid Producing Monoclonal Antibodies Against Mouse Lymphocyte Surface Glycoprotein, T200," J. Exp. Med., vol. 148, pp. 313-323 (1978).

Xie, et al, "Direct demonstration of MuSK involvement in acetylcholine receptor clustering through identification of agonist ScFv," Nature Biotechnology, vol. 15, pp. 768-771 (1997).

Yanabu et al., "Tyrosine phosphorylation and p72syk activation by an anti-glycoprotein lb monoclonal antibody," *Blood* (1997), vol. 89, No. 5, pp. 1590-1598.

Yarden et al., "Self-phosphorylation of epidermal growth factor receptor: evidence for a model of intermolecular allosteric activisation," *Biochemistry* (1987), vol. 26, No. 5, pp. 1434-1442.

Yelton, D. E., et al., "Fusion of Mouse Myeloma and Spleen Cells," Current Topics in Microbiology and Immunology, vol. 81, pp. 1-7 (1978).

Brown et al., "Integrin-associated protein (CD47) and its ligands," TRENDS in Cell Biology, Mar. 2001, 11(3), 130-135.

Deng et al., "An Agonist Murine Monoclonal Antibody to the Human c-Mpl Receptor Stimulates Magakaryocytopoiesis," Blood, Sep. 15, 1998, 92(6), 1981-1988.

Dillman, Robert O., "Monoclonal Antibodies for Treating Cancer," Annals of Internal Medicine, Oct. 1, 1989, 11(7), 592-603.

Horan et al., "Dimerization of the Extracellular Domain of Granulocyte-Colony Stimulating Factor Receptor by Ligand Binding: A Monovalent Ligand Induces 2:2 Complexes," Biochemistry, 1996, 35, 4886-4896.

Greenspan et al., "Defining epitopes: It's not as easy as it seems," Nature Biotechnology, vol. 17, Oct. 1999, pp. 936-937.

Desplancq et al., "Multimerization behaviour of single chain Fv variants for the tumour-binding antibody B72.3," Protein Eng., Aug. 1994, vol. 7, No. 8, pp. 1027-1033 (Abstract).

Dorai et al., "Mammalian cell expression of signle-chain Fv (sFv) antibody proteins and their C-terminal fusions with interleukin-2 and other effector domains," Biotechnology, Sep. 1994, vol. 12, No. 9, pp. 890-897 (Abstract).

Jiang et al., "A Novel Peptide Isolated from a Phage Display Peptide Library with Trastuzumab Can Mimic Antigen Epitope of HER-2," J. Biol. Chem., Feb. 11, 2005, vol. 280, No. 6, pp. 4656-4662.

Keen et al., "The use of serum-free medium for the production of functionally active humanized monoclonal antibody from NS0 mouse myeloma cells engineered using glutamine synthetase as a selectable marker," Cytotechnology, Jan. 1994, vol. 18, No. 3, pp. 207-217 (Abstract).

Kortt et al., "Recombinant anti-sialidase single-chain variable fragment antibody: Characterization, formation of dimmer and higher-molecular-mass multimers and the solution of the crystal structure of the single-chain variable fragment/sialidase complex," Eur. J. Biochem., 1994, vol. 221, pp. 151-157.

Kortt et al., "Single-chain Fv fragments of anti-neuraminidase antibody NC10 containing five- and ten-residue linkers form dimmers and with zero-residue linker a trimer," Protein Engineering, 1997, vol. 10, No. 4, pp. 423-433.

Reinhold et al., "In vivo expression of alternatively spliced forms of integrin-associated protein (CD47)," J. Cell Science, 1995, vol. 108, pp. 3419-3425.

Reiter et al., "Engineering interchain disulfide bonds into conserved framework regions of Fv fragments: improved biochemical characteristics of recombinant immunotoxins containing disulfide-stabilized Fv," Protein Engineering, 1994, vol. 7, No. 5, pp. 697-704.

Reiter et al., "Stabilization of the Fv Fragments in Recombinant Immunotoxins by Disulfide Bonds Engineered into Conserved Framework Regions," Biochemistry, 1994, vol. 33, pp. 5451-5459.

Stancovski et al., "Mechanistic aspects of the opposing effects of monoclonal antibodies to the ERBB2 receptor on tumor growth," Proc. Natl. Acad. Sci. USA, Oct. 1991, vol. 88, pp. 8691-8695.

Verma et al., "Antibody engineering: Comparison of bacterial, yeast, insect and mammalian expression systems," Journal of Immunological Methods, 1998, vol. 216, pp. 165-181.

Avent et al., "Monoclonal antibodies that recognize different membrane proteins that are deficient in $Rh_{null}$ human erythrocytes," Biochem. J., 1988, vol. 251, pp. 499-505.

Brown et al., "Integrin-associated Protein: A 50-kD Plasma Membrane Antigen Physically and Functionally Associated with Integrins," J. Cell Biology, Dec. 1990, vol. 111, No. 6, pt. 1, pp. 2785-2794.

Schmidt et al., "A bivalent single-chain antibody-toxin specific for ErbB-2 and the EFG receptor," Int. J. Cancer, 1996, 65(4):538-546.

Pettersen, R, et al., "CD47 Signals T Cell Death," *The Journal of Immunology*, Jun. 1999, vol. 162, No. 12, pp. 7031-7040.

Lindberg, F., et al., "Molecular Cloning of Integrin-Associated Protein: An Immunoglobulin Family Member with Multiple Membrane-Spanning Domains Implicated in $\alpha_v\beta_3$-Dependent Ligand Binding," *Journal of Cell Biology*, vol. 123, No. 2, Oct. 1993, pp. 485-496.

Reinhold, M., et al., "In Vivo Expression of Alternatively Spliced Forms of Integrin-Associated Protein (CD47)," *Journal of Cell Science*, vol. 108, 1995, pp. 3419-3425.

Holliger, P., et al., "Specific Killing of Lymphoma Cells by Cytotoxic T-Cells Mediated by a Bispecific Diabody," *Protein Engineering*, vol. 9, No. 3, 1996, pp. 299-305.

Jones, T., et al., "Rapid PCR-Cloning of Full-Length Mouse Immunoglobulin Variable Regions," *Bio/Technology*, vol. 9, Jan. 1991, pp. 88-89.

Sato, K., et al., "Reshaping a Human Antibody to Inhibit the Interleukin 6-Dependent Tumor Cell Growth," *Cancer Research*, vol. 53, Feb. 15, 1993, pp. 851-856.

Mulligan, R., et al., "Synthesis of Rabbit β-Globin in Cultured Monkey Kidney Cells Following Infection with a SV40 β-Globin Recombinant Genome," *Nature*, vol. 277, No. 5692, Jan. 11, 1979, pp. 108-114.

Mizushima, S., et al., "pEF-BOS, A Powerful Mammalian Expression Vector," *Nucleic Acids Research*, vol. 18, No. 17, 1990, p. 5322.

Kozak, M., "At Least Six Nucleotides Preceding the AUG Initiator Codon Enhance Translation in Mammalian Cells," *Journal of Molecular Biology*, vol. 196, 1987, pp. 947-950.

U.S. Appl. No. 10/530,696, Non-Final OA mailed Dec. 21, 2006, 11 pages.

U.S. Appl. No. 10/530,696, Final OA mailed Aug. 8, 2007, 11 pages.

U.S. Appl. No. 10/530,696, Non-Final OA mailed Feb. 5, 2008, 8 pages.

U.S. Appl. No. 10/530,696, Non-Final OA mailed Nov. 17, 2008, 13 pages.

U.S. Appl. No. 10/530,696, Final OA mailed Jun. 8, 2009, 7 pages.

U.S. Appl. No. 10/550,934, Non-Final OA mailed Jun. 12, 2008, 16 pages.

U.S. Appl. No. 10 550,934, Final OA mailed Mar. 16, 2009, 13 pages.

U.S. Appl. No. 10/551,504, Non-Final OA mailed Apr. 15, 2009, 20 pages.

U.S. Appl. No. 10/582,413, Non-Final OA mailed Mar. 31, 2008, 8 pages.

U.S. Appl. No. 10/582,413, Final OA mailed Jun. 25, 2009, 20 pages.

U.S. Appl. No. 10/582,304, Non-Final OA mailed Apr. 1, 2009, 20 pages.

U.S. Appl. No. 10/582,304, Non-Final OA mailed Sep. 15, 2009, 8 pages.

U.S. Appl. No. 11/547,747, Non-Final OA mailed Jun. 1, 2009, 33 pages.

U.S. Appl. No. 10/548,727, Non-Final OA mailed Aug. 3, 2007, 14 pages.

U.S. Appl. No. 10/548,727, Final OA mailed Apr. 29, 2008, 19 pages.

U.S. Appl. No 10/548,727, Non-Final OA mailed Jan. 28, 2009, 13 pages.

U.S. Appl. No. 10/399,518, Non-Final OA mailed Mar. 27, 2006, 32 pages.

U.S. Appl. No. 10/399,518, Final OA mailed Dec. 28, 2006, 22 pages.

U.S. 10/399,518, Final OA mailed Jun. 7, 2007, 11 pages.

U.S. Appl. No. 10/399,518, Non-Final OA mailed Jan. 31, 2008, 13 pages.

U.S. Appl. No. 10/399,518, Final OA mailed Aug. 4, 2008, 8 pages.

U.S. Appl. No. 10/399,518, Non-Final OA mailed Feb. 17, 2009, 11 pages.

U.S. Appl. No. 10/399,518, Final OA mailed Sep. 11, 2009, 23 pages.

Abe et al., "Surrogate thrombopoietin," Immunology Letters, 1998, 61:73-78.

Arndt et al., "Factors Influencing the Dimer to Monomer Transition of an Antibody Single-Chain Fv Fragment," Biochemistry, 1998, 37:12918-12926.

Ballmaier et al., "c-mpl mutations are the cause of congenital amegakaryocytic thrombocytopenia," Blood, 2001, 97:139-146.

Beresford et al., "Binding Characteristics and Tumor Targeting of a Covalently Linked Divalent CC49 Single-Chain Antibody," Int. J. Cancer, 1999, 81:911-917.

Bodmer et al,. "TRAIL Receptor-2 Signals Apoptosis Through FADD and Caspase-8," Nat. Cell. Biol., 2000, 2:241-243.

Boger et al., Bioorganic and Medicinal Chemistry, 2001, 9:557-562.

Bowie et al., "Deciphering the Message in Protein Sequences: Tolerance to Amino Acid Substitutions," Science, 1990, 247:1306-1310.

Brinkmann et al., "FTY720: targeting G-protein-couples receptors for sphingosine 1-phosphate in transplantation and autoimmunity," Curr. Opin. Immunol., 2002, 14:569-575.

Brown et al., "Integrin-associated protein (CD47) and its ligands," Trends Cell Biology, 2001, 11(3):130-135.

Bruenke et al., "A recombinant bispecific single-chain Fv antibody against HLA class II and FcγRIII (CD16) triggers effective lysis of lymphoma cells," Br. J. Maematol., 2004, 125:167-179.

Buchsbaum et al., "Antitumor Efficacy of Tra-8 Anti-DR5 Monoclolan Antibody Alone or in Combination with Chemotherapy and/or Radiation Therapy in a Human Breast Cancer Model," Clin. Cancer Res., 2003, 9:3731-3741.

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 1990, 111:2129-2138.

Burrone et al., "Stimulation of HLA-A,B,C by IFN-alpha. The derivation of Molt 4 variants and the differential expression of HLA-A,B,C subsets," the EMBO Journal, 1985, 4(11):2855-2860.

Cangemi et al,. "IFN-alpha mediates the up-regulation of HLA class I on melanoma cells without switching proteasome to immunoproteasome," International Immunology, 2005, 15(12):1415-1421.

Caplus Accession No. 2005:547624, 2 pages, 2008.

Caron et al. "Engineered Humanized Dimeric Forms of IgG are More Effective Antibodies," J. Exp. Med., 1992, 176:1191-1195.

Casset et al., "A peptide mimetic of an anti-CD4 monoclonal antibody by rational design," Biochemical and Biophysical Research•Communications, 2003, 307:198-205.

Chen et al., "Selection and analysis of an optimized anti-VEGF antibody: Crystal structure of an affinity-matured Fab in complex with antigen," Journal of Molecular Biology, 1999, 293:865-881.

Chuntharapai et al., "Isotype-Dependent Inhibition of Tumor Growth in Vivo by Monoclonal Antibodies to Death Receptor 4," J. Immunol., 2001, 166 4891-4898.

Clark, "CD22, a B Cell-Specific Receptor, Mediates Adhesion and Signal Transduction," J. Immunol., 1993, 150:4715-4718.

Co et al., "A humanized antibody specific for the platelet integrin gpIIb/IIIa," J. Immunol., 1994, 152:2968-2976.

Cochlovius et al., "Cure of Burkitt's Lymphoma in Severe Combined Immunodeficiency Mice by T Cells, Tetravalent CD3 x CD 19 Tandem Diabody and CD28 Costimulation," Cancer Res., 2000, 60:4336-4341.

Daniel et al., "Induction of Apoptosis in Human Lymphocytes by Human Anti-HLA Class I Antibodies," Transplantation, 2003, 75:1380-1386.

Daniel et al., "Pathway of apoptosis induced in Jurkat T Lymphoblasts by anti-HLA Class I antibotdies," Human Immunology, 2004, 65(3):189-199.

De Felice et al., "Differential regulatory role of monomorphic and polymorphic determinants of histocompatibility leukocyte antigen class I antigens in monoclonal antibody OKT3-induced T cell proliferation," J. Immunol., 1987, 139:2683-2689.

De Jonge et al., "In vivo retargeting of T cell effector function by recombinant bispecific single chain Fv (anti-DC3 x anti-idiottype) induces long term survival of the murine BCL1 lymphoma model," J. Immunol., 1998, 161(3):1454-1461.

De Leon et al., "High resolution human leukocyte antigen (HLA) class I and class II allele typing in Mexican mestizo women with sporadic breast cancer: case-control study," BMC Cancer, 2009, 9(48):1-9.

De Nardo et al., "Anti-HLA-DR/anti-DOTA Diabody Construction in a Modular Gene Design Platform: Bispecific Antibodies for Pretargeted Radioimmunotherapy," Cancer Biother. Radiopharm., 2001, 16:525-535.

De Pascalis et al., "Grafting of 'abbreviated' complementary-determining regions containing specificity-determining residues essentially for ligand contact to engineer a less immunogenic humanized monoclonal antibody," Journal of Immunology, 2002, 169:3076-3084.

Degli-Esposti et al., "Cloning and Characterization of TRAIL-R3, a Novel Member of the Emerging TRAIL Receptor Family," J. Exp. Med., 1997, 186:1165-1170.

Ebert et al., "Expression of Metallothionein II in Intestinal Metaplasia, Dysplasia, and Gastric Cancer," Cancer Res., 2000, 60:1995-2001.

Elliott et al., "Activation of the Erythropoietin (EPO) Receptor by Bivalent Anti-EPO Receptor Antibodies," J. Biol. Chem., 1996, 271:24691-24697.

Emery et al., "Osteoprotegrin is a Receptor for the Cytotoxic Ligand TRAIL," J. Biol. Chem., 1998, 273:14363-14367.

Fayen et al., "Negative signaling by anti-HLA class I antibodies is dependent upon two triggering events," Int. Immunol., 1998, 10:1347-1358.

Funaro et al., "Monoclonal antibodies and therapy of human cancers," Biotechnol. Adv., 2000, 18:385-401.

Genestier et al., "Caspase-dependent Ceramide Production in Fas- and HLA Class I-mediated Peripheral T Cell Apoptosis," J. Biol. Chem., 1998, 273:5060-5066.

Genestier et al., "Fas-Independent Apoptosis of Activated T Cells Induced by Antibodies to the HLA Class I α1 Domain," Blood, 1997, 90:3629-3639.

Genestier et al., "T cell sensitivity to HLA class I-mediated apoptosis is dependent on interleukin-2 and interleukin-4," Eur. J. Immunol., 1997, 27:495-499.

Ghetie et al., "Homodimerization of tumor-reactive monoclonal antibodies markedly increases their ability to induce growth arrest or apoptosis of tumor cells," PNAS USA, 1997, 94:7509-7514.

Goel et al. "$^{99m}$Tc-Labeled Divalent and Tetravalent CC49 Single-Chain Fv's: Novel Imaging Agents for Rapid in Vivo Localization of Human Colon Carcinoma," J. Nucl. Med., 2001, 42:1519-1527.

Goto et al., "A Novel Membrane Antigen Selectively Expressed on terminally Differentiated Human B Cells," Blood, 1994, 84:1992-1930.

Griffith et al., "Functional Analysis of TRAIL Receptors Using Monoclonal Antibodies," J. Immunol., 1999, 162:2597-2605.

Holliger et al., " 'Diabodies': Small bivalent and bispecific antibody fragments," PNAS USA, 1993, 90:6444-6448.

Holm et al., "Functional mapping and single chain construction of the anti-cytokeratin 8 monoclonal antibody TS1," Molecular Immunology, 2007, 44:1075-1084.

Hu et al., "Minibody: a Novel Engineerind Anti-Carcinoembryonic Antigen Antibody Fragment (Single-Chain Fv-CH3) which Exhibits Rapid, High-Level Targeting of Xenografts," Cancer Res., 1996, 56:3055-3061.

Kikuchi et al., "A bivalent single-chain Fv fragment against CD47 induces apoptosis for leukemic cells," Biochem. Biophys. Res. Commun., 2004, 315:912-918.

Kimura et al., "2D7 diabody bound to the α2 domain of HLA class I efficiently induces caspaseindependent cell death against malignant and activated lymphoid cells," Biochem. Biophys. Res. Commun., 2004, 325:1201-1209.

Kipriyanov et al., "Effect of Domain Order on the Activity of Bacterially Produced Bispecific Single-chain Fv Antibodies," J. Mol. Biol., 2003, 330:99-111.

Kong et al., J. Biol. Chem., 1993, 268:23055-23058.

Kortt et al., "Dimeric and trimeric antibodies: high avidity scFvs for cancer targeting," Biomol. Eng., 2001, 18:95-108.

Kreitman et al., "Cytotoxic Activity of Disulfide-stabilized Recombinant Immunotoxic RFB4(dsFv)- PE38 (BL22) toward Fresh Malignant Cells from Patients with B-cell Leukemias," Clin. Cancer Res., 2000, 6:1476-1487.

Kriangkum et al., "Bispecific and bifunctional single chain recombinant antibodies," Biomol. Eng., 2001, 18(2):31-40.

Kulkarni et al., "Programmed Cell Death Signaling Via Cell-surface Expression of a Single-chain Antibody Transgene," Transplantation, 2000, 69:1209-1217.

Kulkarni et al., "Construction of a Single-Chain Antibody Derived from 5H7, a Monoclonal Antibody Specific for a Death Signaling Domain of Human Class I Major Histocompatibility Complex," Transplant Proc., 1998, 30:1081.

Kumar et al., "The second PDZ domain of INAD is a type I domain involved in binding to eye proteinkinase C. Mutational analysis and naturally occurring variants," J. Biol. Chem., 2001, 276(27):24971-24977.

Lazar et al., "Transforming Growth Factor α: Mutation of Aspartic Acid 47 and Leucine 48 Results in Different Biological Activities," Molecular and Cellular Biology, Mar. 1988, 8(3):1247-1252.

Lebrun et al., "Antibodies to the Extraellular Receptor Domain Restore the Hormone-insensitive Kinase and Conformation of the Mutant Insulin Receptor Valine 382," J. Biol. Chem., 1993, 268:11272-11277.

Ledbetter et al., "Agonist activity of a CD40-specific single-chain Fv constructed from the variable regions of mAb G28-5," Critical Reviews in Immunology, 1997, 17:427-435.

Li et al., "The Epitope Specificity and Tissue Reactivity of Four Murine Monoclonal Anti-CD22 Antibodies," Cell. Immunol., 1989, 118:85-99.

Lin et al., "Structure-function relationships in glucagon: properties of highly purified des-His-1-monoiodo-, and (des-Asn-28, Thr-29)(homoserine lactone-27)-glucagon," Biochemistry, 1975, 14:1559-1563.

Mac Callum et al., "Antibody-antigen interactions: Contact analysis and binding site topography," Journal of Molecular Biology, 1996, 262:732-745.

Mack et al., "A small bispecific antibody construct expressed as a functional single-chain molecule with high tumor cell cytotoxicity," PNAS USA, 1995, 92(15):7021-7025.

Mallender et al., "Construction, expression and activity of a bivalent bispecific single-chain antibody," J. Biol. Chem., 1994, 269(1):199-206.

Marsters et al., "A Novel Receptor for Apo2L/TRAIL Contains a Truncated Death Domain," Curr. Biol., 1997, 7:1003-1006.

Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model.,"J. Exp. Med., 2003, 198:497-503.

Matsuoka et al., "A Novel Type of Cell Death of Lymphocytes Induced by a Monoclonal Antibody without Participation of Complement," J. Exp. Med., 1995, 181:2007-2015.

McInnes et al., "Cytokines in the pathogenesis of rheumatoid arthritis," Nature Reviews/Immunology, 2007, 7:429-442.

Milligan, Mol. Pharm., 2004, 66:1-7.

Moore et al., "Kinetics and thermodynamics of dimmer formation and dissociation for a recombinant humanized monoclonal antibody to vascular endothelial growth factor," Biochemistry, 1999, 38:13960-13967.

Mori et al., "Human normal hepatocytes are susceptible to apoptosis signal mediated by both TRAIL-R1 and TRAIL-R2," Cell Death and Differentiation, 2004, 11:203-207.

Ngo et al., "Computational Complexity, Protein Structure Prediction, and the Levinthal Paradox," the Protein Folding Problem and Tertiary Structure Prediction, Merz, Jr. et al., Editors, Birkhauser Boston, 1994:433-506.

Nishii, "CD22 antibody therapy," Current Therapy, 2001, 20:47-50, with English translation.

Ohtomo et al., "Molecular Cloning and Characterization of a Surface Antigen Preferentially Overexpressed on Multiple Myeloma Cells," Biochem. Biophys. Res. Commun., 1999, 258:583-591.

Ohtsuka et al., "Synergistic induction of tumor cell apoptosis by death receptor antibody and chemotherapy agent through JNK/p38 and mitochondrial death pathway," Oncogene, 2003, 22:2034-2044.

Oka, "Development of Novel Immunotoxin Using Recombinant Alpha-Sarcin and Its Application Treatment of Hematopoietic Tumor," Sankyo Seimei Kagaku Kenkyu Shinko Zaidan Kenkyu Hokokushu, 1998, 12:46-56, with concise English explanation.

Ono et al., "The humanized anti-NH1.24 antibody effectively kills multiple myeloma cells by human effector cell-mediated cytotoxicity," Mol. Immunol., 1999, 36:387-395.

Orita et al., "A novel therapeutic approache for thrombocytopenia by minibody agonist of the thrombopoietin receptor," Blood, 2006, 105:562-566.

Ozaki et al., "Humanized Anbi-HM1.24 Antibody Mediates Myeloma Cell Cytotoxicity that is Enhanced by Cytokine Stimulation of Effector Cells," Blood, 1999, 93:3922-3930.

Ozaki et al., A Recombinant HLA Class I-Specific Single Chain Fv Diabody Induces Cell Death in Human Lymphoid Malignancies, Blood, 2003, 102:933a, Abstract No. 3474.

Palacios et al., "IL-3-dependent mouse clones that express B-220 surface antigen, contain IG genes in germ-line configuration, and generate B lymphocytes in vivo," Cell, 1985, 41:727-734.

Pan et al. "The Receptor for the Cytotoxic Ligand TRAIL," Science, 1997, 276:111-113.

Pan et al., "An Antagonist Decoy Receptor and a Death Domain-Containing Receptor for TRAIL," Science, 1997, 277:815-818.

Paul, William E. Ed., Fundamental Immunology, 3$^{rd}$ Ed., 1993, 292-295.

Pettersen et al., "The TCR-Binding Region of the HLA Class I a2 Domain Signals Rapid Fas-Independent Cell Death: a Direct Pathway for T Cell-Mediated Killing of Target Cells?" J. Immunol., 1998, 160:4343-4352.

Pietri-Rouxel et al., Eur. J. Biochem., 1997, 247:1174-1179.

Pluckthun et al., "New protein engineering approaches to multivalent and bispecific antibody fragments," Immunotechnology, 1997, 3:83-105.

Reff et al., "A review of modifications to recombinant antibodies: attempt to increase efficacy in oncology applications," Critical Reviews in Oncology and Hematology, 2001, 40:25-35.

Rossi et al., "Development of New Multivalent-bispecific Agents for Pretargeting Tumor Localization and Therapy," Clin. Cancer Res., 2003, 9:3886s-3896s.

Rudikoff et al., "Single amino acid substitution altering antien-binding specificity," PNAS USA, 1982, 79:1979-1983.

Sal-Man et al., "Arginine mutations within a transmembrane domain of Tar, as Escherichia coli aspartate receptor, can drive monodimer dissociation and heterodimer association in vivo," Biochem. J., 2005, 385(1):29-36.

Sato et al., "CD22 is Both a Posotive and Negative Regulator of B Lymphocyte Antigen Receptor Signal Transduction: Altered Signaling in CD22-Deficient Mice," Immunity, 1996, 5:551-562.

Scheurle et al., "Cancer Gene Discovery Using digital Differential Display," Cancer Res., 2000, 60:4037-4043.

Schwartz et al., "A superactive insulin: [B10-aspartic acid]insulin(human)," PNAS USA, 1987, 84:6408-6411.

Scott, "The Problem with Potency," Nature Biotechnology, 2005, 23(9):1037-1039.

Sekimoto et al., "A Single-Chain Fv Diabody Against Human Leukocyte Antigen-A Molecules Specifically Induces Myeloma Cell Death in the Bone Marrow Environment," Cancer Res., 2007, 67(3):1184-1192.

Sekimoto et al., "Eradication of Human Myeloma Cells by a Recombinant HLA Class I-Specific Single Chain Fv Diabody," Blood, 102:932a, XP009106629 (Abstract #3469) (Nov. 2003) [Abstract of the American Society of Hematology 45$^{th}$ Annual Meeting, Dec. 6-9, 2003, San Diego, California].

Sheridan et al., "Control of Trail-Induced Apoptosis by a Family of Signaling and Decoy Receptors," Science, 1997, 277:818-821.

Skolnick et al., "From genes to protein structure and function: novel applications of computational approaches in the genomic era," Trends in Biotechnology, 2000, 18:34-39.

Smith et al., "Inhibition of T Cell Activation by a Monoclonal Antibody Reactive Against the α3 Domain of Human MHC Class I Molecules," J. Immunol., 1994, 153:1054-1067.

Stein et al., "Characterization of humanized IgG4 anti-HLA-DR monoclonal antibody that lacks effector cell functions but retains direct antilymphoma activity and increases the potency of rituximab," Blood, 2006. 108(8):2736-2744.

Tahtis et al., "Biodistribution Properties of 111Indium-labeled C-Functionalized trans-Cyclohexyl Diethylenetriaminepentaacetic Acid Humanized 3S193 Diabody and F9ab')2 Constructs in a Breats arcinoma Xenograft Model," Clin. Cancer Res., 2001, 7:1061-1072.

Tedder et al., "CD22; a B Lymphocyte-Specific Adhesion Molecule that Regulates Antigen Receptor Signaling," Annu. Rev. Immunol., 1997, 15:481-504.

Thilenius et al., "Agonist antibody and Fas ligand mediate different sensitivity to death in the signaling pathways of Fas and cytoplasmic mutants," Eur. J. Immunol., 1997, 27:1108-1114.

Vajdos et al. "Comprehensive functional maps of the antigen-binding site of an anti-ErbB2 antibody obtained with shotgun scanning mutagenesis," Journal of Molecular Biology, 2002, 320:415-428.

Van Geelen et al., "Differential modulation of the TRAIL receptors and the CD95 receptor in colon carcinoma cell lines," Br. J. Cancer, 2003, 89(2):363-373.

Walczak et al., "TRAIL-R2: a Novel Apoptosis-Mediating Receptor for TRAIL," EMBO J., 1997, 16:5386-5397.

Wells, "Perspectives in Biochemistry," Biochemistry, 1990, 29(37):8509-8517.

Whitlow et al., "Multivalent Fvs: characterization of single-chain Fv oligomers and preparation of a bispecific Fv," Protein Engineering, 1994, 7(8):1017-1026.

Wiley et al., "Identification and Characterization of a New Member of the TNF Family that Induces Apoptosis," Immunity, 1995, 3:673-682.

Winkler et al., "Changing the Antigen Binding Specificity by Single Point Mutations of an Anti-p24 (HIV-1) Antibody," J. Immunol., 2000, 265:4505-4514.

Woodle et al., "Anti-Human Class I a3 Domain-Specific Monoclonal Antibody Induces Programmed Cell Death in Murine Cells Expressing Human Class I MHC Transgenes," Transplant. Proc., 1998, 30:1059-1060.

Woodle et al., "Anti-Human Class I MHC Antibodies Induce Apoptosis by a Pathway that is Distinct from the Fas Antigen-Mediated Pathway," J. Immunol., 1997, 158:2156-2164.

Woodle et al., "Class I MHC Mediates Programmed Cell Death in Human Lymphoid Cells," Transplantation, 1997, 64:140-146.

Wu et al., "Humanization of a murine monoclonal antibody by simultaneous optimization of framework and CFR residues," Journal of Molecular Biology, 1999, 294:151-162.

Wu et al., "Tumor localization of anti-CEA single-chain Fvs: improved targeting by non-covalent dimmers," Immunotechnology, 1996, 2:21-36.

www.nlm.hih.gov/medlineplus/druginfo/medmaster/a682792.html, "Dexamethasone Oral," 4 pages, downloaded Jul. 19, 2007.

Xiong et al., "Efficient inhibition of human B-cell lymphoma xenografts with an anti-CD20 X anti-CD3 bispecific diabody," Cancer Lett., 2002, 177:29-39.

Xu et al., "Insight into hepatocellular carcinogenesis at transcriptome level by comparing gene expression profiles of hepatocellular carcinoma with those of corresponding noncancerous liver," PNAS USA, 2001, 98:15089-15094.

\* cited by examiner

SDS-PAGE analysis of MABL2-scFv

TSK gel G3000SW
20 mM Acetate buffer, 0.15 M NaCl, pH 6.0

Effect of MABL-2 (scFv) on serum hIgG
in KPMM2 i.v. SCID mice

Base Sequence and Amino Acid Sequence of Linker for HL Type

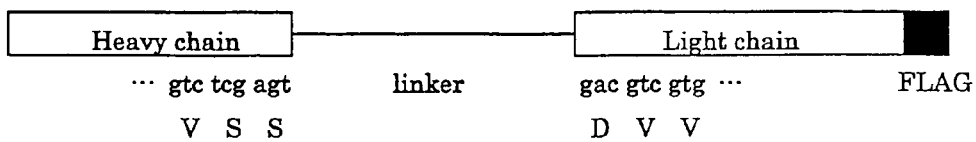

··· gtc tcg agt     linker     gac gtc gtg ···     FLAG
   V   S   S                   D   V   V

| Plasmid | Number of linker amino acid | linker | |
|---|---|---|---|
| CF2HL-0/pCOS1 | 0 | gtc tcg agt<br>V S S | gac gtc gtg<br>D V V |
| CF2HL-3/pCOS1 | 3 | gtc tcg agt ggt ggt tcc<br>V S S G G S | gac gtc gtg<br>D V V |
| CF2HL-4/pCOS1 | 4 | gtc tcg agt ggt ggt ggt tcc<br>V S S G G G S | gac gtc gtg<br>D V V |
| CF2HL-5/pCOS1 | 5 | gtc tcg agt ggt ggt ggt ggt tcc<br>V S S G G G G S | gac gtc gtg<br>D V V |
| CF2HL-6/pCOS1 | 6 | gtc tcg agt gt ggt ggt ggt ggt tcc<br>V S S G G G G G S | gac gtc gtg<br>D V V |
| CF2HL-7/pCOS1 | 7 | gtc tcg agt ggt ggt ggt ggt ggt ggt tcc gac gtc gtg<br>V S S G G G G G G S D V V | |

Fig. 38

Base Sequence and Amino Acid Sequence of Linker for HL Type

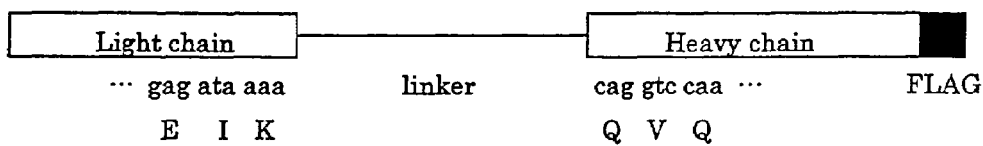

··· gag ata aaa     linker     cag gtc caa ···     FLAG
   E  I  K                      Q  V  Q

| Plasmid | Number of linker amino acid | linker | |
|---|---|---|---|
| CF2LH-0/pCOS1 | 0 | gag ata aaa<br>E  I  K | cag gtc caa<br>Q  V  Q |
| CF2LH-3/pCOS1 | 3 | gag ata aaa tcc gga ggc<br>E  I  K  S  G  G | cag gtc caa<br>Q  V  Q |
| CF2LH-4/pCOS1 | 4 | gag ata aaa tcc gga ggt ggc<br>E  I  K  S  G  G  G | cag gtc caa<br>Q  V  Q |
| CF2LH-5/pCOS1 | 5 | gag ata aaa tcc gga ggt ggt ggc<br>E  I  K  S  G  G  G  G | cag gtc caa<br>Q  V  Q |
| CF2LH-6/pCOS1 | 6 | gag ata aaa tcc gga ggt ggt ggt ggc<br>E  I  K  S  G  G  G  G  G | cag gtc caa<br>Q  V  Q |
| CF2LH-7/pCOS1 | 7 | gag ata aaa tcc gga ggt ggt ggt ggt ggc cag gtc caa<br>E  I  K  S  G  G  G  G  G  G  Q  V  Q | |

POLYPEPTIDE INDUCING APOPTOSIS

This application is a continuation-in-part of U.S. application Ser. No. 09/523,095, filed Mar. 10, 2000, now abandoned.

TECHNICAL FIELD

This invention relates to a reconstructed polypeptide with a property of inducing apoptosis of nucleated blood cells having Integrin Associated Protein (IAP) and causing no hemagglutination. More specifically, the present invention relates to the reconstructed polypeptide comprising two or more H chain V regions and two or more L chain V regions of a monoclonal antibody inducing apoptosis of nucleated blood cells having IAP. The reconstructed polypeptides are useful as a therapeutic agent for blood dyscrasia such as leukemia.

BACKGROUND ART

Japanese Patent Application 9-67499 discloses the preparation of a specific monoclonal antibody using a splenic stromal cell line as a sensitizing antigen aiming at developing specific antibodies that can recognize the aforementioned splenic stromal cells and the preparation of novel monoclonal antibodies that recognize mouse Integrin Associated Protein (mouse IAP) as an antigen. JP-Appl. 9-67499 also discloses that the monoclonal antibodies are capable of inducing apoptosis of myeloid cells.

WO99/12973 discloses monoclonal antibodies whose antigen is human Integrin Associated Protein (hereinafter referred to as human IAP; amino acid sequence and nucleotide sequence thereof are described in J. Cell Biol., 123, 485-496, 1993; see also Journal of Cell Science, 108, 3419-3425, 1995) and which are capable of inducing apoptosis of human nucleated blood cells (myeloid cell and lymphocyte) having said human IAP. These monoclonal antibodies are referred to antibody MABL-1 and antibody MABL-2, and hybridomas producing these antibodies are also referred to MABL-1 (FERM BP-6100) and MABL-2 (FERM BP-6101), respectively.

Japanese Patent Application 11-63557 describes the preparation of single-chain Fvs having single chain Fv regions from the monoclonal antibodies whose antigen is human IAP. The single-chain Fvs are capable of inducing apoptosis of nucleated blood cells having human IAP.

The monoclonal antibody recognizing IAP as an antigen induces apoptosis of nucleated blood cells having human IAP, but it also causes hemagglutination in vitro. It indicates that the administration of a large amount of the monoclonal antibody recognizing IAP as an antigen may result in a side effect such as hemagglutination.

DISCLOSURE OF INVENTION

An object of this invention is to provide reconstructed polypeptides with improved property of inducing apoptosis of nucleated blood cells having Integrin Associated Protein (IAP) and with decreased or completely eliminated property of causing hemagglutination. Another object of the present invention is to provide therapeutic agents for blood dyscrasia comprising the substance obtained above which induces apoptosis of nucleated blood cells having Integrin Associated Protein (IAP).

Therefore, the present invention relates to the reconstructed polypeptides which binds to Integrin Associated Protein (IAP), induces apoptosis of nucleated blood cells having IAP and causes no hemagglutination.

The invention relates also to the reconstructed polypeptides, reshaped antibodies.

The reshaped antibody may include any reconstructed polypeptide which comprises an L chain V region and an H chain V region derived from a monoclonal antibody, e.g. antibody MABL-1, antibody MABL-2 or the like inducing apoptosis of nucleated blood cells having IAP, preferably human IAP, which polypeptide induces apoptosis of nucleated blood cells having IAP, preferably human IAP and causes no hemagglutination. Further, the present invention also includes reconstructed polypeptides wherein an amino acid sequence of the V region is partially altered.

The present invention also relates to the humanization of the reconstructed polypeptide. The humanized reconstructed polypeptide comprises a humanized L chain V region and/or a humanized H chain V region. Specifically, the humanized polypeptide of the invention consists of the humanized L chain V region which comprises a framework region (FR) derived from an L chain V region of human monoclonal antibody and an CDR derived from an L chain V region of mouse monoclonal antibody and/or the humanized H chain V region which comprises an FR derived from an H chain V region of human monoclonal antibody and a CDR derived from an H chain V region of mouse monoclonal antibody. In this case, the amino acid sequence of FR or CDR may be partially altered, e.g. deleted, replaced or added.

Furthermore, the present invention relates to reconstructed polypeptides capable of inducing apoptosis of nucleated blood cells having human IAP, which polypeptides comprise an L chain C region of human antibodies and an L chain V region of the mouse monoclonal antibodies, and/or an H chain C region of human antibodies and an H chain V region of the mouse monoclonal antibodies.

The present invention also relates to reconstructed polypeptides inducing apoptosis of nucleated blood cells having human IAP, which polypeptides comprise a CDR derived from a monoclonal antibody of other mammals than mouse such as human, rat, bovine, sheep or the like, which corresponds to the aforementioned mouse CDR, or an L chain V region and an H chain V region which contain the aforementioned CDR. Such CDRs, L chain V regions and H chain V regions may include CDRs derived from a human monoclonal antibody prepared from, for example, a transgenic mouse or the like, and L chain V regions and H chain V regions derived from a human monoclonal antibody containing the aforementioned CDR.

The invention also relates to DNAs encoding the various reconstructed polypeptides as aforementioned and genetic engineering techniques for the production of recombinant vectors comprising the DNAs.

The invention also relates to host cells transformed with the recombinant vectors. Examples of host cells mammalian cells such as human cells, mouse cells or the like and microorganisms such as *E. coli, Bacillus subtilis*, yeast or the like.

The invention relates to a process for producing the reconstructed polypeptides, which comprises culturing the above hosts and extracting the reconstructed polypeptides from the culture thereof.

The present invention further relates to a process for producing a dimer of the single-chain Fv which comprises culturing host mammalian cells producing the single-chain Fv in a serum-free medium to secrete the single-chain Fv into the medium and isolating the dimer of the single-chain Fv formed in the medium.

The present invention relates to therapeutic agents for blood dyscrasia comprising as an active ingredient the reconstructed polypeptide obtained in the above which induces apoptosis of nucleated blood cells having Integrin Associated Protein (IAP). The therapeutic agents for blood dyscrasia of the invention are useful for the treatment of blood dyscrasia, for example, leukemia such as acute myeloid leukemia, chronic myelogenous leukemia, acute lymphoblastic leukemia, chronic lymphoblastic leukemia, adult T-cell leukemia, multiple myeloma, mixed leukemia and hairy cell leukemia, malignant lymphoma (Hodgkin's disease, non-Hodgkin's lymphoma), aplastic anemia, myelodysplasia syndrome and polycythemia vera.

The reconstructed polypeptides of the present invention preferably comprise two H chain V regions and two L chain V regions derived from the monoclonal antibodies. The structure of the reconstructed polypeptides may be a dimer of single-chain Fv comprising one H chain V region and one L chain V region or a polypeptide comprising two H chain V regions and two L chain V regions. In the reconstructed polypeptides of the invention, the H chain V region and the L chain V region are preferably linked through a peptide linker which consists of one or more amino acids. The resulting reconstructed polypeptides contain variable regions of the parent antibodies and retain the complementarity determining region (CDR) thereof, and therefore bind to the antigen with the same specificity as that of the parent monoclonal antibodies.

H Chain V Region

In the present invention, the H chain V region derived from the monoclonal antibody can be the H chain V region of the monoclonal antibody inducing apoptosis of nucleated blood cells having IAP or the H chain V region whose amino acid sequence is partially modified, preferably the H chain V region of the monoclonal antibody recognizing human IAP and inducing apoptosis of nucleated blood cells having IAP or the H chain V region whose amino acid sequence is partially modified. Preferable is the H chain V region derived from antibody MABL-1 or antibody MABL-2, or the H chain V region wherein the amino acid sequence of the H chain V region is partially modified. More preferable is humanized H chain V region comprising FR from an H chain V region of human monoclonal antibody and CDR from the H chain V region of mouse monoclonal antibody. The H chain V region further can be an H chain V region derived from a human monoclonal antibody corresponding to the aforementioned H chain V region of mouse monoclonal antibody, which can be produced by recombination technique. The H chain V region of the invention may be a fragment of aforementioned H chain V region, which fragment preserves the antigen binding capacity.

L Chain V Region

The L chain V region of the present invention can be L chain V region of the monoclonal antibody inducing apoptosis of nucleated blood cells having IAP or the L chain V region wherein the amino acid sequences of the L chain V region is partially modified, preferably the L chain V region of the monoclonal antibody recognizing human IAP and inducing apoptosis of nucleated blood cells having IAP or the L chain V region whose amino acid sequences is partially modified. Preferable is L chain V region derived from antibody MABL-1 or antibody MABL-2, or its L chain V region whose amino acid sequence is partially modified. More preferable is humanized L chain V region comprising FR from L chain V region of human monoclonal antibody and CDR from the L chain V region of mouse monoclonal antibody. The L chain V regions further can be an L chain V region derived from human monoclonal antibody corresponding to the aforementioned L chain V region of mouse monoclonal antibody, which can be produced by recombination technique. The L chain V regions of the invention may be fragments of L chain V region, which fragments preserve the antigen binding capacity.

Complementarity Determining Region (CDR)

Each V region of L chain and H chain forms an antigen-binding site. The variable region of the L and H chains is composed of comparatively conserved four common framework regions linked to three hypervariable regions or complementarity determining regions (CDR) (Kabat, E. A. et al., "Sequences of Protein of Immunological Interest", US Dept. Health and Human Services, 1983).

Major portions in the four framework regions (FRs) form β-sheet structures and thus three CDRs form a loop. CDRs may form a part of the β-sheet structure in certain cases. The three CDRs are held sterically close position to each other by FR, which contributes to the formation of the antigen-binding site together with three CDRs.

These CDRs can be identified by comparing the amino acid sequence of V region of the obtained antibody with known amino acid sequences of V regions of known antibodies according to the empirical rule in Kabat, E. A. et al., "Sequences of Protein of Immunological Interest".

Single-Chain Fv

A single-chain Fv is a polypeptide monomer comprising an H chain V region and an L chain V region linked each other which are derived from monoclonal antibodies. The resulting single-chain Fvs contain variable regions of the parent monoclonal antibodies and preserve the complementarity determining region thereof, and therefore the single-chain Fvs bind to the antigen by the same specificity as that of the parent monoclonal antibodies (JP-Appl. 11-63557). A part of the variable region and/or CDR of the single-chain Fv of the invention or a part of the amino acid sequence thereof may be partially altered, for example deleted, replaced or added. The H chain V region and L chain V region composing the single-chain Fv of the invention are mentioned before and may be linked directly or through a linker, preferably a peptide linker. The constitution of the single-chain Fv may be [H chain V region]-[L chain V region] or [L chain V region]-[H chain V region]. In the present invention, the single-chain Fv can form a dimer, trimer or which can be tetramer included in the reconstructed polypeptide of the invention.

Single-Chain Reconstructed Polypeptide

The single-chain reconstructed polypeptides of the present invention comprising two or more H chain V regions and two or more L chain V regions comprise two or more H chain V regions and L chain V regions as mentioned above. Each region of the peptide should be arranged such that the reconstructed single chain polypeptide forms a specific steric structure, concretely mimicking a steric structure formed by the dimer of single-chain Fv. For instance, the V regions are arranged in the order of the following manner:

[H chain V region]-[L chain V region]-[H chain V region]-[L chain V region]; or

[L chain V region]-[H chain V region]-[L chain V region]-[H chain V region], wherein these regions are connected through a peptide linker, respectively.

Linker

In this invention, the linkers for the connection between the H chain V region and the L chain V region may be any peptide linker which can be introduced by the genetic engineering procedure or any linker chemically synthesized. For instance, linkers disclosed in literatures, e.g. Protein Engineering, 9(3), 299-305, 1996 may be used in the invention. Examples of the peptide linkers may include, for example;

```
Ser

Gly-Ser

Gly-Gly-Ser

Ser-Gly-Gly

Gly-Gly-Gly-Ser (SEQ ID NO: 80)

Ser-Gly-Gly-Gly (SEQ ID NO: 81)

Gly-Gly-Gly-Gly-Ser (SEQ ID NO: 82)

Ser-Gly-Gly-Gly-Gly (SEQ ID NO: 83)

Gly-Gly-Gly-Gly-Gly-Ser (SEQ ID NO: 84)

Ser-Gly-Gly-Gly-Gly-Gly (SEQ ID NO: 85)

Gly-Gly-Gly-Gly-Gly-Gly-Ser (SEQ ID NO: 86)

Ser-Gly-Gly-Gly-Gly-Gly-Gly (SEQ ID NO: 87)

(Gly-Gly-Gly-Gly-Ser)$_n$ (SEQ ID NO: 88) and (Ser-Gly-Gly-Gly-Gly)$_n$ (SEQ ID NO: 89)
``` wherein n is an integer not less than one. Length of the peptide linker is in the range of 1 to 15 amino acids, preferably 2 to 12 amino acids, more preferably 3 to 10 amino acids. Procedures for introducing these linkers are mentioned in Explanation of DNA encoding the reconstructed polypeptide or the invention.

The chemically synthesized linkers, i.e. the chemical crosslinking agents, according to the invention can be any linkers conventionally employed for the linkage of peptides. Examples of the linkers may include N-hydroxy succineimide (NHS), disuccinimidyl suberate (DSS), bis(sulfosuccinimidyl)suberate (BS$^3$), dithiobis(succinimidyl propionate) (DSP), dithiobis(sulfosuccinimidyl propionate) (DTSSP), ethylene glycolbis(succinimidyl succinate) (EGS), ethylene glycolbis(sulfosuccinimidyl succinate) (sulfo-EGS), disuccinimidyl tartrate (DST), disulfosuccinimidyl tartrate (sulfo-DST), bis[2-(succinimido oxycarbonyloxy)ethyl]sulfone (BSOCOES), bis[2-(sulfosuccinimido oxycarbonyloxy)ethyl]sulfone (sulfo-BSOCOES) or the like. These are commercially available.

To form a dimer of the single-chain Fv it is preferable to select a linker suitable to dimerize in the solution such as culture medium more than 20%, preferably more than 50%, more preferably more than 80%, most preferably more than 90% of the single-chain Fv produced in the host cells. Specifically, preferable is a linker composed of 2 to 12 amino acids, preferably 3 to 10 amino acids or other linkers corresponding thereto.

Preparation of Reconstructed Polypeptides

The reconstructed polypeptide binding to cells with human IAP are obtainable by connecting an H chain V region and an L chain V region derived from monoclonal antibodies against human IAP through the aforementioned linker. Examples of the single-chain Fvs are MABL1-scFv comprising the H chain V region and the L chain V region derived from the antibody MABL-1, and MABL2-scFv comprising the H chain V region and the L chain V region derived from the antibody MABL-2.

For the preparation of the reconstructed polypeptide, a signal peptide may be attached to N-terminal of the polypeptide where the polypeptide is desired to be a secretory peptide. A well-known amino acid sequence useful for the purification of polypeptide such as the FLAG sequence may be attached for the efficient purification of the polypeptide. The polypeptide can be efficiently purified with anti-FLAG antibody.

For the preparation of the reconstructed polypeptide of the invention, it is necessary to obtain a DNA encoding the reconstructed polypeptide, i.e. a DNA encoding the single-chain Fv or a DNA encoding the reconstructed polypeptide monomer. These DNAs are obtainable from the DNAs encoding the H chain V region and the L chain V region of MABL1-scFv and/or MABL2-scFv. They are also obtainable by amplifying a DNA encoding desired amino acid sequence within the aforementioned sequence by PCR using the DNA as a template and a pair of primers corresponding to both ends thereof.

In the case where each V region having partially modified amino acid sequence is desired, the V regions in which one or some amino acids are modified, i.e. deleted, replaced or added can be obtained by a procedure known in the art using PCR. A part of the amino acid sequence in the V region is preferably modified by the PCR known in the art in order to prepare the reconstructed polypeptide which is sufficiently active against the specific antigen.

For the determination of primers for the PCR amplification, it is necessary to decide the type of the H chain and L chain of the antibody MABL-1 and/or the antibody MABL-2. It has been reported, however, that the antibody MABL-1 has κ type L chains and γ1 type H chains and the antibody MABL-2 has κ type L chains and γ2a type H chains (JP-Appl. 11-63557). For the PCR amplification of the DNA encoding the H chain and L chain of the antibody MABL-1 and/or the antibody MABL-2, primers described in Jones, S. T. et al., Bio/Technology, 9, 88-89, 1991 may be employed.

For the amplification of the L chain V regions of the antibody MABL-1 and the antibody MABL-2 using the polymerase chain reaction (PCR), 5'-end and 3'-end oligonucleotide primers are decided as aforementioned. In the same manner, 5'-end and 3'-end oligonucleotide primers are decided for the amplification of the H chain V regions of the antibody MABL-1 and the antibody MABL-2.

In embodiments of the invention, the 5'-end primers which contain a sequence "GANTC" providing the restriction enzyme Hinf I digestion site at the neighborhood of 5'-terminal thereof are used and the 3'-end primers which contain a nucleotide sequence "CCCGGG" providing the XmaI digestion site at the neighborhood of 5'-terminal thereof are used. Other restriction enzyme digestion sites may be used instead of these sites as long as they are used for subcloning a desired DNA fragment into a cloning vector.

Specifically designed PCR primers are employed to provide suitable nucleotide sequences at 5'-end and 3'-end of the cDNAs encoding the V regions of the antibodies MABL-1 and MABL-2 so that the cDNAs are readily inserted into an expression vector and appropriately function in the expression vector (e.g. this invention devises to increase transcription efficiency by inserting Kozak sequence). The V regions of the antibodies MABL-1 and MABL-2 obtained by amplifying by PCR using these primers are inserted into HEF expression vector containing the desired human C region (see WO92/19759). The cloned DNAs can be sequenced by using any conventional process which comprises, for example, inserting the DNAs into a suitable vector and then sequencing using the automatic DNA sequencer (Applied Biosystems).

A linker such as a peptide linker can be introduced into the reconstructed polypeptide of the invention in the following manner. Primers which have partially complementary sequence with the primers for the H chain V regions and the L chain V regions as described above and which code for the N-terminal or the C-terminal of the linker are designed. Then, the PCR procedure can be carried out using these primers to prepare a DNA encoding the peptide linker having desired amino acid sequence and length. The DNAs encoding the H chain V region and the L chain V region can be connected through the resulting DNA to produce the DNA encoding the reconstructed polypeptide of the invention which has the desired peptide linker. Once the DNA encoding one of the reconstructed polypeptides is prepared, the DNAs encoding the reconstructed polypeptides with or without the desired peptide linker can readily be produced by designing various primers for the linker and then carrying out the PCR using the primers and the aforementioned DNA as a template.

Each V region of the reconstructed polypeptide of the present invention can be humanized by using conventional techniques (e.g. Sato, K. et al., Cancer Res., 53, 851-856 (1993)). Once a DNA encoding a humanized Fv is prepared, a humanized single-chain Fv, a fragment of the humanized single-chain Fv, a humanized monoclonal antibody and a fragment of the humanized monoclonal antibody can readily be produced according to conventional methods. Preferably, amino acid sequences of the V regions thereof may be partially modified, if necessary.

Furthermore, a DNA derived from other mammalian origin, for example a DNA of human, can be produced in the same manner as used to produce DNA encoding the H chain V region and the L chain V region derived from mouse mentioned in the above. The resulting DNA can be used to prepare an H chain V region and an L chain V region of other mammal, especially human origin, a single-chain Fv derived from human and a fragment thereof, and a monoclonal antibody of human origin and a fragment thereof.

As mentioned above, when the aimed DNAs encoding the V regions of the reconstructed polypeptides and the V regions the reconstructed humanized polypeptides are prepared, the expression vectors containing them and hosts transformed with the vectors can be obtained according to conventional methods. Further, the hosts can be cultured according to a conventional method to produce the reconstructed single-chain Fv, the reconstructed humanized single-chain Fv, the humanized monoclonal antibodies and fragments thereof. They can be isolated from cells or a medium and can be purified into a homogeneous mass. For this purpose any isolation and purification methods conventionally used for proteins, e.g. chromatography, ultra-filtration, salting-out and dialysis, may be employed in combination, if necessary, without limitation thereto.

When the reconstructed single-chain Fv of the present invention is produced by culturing an animal cell such as COS7 cells or CHO cells, preferably CHO cells, in a serum-free medium, the reconstructed single-chain Fv is efficiently dimerized in the medium. The dimer of the single-chain Fv as formed above can be isolated stably and efficiently and preserved for a long period in the dimer form. The serum-free medium employed in the invention may be any medium conventionally used for the production of a recombinant protein without limit thereto.

For the production of the reconstructed polypeptides binding to cells with human IAP of the present invention, any expression systems can be employed, for example, eukaryotic cells such as animal cells, e.g., established mammalian cell lines, filamentous fungi and yeast, and prokaryotic cells such as bacterial cells e.g., $E.\ coli$. Preferably, the reconstructed polypeptides of the invention are expressed in mammalian cells, for example COS7 cells or CHO cells.

In these cases, conventional promoters useful for the expression in mammalian cells can be used. Preferably, human cytomegalovirus (HCMV) immediate early promoter is used. Expression vectors containing the HCMV promoter include HCMV-VH-HCγ 1, HCMV-VL-HCK and the like which are derived from pSV2neo (WO92/19759).

Additionally, other promoters for gene expression in mammal cell which may be used in the invention include virus promoters derived form retrovirus, polyoma virus, adenovirus and simian virus 40 (SV40) and promoters derived from mammal such as human polypeptide-chain elongation factor-1α (HEF-1α). SV40 promoter can easily be used according to the method of Mulligan, R. C., et al. (Nature 277, 108-114 (1979)) and HEF-1α promoter can also be used according to the methods of Mizushima, S. et al. (Nucleic Acids Research, 18, 5322 (1990)).

Replication origin (ori) which can be used in the invention includes ori derived from SV40, polyoma virus, adenovirus, bovine papilloma virus (BPV) and the like. For the purpose of the amplification of gene copy number in the host cell system and the like, an expression vector may contain, as a selection marker, phosphotransferase APH (3') II or I (neo) gene, thymidine kinase (TK) gene, $E.\ coli$ xanthine-guanine phosphoribosyl transferase (Ecogpt) gene or dihydrofolate reductase (DHFR) gene.

The antigen-binding activity of the reconstructed polypeptide as prepared above can be evaluated using the binding-inhibitory ability of the mouse antibodies, MABL-1 and MABL-2, to human IAP as an index. Concretely, the activity is evaluated in terms of the absence or presence of concentration-dependent inhibition of the binding of the mouse antibody MABL-2 to human IAP antigen as an index.

More in detail, animal cells transformed with an expression vector containing a DNA encoding the reconstructed polypeptide of the invention, e.g., COS7 cells or CHO cells, are cultured. The cultured cells and/or the supernatant of the medium or the reconstructed polypeptide purified from them are used to determine the binding to antigen. As a control, a supernatant of the cultural medium is used in which cells transformed only with the expression vector were cultured. A test sample of the reconstructed polypeptide of the invention or the supernatant of the control is added to mouse leukemia cell line, L1210 cells, expressing human Integrin Associated Protein (IAP) and then an assay such as the flow cytometry is carried out to evaluate the antigen-binding activity.

The apotosis-inducing effect in vitro is evaluated in the following manner: A test sample of the above reconstructed polypeptide is added to the cells into which the human IAP gene has been introduced and is evaluated on its inducibility of human IAP-specific cell death in the cells.

The apoptosis-inducing effect in vivo is evaluated in the following manner: A mouse model of human myeloma is prepared. To the mice is intravenously administered the monoclonal antibody or the reconstructed polypeptide of the invention, which induces apoptosis of nucleated blood cells having IAP. To mice of a control group is administered PBS alone. The induction of apoptosis is evaluated in terms of antitumor effect based on the change of human IgG content in serum of the mice and their survival time.

Hemagglutination effect is tested in the following manner: A suspension of erythrocytes is prepared from blood of healthy donors. Test samples of different concentrations are added to the suspension, which are then incubated to determine the hemagglutination.

Reconstructed polypeptides of the invention, which comprises two or more H chain V regions and two or more L chain V regions, may be a dimer, trimer or tetramer of the single-chain Fv comprising one H chain V region and one L chain V region, or a polypeptide in which two or more H chain V regions and two or more L chain V regions are connected. It is considered that owing to such construction the peptide mimics three dimensional structure of the antigen binding site of the parent monoclonal antibody and therefore retains an excellent antigen-binding property.

The polypeptide of the invention has a superior mobility to tissues or tumors over whole IgG and a remarkably reduced or no side effect of hemagglutination. Therefore, it is expected that the peptide of the invention can be used as a therapeutic agent for blood dyscrasia, for example, leukemia such as acute myeloid leukemia, chronic myelogenous leukemia, acute lymphoblastic leukemia, chronic lymphoblastic leukemia, adult T-cell leukemia, multiple myeloma, mixed leukemia and hairy cell leukemia, malignant lymphoma (Hodgkin's disease, non-Hodgkin's lymphoma), hypoplastic anemia, osteomyelodysplasia and polycythemia vera. It is further expected that the peptide of the invention can be used as a contrast agent by RI-labeling. The effect of the peptide can be enhanced by attaching to a RI-compound or a toxin.

BEST MODE FOR WORKING THE INVENTION

The present invention will concretely be illustrated in reference to the following examples, which in no way limit the scope of the invention.

For illustrating the production process of the reconstructed polypeptides of the invention, examples of producing single-chain Fvs are shown below. Mouse antibodies against human IAP, MABL-1 and MABL-2 were used in the examples of producing the reconstructed polypeptides. Hybridomas MABL-1 and MABL-2 producing them respectively were internationally deposited as FERM BP-6100 and FERM BP-6101 with the National Institute of Bioscience and Human Technology, Agency of Industrial Science and Technology, Minister of International Trade and Industry (1-3 Higasi 1-chome, Tsukuba-shi, Ibaraki-ken, Japan), an authorized depositary for microorganisms, on Sep. 11, 1997.

EXAMPLE 1

Cloning of DNAs Encoding V Region of Mouse Monoclonal Antibodies to Human IAP

DNAs encoding variable regions of the mouse monoclonal antibodies to human IAP, MABL-1 and MABL-2, were cloned as follows.

1.1 Preparation of Messenger RNA (mRNA)

mRNAs of the hybridomas MABL-1 and MABL-2 were obtained by using mRNA Purification Kit (Pharmacia Biotech).

1.2 Synthesis of Double-Stranded cDNA

Double-stranded cDNA was synthesized from about 1 μg of the mRNA using Marathon cDNA Amplification Kit (CLONTECH) and an adapter was linked thereto.

1.3 PCR Amplification of Genes Encoding Variable Regions of an Antibody by

PCR was carried out using Thermal Cycler (PERKIN ELMER).

(1) Amplification of a Gene Coding for L Chain V Region of MABL-1

Primers used for the PCR method are Adapter Primer-1 (CLONTECH) shown in SEQ ID No. 1, which hybridizes to a partial sequence of the adapter, and MKC (Mouse Kappa Constant) primer (Bio/Technology, 9, 88-89, 1991) shown in SEQ ID No. 2, which hybridizes to the mouse kappa type L chain V region.

50 μl of the PCR solution contains 5 μl of 10×PCR Buffer II, 2 mM $MgCl_2$, 0.16 mM dNTPs (dATP, dGTP, dCTP and dTTP), 2.5 units of a DNA polymerase, AmpliTaq Gold (PERKIN ELMER), 0.2 μM of the adapter primer of SEQ ID No. 1, 0.2 μM of the MKC primer of SEQ ID No. 2 and 0.1 μg of the double-stranded cDNA derived from MABL-1. The solution was preheated at 94° C. of the initial temperature for 9 minutes and then heated at 94° C. for 1 minute, at 60° C. for 1 minute and at 72° C. for 1 minute 20 seconds in order. This temperature cycle was repeated 35 times and then the reaction mixture was further heated at 72° C. for 10 minutes.

(2) Amplification of cDNA Encoding H Chain V Region of MABL-1

The Adapter Primer-1 shown in SEQ ID No. 1 and MHC-γ1 (Mouse Heavy Constant) primer (Bio/Technology, 9, 88-89, 1991) shown in SEQ ID No. 3 were used as primers for PCR.

The amplification of cDNA was performed according to the method of the amplification of the L chain V region gene, which was described in Example 1.3-(1), except for using 0.2 μM of the MHC-γ1 primer instead of 0.2 μM of the MKC primer.

(3) Amplification of cDNA Encoding L Chain V Region of MABL-2

The Adapter Primer-1 of SEQ ID No. 1 and the MKC primer of SEQ ID No. 2 were used as primers for PCR.

The amplification of cDNA was carried out according to the method of the amplification of the L chain V region gene of MABL-1 which was described in Example 1.3-(1), except for using 0.1 μg of the double-stranded cDNA derived from MABL-2 instead of 0.1 μg of the double-stranded cDNA from MABL-1.

(4) Amplification of cDNA Encoding H Chain V Region of MABL-2

The Adapter Primer-1 of SEQ ID No. 1 and MHC-γ2a primer (Bio/Technology, 9, 88-89, 1991) shown in SEQ ID No. 4 were used as primers for PCR.

The amplification of cDNA was performed according to the method of the amplification of the L chain V region gene, which was described in Example 1.3-(3), except for using 0.2 μM of the MHC-γ2a primer instead of 0.2 μM of the MKC primer.

1.4 Purification of PCR Products

The DNA fragment amplified by PCR as described above was purified using the QIAquick PCR Purification Kit (QIAGEN) and dissolved in 10 mM Tris-HCl (pH 8.0) containing 1 mM EDTA.

1.5 Ligation and Transformation

About 140 ng of the DNA fragment comprising the gene encoding the mouse kappa type L chain V region derived from MABL-1 as prepared above was ligated with 50 ng of pGEM-T Easy vector (Promega) in the reaction buffer comprising 30 mM Tris-HCl (pH 7.8), 10 mM $MgCl_2$, 10 mM dithiothreitol, 1 mM ATP and 3 units of T4 DNA Ligase (Promega) at 15° C. for 3 hours.

Then, 1 μl of the reaction mixture was added to 50 μl of *E. coli* DH5α competent cells (Toyobo Inc.) and the cells were stored on ice for 30 minutes, incubated at 42° C. for 1 minute and stored on ice for 2 minutes again. 100 μl of SOC medium (GIBCO BRL) was added. The cells of *E. coli* were plated on LB (Molecular Cloning: A Laboratory Manual, Sambrook et al., Cold Spring Harbor Laboratory Press, 1989) agar medium containing 100 μg/ml of ampicillin (SIGMA) and cultured at 37° C. overnight to obtain the transformant of *E. coli*.

The transformant was cultured in 3 ml of LB medium containing 50 μg/ml of ampicillin at 37° C. overnight and the plasmid DNA was prepared from the culture using the QIAprep Spin Miniprep Kit (QIAGEN).

The resulting plasmid comprising the gene encoding the mouse kappa type L chain V region derived from the hybridoma MABL-1 was designated as pGEM-M1L.

According to the same manner as described above, a plasmid comprising the gene encoding the mouse H chain V region derived from the hybridoma MABL-1 was prepared from the purified DNA fragment and designated as pGEM-M1H.

A plasmid comprising the gene encoding the mouse kappa type L chain V region derived from the hybridoma MABL-2 was prepared from the purified DNA fragment and designated as pGEM-M2L.

A plasmid comprising the gene encoding the mouse H chain V region derived from the hybridoma MABL-2 was prepared from the purified DNA fragment and designated as pGEM-M2H.

EXAMPLE 2

DNA Sequencing

The nucleotide sequence of the cDNA encoding region in the aforementioned plasmids was determined using Auto DNA Sequencer (Applied Biosystem) and ABI PRISM Dye Terminator Cycle Sequencing Ready Reaction Kit (Applied Biosystem) according to the manufacturer's protocol.

The nucleotide sequence of the gene encoding the L chain V region from the mouse antibody MABL-1, which is included in the plasmid pGEM-M1L, is shown in SEQ ID NO: 5. Its encoded protein is shown in SEQ ID NO: 90.

The nucleotide sequence of the gene encoding the H chain V region from the mouse antibody MABL-1, which is included in the plasmid pGEM-M1H, is shown in SEQ ID NO: 6. Its encoded protein is shown in SEQ ID NO: 91.

The nucleotide sequence of the gene encoding the L chain V region from the mouse antibody MABL-2, which is included in the plasmid pGEM-M2L, is shown in SEQ ID NO: 7. Its encoded protein is shown in SEQ ID NO: 92.

The nucleotide sequence of the gene encoding the H chain V region from the mouse antibody MABL-2, which is included in the plasmid pGEM-M2H, is shown in SEQ ID NO: 8. Its encoded protein is shown in SEQ ID NO: 93.

EXAMPLE 3

Determination of CDR

The V regions of L chain and H chain generally have a similarity in their structures and each four framework regions therein are linked by three hypervariable regions, i.e., complementarity determining regions (CDR). An amino acid sequence of the framework is relatively well conserved, while an amino acid sequence of CDR has extremely high variation (Kabat, E. A., et al., "Sequences of Proteins of Immunological Interest", US Dept. Health and Human Services, 1983).

On the basis of these facts, the amino acid sequences of the variable regions from the mouse monoclonal antibodies to human IAP were applied to the database of amino acid sequences of the antibodies made by Kabat et al. to investigate the homology. The CDR regions were determined based on the homology as shown in Table 1.

TABLE 1

| Plasmid | SEQ ID No. (DNA) | SEQ ID No. (Protein) | CDR (1) | CDR (2) | CDR (3) |
|---|---|---|---|---|---|
| pGEM-M1L | 5 | 90 | 24-39 | 55-61 | 94-102 |
| pGEM-M1H | 6 | 91 | 31-35 | 50-66 | 99-106 |
| pGEM-M2L | 7 | 92 | 24-39 | 55-61 | 94-102 |
| pGEM-M2H | 8 | 93 | 31-35 | 50-66 | 99-106 |

EXAMPLE 4

Identification of Cloned cDNA Expression Preparation of Chimera MABL-1 Antibody and Chimera MABL-2 Antibody 4.1 Preparation of Vectors Expressing Chimera MABL-1 Antibody cDNA clones, pGEM-M1L and pGEM-M1H, encoding the V regions of the L chain and the H chain of the mouse antibody MABL-1, respectively, were modified by the PCR method and introduced into the HEF expression vector (WO92/19759) to prepare vectors expressing chimera MABL-1 antibody.

A forward primer MLS (SEQ ID No. 9) for the L chain V region and a forward primer MHS (SEQ ID No. 10) for the H chain V region were designed to hybridize to a DNA encoding the beginning of the leader sequence of each V region and to contain the Kozak consensus sequence (J. Mol. Biol., 196, 947-950, 1987) and HindIII restriction enzyme site. A reverse primer MLAS (SEQ ID No. 11) for the L chain V region and a reverse primer MHAS (SEQ ID No. 12) for the H chain V region were designed to hybridize to a DNA encoding the end of the J region and to contain the splice donor sequence and BamHI restriction enzyme site.

100 μl of a PCR solution comprising 10 μl of 10×PCR Buffer II, 2 mM MgCl$_2$, 0.16 mM dNTPs (dATP, dGTP, dCTP and dTTP), 5 units of DNA polymerase AmpliTaq Gold, 0.4 μM each of primers and 8 ng of the template DNA (pGEM-M1L or pGEM-M1H) was preheated at 94° C. of the initial temperature for 9 minutes and then heated at 94° C. for 1 minute, at 60° C. for 1 minute and at 72° C. for 1 minute 20 seconds in order. This temperature cycle was repeated 35 times and then the reaction mixture was further heated at 72° C. for 10 minutes.

The PCR product was purified using the QIAquick PCR Purification Kit (QIAGEN) and then digested with HindIII and BamHI. The product from the L chain V region was cloned into the HEF expression vector, HEF-κ and the product from the H chain V region was cloned into the HEF expression vector, HEF-γ. After DNA sequencing, plasmids containing a DNA fragment with a correct DNA sequence are designated as HEF-M1L and HEF-M1H, respectively.

4.2 Preparation of Vectors Expressing Chimera MABL-2 Antibodies

Modification and cloning of cDNA were performed in the same manner described in Example 4.1 except for using pGEM-M2L and pGEM-M2H as template DNA instead of pGEM-M1L and pGEM-M1H. After DNA sequencing, plasmids containing DNA fragments with correct DNA sequences are designated as HEF-M2L and HEF-M2H, respectively.

4.3 Transfection to COS7 Cells

The aforementioned expression vectors were tested in COS7 cells to observe the transient expression of the chimera MABL-1 and MABL-2 antibodies.

(1) Transfection with Genes for the Chimera MABL-1 Antibody

COS7 cells were co-transformed with the HEF-M1L and HEF-M1H vectors by electroporation using the Gene Pulser apparatus (BioRad). Each DNA (10 μg) and 0.8 ml of PBS with $1 \times 10^7$ cells/ml were added to a cuvette. The mixture was treated with pulse at 1.5 kV, 25 μF of electric capacity.

After the restoration for 10 minutes at a room temperature, the electroporated cells were transferred into DMEM culture medium (GIBCO BRL) containing 10% γ-globulin-free fetal bovine serum. After culturing for 72 hours, the supernatant was collected, centrifuged to remove cell fragments and recovered.

(2) Transfection with Genes Coding for the Chimera MABL-2 Antibody

The co-transfection to COS7 cells with the genes coding for the chimera MABL-2 antibody was carried out in the same manner as described in Example 4.3-(1) except for using the HEF-M2L and HEF-M2H vectors instead of the HEF-M1L and HEF-M1H vectors. The supernatant was recovered in the same manner.

4.4 Flow Cytometry

Flow cytometry was performed using the aforementioned culture supernatant of COS7 cells to measure binding to the antigen. The culture supernatant of the COS7 cells expressing the chimera MABL-1 antibody or the COS7 cells expressing the chimera MABL-2 antibody, or human IgG antibody (SIGMA) as a control was added to $4 \times 10^5$ cells of mouse leukemia cell line L1210 expressing human IAP and incubated on ice. After washing, the FITC-labeled anti-human IgG antibody (Cappel) was added thereto. After incubating and washing, the fluorescence intensity thereof was measured using the FACScan apparatus (BECTON DICKINSON).

Since the chimera MABL-1 and MABL-2 antibodies were specifically bound to L1210 cells expressing human IAP, it is confirmed that these chimera antibodies have proper structures of the V regions of the mouse monoclonal antibodies MABL-1 and MABL-2, respectively (FIGS. 1-3).

EXAMPLE 5

Preparation of Reconstructed Single-Chain Fv (scFv) of the Antibody MABL-1 and Antibody MABL-2

5.1 Preparation of Reconstructed Single-Chain Fv of Antibody MABL-1

The reconstructed single-chain Fv of antibody MABL-1 was prepared as follows. The H chain V region and the L chain V of antibody MABL-1, and a linker were respectively amplified by the PCR method and were connected to produce the reconstructed single-chain Fv of antibody MABL-1. The production method is illustrated in FIG. 4. Six primers (A-F) were employed for the production of the single-chain Fv of antibody MABL-1. Primers A, C and E have a sense sequence and primers B, D and F have an antisense sequence.

The forward primer VHS for the H chain v region (Primer A, SEQ ID No. 13) was designed to hybridize to a DNA encoding the N-terminal of the H chain V region and to contain NcoI restriction enzyme recognition site. The reverse primer VHAS for H chain V region (Primer B, SEQ ID No. 14) was designed to hybridize to a DNA coding the C-terminal of the H chain V region and to overlap with the linker.

The forward primer LS for the linker (Primer C, SEQ ID No. 15) was designed to hybridize to a DNA encoding the N-terminal of the linker and to overlap with a DNA encoding the C-terminal of the H chain V region. The reverse primer LAS for the linker (Primer D, SEQ ID No. 16) was designed to hybridize to a DNA encoding the C-terminal of the linker and to overlap with a DNA encoding the N-terminal of the L chain V region.

The forward primer VLS for the L chain V region (Primer E, SEQ ID No. 17) was designed to hybridize to a DNA encoding the C-terminal of the linker and to overlap with a DNA encoding the N-terminal of the L chain V region. The reverse primer VLAS-FLAG for L chain V region (Primer F, SEQ ID No. 18) was designed to hybridize to a DNA encoding the C-terminal of the L chain V region and to have a sequence encoding the FLAG peptide (Hopp. T. P. et al., Bio/Technology, 6, 1204-1210, 1988), two stop codons and EcoRI restriction enzyme recognition site.

In the first PCR step, three reactions, A-B, C-D and E-F, were carried out and PCR products thereof were purified. Three PCR products obtained from the first PCR step were assembled by their complementarity. Then, the primers A and F were added and the full length DNA encoding the reconstructed single-chain Fv of antibody MABL-1 was amplified (Second PCR). In the first PCR, the plasmid pGEM-M1H encoding the H chain V region of antibody MABL-1 (see Example 2), a plasmid pSC-DP1 which comprises a DNA sequence (SEQ ID NO: 19) encoding a linker region comprising: Gly Gly Gly Gly Ser Gly Gly Gly Gly Ser Gly Gly Gly Gly Ser (SEQ ID NO: 94) (Huston, J. S., et al., Proc. Natl. Acad. Sci. USA, 85, 5879-5883, 1988) and the plasmid pGEM-M1L encoding the L chain V region of antibody MABL-1 (see Example 2) were employed as template, respectively.

50 μl of the solution for the first PCR step comprises 5 μl of 10×PCR Buffer II, 2 mM MgCl$_2$, 0.16 mM dNTPs, 2.5 units of DNA polymerase, AmpliTaq Gold (PERKIN ELMER), 0.4 μM each of primers and 5 ng each of template DNA. The PCR solution was preheated at 94° C. of the initial temperature for 9 minutes and then heated at 94° C. for 1 minute, at 65° C. for 1 minute and at 72° C. for 1 minute and 20 seconds in order. This temperature cycle was repeated 35 times and then the reaction mixture was further heated at 72° C. for 7 minutes.

The PCR products A-B (371 bp), C-D (63 bp) and E-F (384 bp) were purified using the QIAquick PCR Purification Kit (QIAGEN) and were assembled in the second PCR. In the second PCR, 98 μl of a PCR solution comprising 120 ng of the first PCR product A-B, 20 ng of the PCR product C-D and 120 ng of the PCR product E-F, 10 μl of 10×PCR Buffer II, 2 mM MgCl$_2$, 0.16 mM dNTPs, 5 units of DNA polymerase AmpliTaq Gold (PERKIN ELMER) was preheated at 94° C. of the initial temperature for 8 minutes and then heated at 94° C. for 2 minutes, at 65° C. for 2 minutes and at 72° C. for 2 minutes in order. This temperature cycle was repeated twice and then 0.4 μM each of primers A and F were added into the reaction, respectively. The mixture was preheated at 94° C. of the initial temperature for 1 minutes and then heated at 94° C. for 1 minute, at 65° C. for 1 minute and at 72° C. for 1 minute and 20 seconds in order. This temperature cycle was repeated 35 times and then the reaction mixture was further heated at 72° C. for 7 minutes.

A DNA fragment of 843 bp produced by the second PCR was purified and digested by NcoI and EcoRI. The resultant DNA fragment was cloned into pSCFVT7 vector. The expression vector pSCFVT7 contains a pelB signal sequence suitable for E. coli periplasmic expression system (Lei, S. P., et al., J. Bacteriology, 169, 4379-4383, 1987). After the DNA sequencing, the plasmid containing the DNA fragment encoding correct amino acid sequence of the reconstructed single-chain Fv of antibody MABL-1 is designated as "pscM1" (see FIG. 5). The nucleotide sequence and the amino acid sequence of the reconstructed single-chain Fv of antibody MABL-1 contained in the plasmid pscM1 are shown in SEQ ID No. 20. The corresponding amino acid sequence is shown in SEQ ID NO. 95.

The pscM1 vector was modified by the PCR method to prepare a vector expressing the reconstructed single-chain Fv of antibody MABL-1 in mammalian cells. The resultant DNA fragment was introduced into pCHO1 expression vector. This expression vector, pCHO1, was constructed by digesting DHFR-ΔE-rvH-PM1-f (WO92/19759) with EcoRI and SmaI to eliminate the antibody gene and connecting the EcoRI-NotI-BamHI Adapter (Takara Shuzo) thereto.

As a forward primer for PCR, Sal-VHS primer shown in SEQ ID No. 21 was designed to hybridize to a DNA encoding the N-terminal of the H chain V region and to contain SalI restriction enzyme recognition site. As a reverse primer for PCR, FRH1anti primer shown in SEQ ID No. 22 was designed to hybridize to a DNA encoding the end of the first framework sequence.

100 μl of PCR solution comprising 10 μl of 10×PCR Buffer II, 2 mM MgCl$_2$, 0.16 mM dNTPs, 5 units of the DNA polymerase, AmpliTaq Gold, 0.4 μM each of primer and 8 ng of the template DNA (pscM1) was preheated at 95° C. of the initial temperature for 9 minutes and then heated at 95° C. for 1 minute, at 60° C. for 1 minute and at 72° C. for 1 minute and 20 seconds in order. This temperature cycle was repeated 35 times and then the reaction mixture was further heated at 72° C. for 7 minutes.

The PCR product was purified using the QIAquick PCR Purification Kit (QIAGEN) and digested by SalI and MboII to obtain a DNA fragment encoding the N-terminal of the reconstructed single-chain Fv of antibody MABL-1 The pscM1 vector was digested by MboII and EcoRI to obtain a DNA fragment encoding the C-terminal of the reconstructed single-chain Fv of antibody MABL-1. The SalI-MboII DNA fragment and the MboII-EcoRI DNA fragment were cloned into pCHO1-Igs vector. After DNA sequencing, the plasmid comprising the desired DNA sequence was designated as "pCHOM1" (see FIG. 6). The expression vector, pCHo1-Igs, contains a mouse IgG1 signal sequence suitable for the secretion-expression system in mammalian cells (Nature, 322, 323-327, 1988). The nucleotide sequence and the amino acid sequence of the reconstructed single-chain Fv of antibody MABL-1 contained in the plasmid pCHOM1 are shown in SEQ ID No. 23. The corresponding amino acid sequence is shown in SEQ ID NO. 96.

5.2 Preparation of Reconstructed Single-Chain Fv of Antibody MABL-2

The reconstructed single-chain Fv of antibody MABL-2 was prepared in accordance with the aforementioned Example 5.1. Employed in the first PCR step were plasmid pGEM-M2H encoding the H chain V region of MABL-2 (see Example 2) instead of pGEM-M1H and plasmid pGEM-M2L encoding the L chain V region of MABL-2 (see Example 2) instead of pGEM-M1L, to obtain a plasmid pscM2 which comprises a DNA fragment encoding the desired amino acid sequence of the single-chain Fv of antibody MABL-2. The nucleotide sequence and the amino acid sequence of the reconstructed single-chain Fv of antibody MABL-2 contained in the plasmid pscM2 are shown in SEQ ID No. 24. The corresponding amino acid sequence is shown in SEQ ID NO. 97.

The pscM2 vector was modified by the PCR method to prepare a vector, pCHOM2, for the expression in mammalian cells which contains the DNA fragment encoding the correct amino acid sequence of reconstructed the single-chain Fv of antibody MABL-2. The nucleotide sequence and the amino acid sequence of the reconstructed single-chain Fv of antibody MABL-2 contained in the plasmid pCHOM2 are shown in SEQ ID No. 25. The corresponding amino acid sequence is shown in SEQ ID NO. 98.

5.3 Transfection to COS7 Cells

The pCHOM2 vector was tested in COS7 cells to observe the transient expression of the reconstructed single-chain Fv of antibody MABL-2.

The COS7 cells were transformed with the pCHOM2 vector by electroporation using the Gene Pulser apparatus (Bio-Rad). The DNA (10 μg) and 0.8 ml of PBS with $1 \times 10^7$ cells/ml were added to a cuvette. The mixture was treated with pulse at 1.5 kV, 25 μF of electric capacity.

After the restoration for 10 minutes at a room temperature, the electroporated cells were transferred into IMDM culture medium (GIBCO BRL) containing 10% fetal bovine serum. After culturing for 72 hours, the supernatant was collected, centrifuged to remove cell fragments and recovered.

5.4 Detection of the Reconstructed Single-Chain Fv of Antibody MABL-2 in Culture Supernatant of COS7 Cells The existence of the single-chain Fv of antibody MABL-2 in the culture supernatant of COS7 cells which had been transfected with the pCHOM2 vector was confirmed by the Western Blotting method.

The culture supernatant of COS7 cells transfected with the pCHOM2 vector and the culture supernatant of COS7 cells transfected with the pCHO1 as a control were subjected to SDS electrophoresis and transferred to REINFORCED NC membrane (Schleicher & Schuell). The membrane was blocked with 5% skim milk (Morinaga Nyu-gyo), washed with 0.05% Tween 20-PBS and mixed with an anti-FLAG antibody (SIGMA). The membrane was incubated at room temperature, washed and mixed with alkaline phosphatase-conjugated mouse IgG antibody (Zymed). After incubating and washing at room temperature, the substrate solution (Kirkegaard Perry Laboratories) was added to develop color (FIG. 7).

A FLAG-peptide-specific protein was detected only in the culture supernatant of the pCHOM2 vector-introduced COS7 cells and thus it is confirmed that the reconstructed single-chain Fv of antibody MABL-2 was secreted in this culture supernatant.

5.5 Flow Cytometry

Flow cytometry was performed using the aforementioned COS7 cells culture supernatant to measure the binding to the antigen. The culture supernatant of the COS7 cells expressing the reconstructed single-chain Fv of antibody MABL-2 or the culture supernatant of COS7 cells transformed with pCHO1 vector as a control was added to 2×10⁵ cells of the mouse leukemia cell line L1210 expressing human Integrin Associated Protein (IAP) or the cell line L1210 transformed with pCOS1 as a control. After incubating on ice and washing, the mouse anti-FLAG antibody (SIGMA) was added. Then the cells were incubated and washed. Then, the FITC labeled anti-mouse IgG antibody (BECTON DICKINSON) was added thereto and the cells were incubated and washed again. Subsequently, the fluorescence intensity was measured using the FACScan apparatus (BECTON DICKINSON).

Since the single-chain Fv of antibody MABL-2 was specifically bound to L1210 cells expressing human IAP, it is confirmed that the reconstructed single-chain Fv of antibody MABL-2 has an affinity to human Integrin Associated Protein (IAP) (see FIGS. 8-11).

5.6 Competitive ELISA

The binding activity of the reconstructed single-chain Fv of antibody MABL-2 was measured based on the inhibiting activity against the binding of mouse monoclonal antibodies to the antigen.

The anti-FLAG antibody adjusted to 1 µg/ml was added to each well on 96-well plate and incubated at 37° C. for 2 hours. After washing, blocking was performed with 1% BSA-PBS. After incubating and washing at a room temperature, the culture supernatant of COS7 cells into which the secretion-type human IAP antigen gene (see SEQ ID NOS 26 and 99) had been introduced was diluted with PBS into twofold volume and added to each well. After incubating and washing at a room temperature, a mixture of 50 µl of the biotinized MABL-2 antibody adjusted to 100 ng/ml and 50 µl of sequentially diluted supernatant of the COS7 cells expressing the reconstructed single-chain Fv of antibody MABL-2 were added into each well. After incubating and washing at a room temperature, the alkaline phosphatase-conjugated streptoavidin (Zymed) was added into each well. After incubating and washing at a room temperature, the substrate solution (SIGMA) was added and absorbance of the reaction mixture in each well was measured at 405 nm.

The results revealed that the reconstructed single-chain Fv of antibody MABL-2 (MABL2-scFv) evidently inhibited concentration-dependently the binding of the mouse antibody MABL-2 to human IAP antigen in comparison with the culture supernatant of the PCHO1-introduced COS7 cells as a control (FIG. 12). Accordingly, it is suggested that the reconstructed single-chain Fv of antibody MABL-2 has the correct structure of each of the V regions from the mouse monoclonal antibody MABL-2.

5.7 Apoptosis-Inducing Effect in Vitro

An apoptosis-inducing action of the reconstructed single-chain Fv of antibody MABL-2 was examined by Annexin-V staining (Boehringer Mannheim) using the L1210 cells transfected with human IAP gene, the L1210 cells transfected with the pCOS1 vector as a control and CCRF-CEM cells.

To each 1×10⁵ cells of the above cells was added the culture supernatant of the COS7 cells expressing the reconstructed single-chain Fv of antibody MABL-2 or the culture supernatant of COS7 cells transfected with the pCHO1 vector as a control at 50% final concentration and the mixtures were cultured for 24 hours. Then, the Annexin-V staining was performed and the fluorescence intensity was measured using the FACScan apparatus (BECTON DICKINSON).

Results of the Annexin-V staining are shown in FIGS. 13-18, respectively. Dots in the left-lower region represent living cells and dots in the right-lower region represent cells at the early stage of apoptosis and dots in the right-upper region represent cells at the late stage of apoptosis. The results show that the reconstructed single-chain Fv of antibody MABL-2 (MABL2-scFv) remarkably induced cell death of L1210 cells specific to human IAP antigen (FIGS. 13-16) and that the reconstructed single-chain Fv also induced remarkable cell death of CCRF-CEM cells in comparison with the control (FIGS. 17-18).

5.8 Expression of MABL-2 Derived Single-Chain Fv in CHO Cells

CHO cells were transfected with the pCHOM2 vector to establish a CHO cell line which constantly expresses the single-chain Fv (polypeptide) derived from the antibody MABL-2.

CHO cells were transformed with the pCHOM2 vector by the electroporation using the Gene Pulser apparatus (Bio-Rad). A mixture of DNA (10 µg) and 0.7 ml of PBS with CHO cells (1×10⁷ cells/ml) was added to a cuvette. The mixture was treated with pulse at 1.5 kV, 25 µF of electric capacity. After the restoration for 10 minutes at a room temperature, the electroporated cells were transferred into nucleic acid free α-MEM medium (GIBCO BRL) containing 10% fetal bovine serum and cultured. The expression of desired protein in the resultant clones was confirmed by SDS-PAGE and a clone with a high expression level was selected as a cell line producing the single-chain Fv derived from the antibody MABL-2. The cell line was cultured in serum free medium CHO-S-SFM II (GIBCO BRL) containing 10 nM methotrexate (SIGMA). Then, the culture supernatant was collected, centrifuged to remove cell fragments and recovered.

5.9 Purification of MABL-2 Derived Single-Chain Fv Produced in CHO Cells

The culture supernatant of the CHO cell line expressing the single-chain Fv obtained in Example 5.8 was concentrated up to twenty times using a cartridge for the artificial dialysis (PAN130SF, ASAHI MEDICALS). The concentrated solution was stored at −20° C. and thawed on purification.

Purification of the single-chain Fv from the culture supernatant of the CHO cells was performed using three kinds of chromatography, i.e., Blue-sepharose, a hydroxyapatite and a gel filtration.

(1) Blue-Sepharose Column Chromatography

The concentrated supernatant was diluted to ten times with 20 mM acetate buffer (pH 6.0) and centrifuged to remove insoluble materials (10000×rpm, 30 minutes). The supernatant was applied onto a Blue-sepharose column (20 ml) equilibrated with the same buffer. After washing the column with the same buffer, proteins adsorbed in the column were eluted by a stepwise gradient of NaCl in the same buffer, 0.1, 0.2, 0.3, 0.5 and up to 1.0 M. The pass-through fraction and each eluted fraction were analyzed by SDS-PAGE. The fractions in which the single-chain Fv were confirmed (the fractions eluted at 0.1 to 0.3M NaCl) were pooled and concentrated up to approximately 20 times using CentriPrep-10 (AMICON).

(2) Hydroxyapatite

The concentrated solution obtained in (1) was diluted to 10 times with 10 mM phosphate buffer (pH 7.0) and applied onto the hydroxyapatite column (20 ml, BIORAD). The column was washed with 60 ml of 10 mM phosphate buffer (pH 7.0). Then, proteins adsorbed in the column were eluted by a linear gradient of sodium phosphate buffer up to 200 mM (see FIG. 19). The analysis of each fraction by SDS-PAGE confirmed the single-chain Fv in fraction A and fraction B.

(3) Gel Filtration

Each of fractions A and B in (2) was separately concentrated with CentriPrep-10 and applied onto TSKgel G3000SWG column (21.5×600 mm) equilibrated with 20 mM acetate buffer (pH 6.0) containing 0.15 M NaCl. Chromatograms are shown in FIG. 20. The analysis of the fractions by SDS-PAGE confirmed that both major peaks (AI and BI) are of desired single-chain Fv. In the gel filtration analysis, the fraction A was eluted at 36 kDa of apparent molecular weight and the fraction B was eluted at 76 kDa. The purified single-chain Fvs (AI, BI) were analyzed with 15% SDS polyacrylamide gel. Samples were treated in the absence or presence of a reductant and the electrophoresis was carried out in accordance with the Laemmli's method. Then the protein was stained with Coomassie Brilliant Blue. As shown in FIG. 21, both AI and BI gave a single band at 35 kDa of apparent molecular weight, regardless of the absence or presence of the reductant. From the above, it is concluded that AI is a monomer of the single-chain Fv and BI is a non-covalently bound dimer of the single-chain Fv. The gel filtration analysis of the fractions AI and BI with TSKgel G3000SW column (7.5×60 mm) revealed that a peak of the monomer is detected only in the fraction AI and a peak of the dimer is detected only in the fraction BI (FIG. 22). The dimer fraction (fraction BI) accounted for 4 percent (%) of total single-chain Fvs. More than 90% of the dimer in the dimer fraction was stably preserved for more than a month at 40° C.

5.10 Construction of Vector Expressing Single-Chain Fv Derived from Antibody MABL-2 in *E. Coli* Cell The pscM2 vector was modified by the PCR method to prepare a vector effectively expressing the single-chain Fv from the antibody MABL-2 in *E. coli* cells. The resultant DNA fragment was introduced into pSCFVT7 expression vector.

As a forward primer for PCR, Nde-VHSm02 primer shown in SEQ ID No. 27 was designed to hybridize to a DNA encoding the N-terminal of the H chain V region and to contain a start codon and NdeI restriction enzyme recognition site. As a reverse primer for PCR, VLAS primer shown in SEQ ID No. 28 was designed to hybridize to a DNA encoding the C-terminal of the L chain V region and to contain two stop codons and EcoRI restriction enzyme recognition site. The forward primer, Nde-VHSm02, comprises five point mutations in the part hybridizing to the DNA encoding the N-terminal of the H chain V region for the effective expression in *E. coli*.

100 μl of a PCR solution comprising 10 μl of 10×PCR Buffer #1, 1 mM MgCl$_2$, 0.2 mM dNTPs, 5 units of KOD DNA polymerase (all from TOYOBO), 1 μM of each primer and 100 ng of a template DNA (pscM2) was heated at 98° C. for 15 seconds, at 65° C. for 2 seconds and at 74° C. for 30 seconds in order. This temperature cycle was repeated 25 times.

The PCR product was purified using the QIAquick PCR Purification Kit (QIAGEN) and digested by NdeI and EcoRI, and then the resulting DNA fragment was cloned into pSCFVT7 vector, from which pelB signal sequence had been eliminated by the digestion with NdeI and EcoRI. After DNA sequencing, the resulting plasmid comprising a DNA fragment with the desired DNA sequence is designated as "pscM2DEm02" (see FIG. 23). The nucleotide sequence and the amino acid sequence of the single-chain Fv derived from the antibody MABL-2 contained in the plasmid pscM2DEm02 are shown in SEQ ID No. 29. The corresponding amino acid sequence is shown in SEQ ID NO. 100.

5.11 Expression of Single-Chain Fv Derived from Antibody MABL-2 in *E. Coli* Cells

*E. coli* BL21(DE3)pLysS (STRATAGENE) was transformed with pscM2DEm02 vector to obtain a strain of *E. coli* expressing the single-chain Fv derived from antibody MABL-2. The resulting clones were examined for the expression of the desired protein using SDS-PAGE, and a clone with a high expression level was selected as a strain producing the single-chain Fv derived from antibody MABL-2.

5.12 Purification of Single-Chain Fv Derived from Antibody MABL-2 Produced in *E. Coli*

A single colony of *E. coli* obtained by the transformation was cultured in 3 ml of LB medium at 28° C. for 7 hours and then in 70 ml of LB medium at 28° C. overnight. This preculture was transplanted to 7 L of LB medium and cultured at 28° C. with stirring at 300 rpm using the Jar-fermenter. When an absorbance of the medium reached O.D.=1.5, the bacteria were induced with 1 mM IPTG and then cultured for 3 hours.

The culture medium was centrifuged (10000×g, 10 minutes) and the precipitated bacteria were recovered. To the bacteria was added 50 mM Tris-HCl buffer (pH 8.0) containing 5 mM EDTA, 0.1 M NaCl and 1% Triton X-100 and the bacteria were disrupted by ultrasonication (out put: 4, duty cycle: 70%, 1 minute×10 times). The suspension of disrupted bacteria was centrifuged (12000×g, 10 minutes) to precipitate inclusion body. Isolated inclusion body was mixed with 50 mM Tris-HCl buffer (pH 8.0) containing 5 mM EDTA, 0.1 M NaCl and 4% Triton X-100, treated by ultrasonication (out put: 4, duty cycle: 50%, 30 seconds×2 times) again and centrifuged (12000×g, 10 minutes) to isolate the desired protein as precipitate and to remove containment proteins included in the supernatant.

The inclusion body comprising the desired protein was lysed in 50 mM Tris-HCl buffer (pH 8.0) containing 6 M Urea, 5 mM EDTA and 0.1 M NaCl and applied onto Sephacryl S-300 gel filtration column (5×90 cm, Amersharm Pharmacia) equilibrated with 50 mM Tris-HCl buffer (pH 8.0) containing 4M Urea, 5 mM EDTA, 0.1 M NaCl and 10 mM mercaptoethanol at a flow rate of 5 ml/minutes to remove associated single chain Fvs with high-molecular weight. The obtained fractions were analyzed with SDS-PAGE and the fractions with high purity of the protein were diluted with the buffer used in the gel filtration up to O.D$_{280}$=0.25. Then, the fractions were dialyzed three times against 50 mM Tris-HCl buffer (pH 8.0) containing 5 mM EDTA, 0.1 M NaCl, 0.5 M Arg, 2 mM glutathione in the reduced form and 0.2 mM glutathione in the oxidized form in order for the protein to be refolded. Further, the fraction was dialyzed three times against 20 mM acetate buffer (pH 6.0) containing 0.15 M NaCl to exchange the buffer.

The dialysate product was applied onto Superdex 200 μg gel filtration column (2.6×60 cm, Amersharm Pharmacia) equilibrated with 20 mM acetate buffer (pH 6.0) containing 0.15 M NaCl to remove a small amount of high molecular weight protein which was intermolecularly crosslinked by S—S bonds. As shown in FIG. 24, two peaks, major and sub peaks, were eluted after broad peaks which are expectedly attributed to an aggregate with a high molecular weight. The analysis by SDS-PAGE (see FIG. 21) and the elution positions of the two peaks in the gel filtration analysis suggest that the major peak is of the monomer of the single-chain Fv and the sub peak is of the non-covalently bound dimer of the single-chain Fv. The non-covalently bound dimer accounted for 4 percent of total single-chain Fvs.

5.13 Apoptosis-Inducing Activity in Vitro of Single-Chain Fv Derived from Antibody MABL-2

An apoptosis-inducing action of the single-chain Fv from antibody MABL-2 (MABL2-scFv) produced by the CHO cells and *E. coli* was examined according to two protocols by Annexin-V staining (Boehringer Mannheim) using the L1210 cells (hIAP/L1210) into which human IAP gene had been introduced.

In the first protocol sample antibodies at the final concentration of 3 μg/ml were added to $5 \times 10^4$ cells of hIAP/L1210 cell line and cultured for 24 hours. Sample antibodies, i.e., the monomer and the dimer of the single-chain Fv of MABL-2 from the CHO cells obtained in Example 5.9, the monomer and the dimer of the single-chain Fv of MABL-2 from *E. coli* obtained in Example 5.12, and the mouse IgG antibody as a control were analyzed. After culturing, the Annexin-V staining was carried out and the fluorescence intensity thereof was measured using the FACScan apparatus (BECTON DICKINSON).

In the second protocol sample antibodies at the final concentration of 3 μg/ml were added to $5 \times 10^4$ cells of hIAP/L1210 cell line, cultured for 2 hours and mixed with anti-FLAG antibody (SIGMA) at the final concentration of 15 μg/ml and further cultured for 22 hours. Sample antibodies of the monomer of the single-chain Fv of MABL-2 from the CHO cells obtained in Example 5.9 and the mouse IgG antibody as a control were analyzed. After culturing, the Annexin-V staining was carried out and the fluorescence intensity thereof was measured using the FACScan apparatus.

Results of the analysis by the Annexin-V staining are shown in FIGS. 25-31. The results show that the dimers of the single-chain Fv polypeptide of MABL-2 produced in the CHO cells and *E. coli* remarkably induced cell death (FIGS. 26, 27) in comparison with the control (FIG. 25), while no apoptosis-inducing action was observed in the monomers of the single-chain Fv polypeptide of MABL-2 produced in the CHO cells and *E. coli* (FIGS. 28, 29). When anti-FLAG antibody was used together, the monomer of the single-chain Fv polypeptide derived from antibody MABL-2 produced in the CHO cells induced remarkably cell death (FIG. 31) in comparison with the control (FIG. 30).

5.14 Antitumor Effect of the Monomer and the Dimer of scFv/CHO Polypeptide with a Model Mouse of Human Myeloma (1) Quantitative Measurement of Human IgG in Mouse Serum Measurement of human IgG (M protein) produced by human myeloma cell and contained in mouse serum was carried out by the following ELISA. 100 μL of goat anti-human IgG antibody (BIOSOURCE, Lot#7902) diluted to 1 μg/mL with 0.1% bicarbonate buffer (pH 9.6) was added to each well on 96 wells plate (Nunc) and incubated at 4° C. overnight so that the antibody was immobilized. After blocking, 100 μL of the stepwisely diluted mouse serum or human IgG (CAPPEL, Lot#00915) as a standard was added to each well and incubated for 2 hours at a room temperature. After washing, 100 μL of alkaline phosphatase-labeled anti-human IgG antibody (BIOSOURCE, Lot#6202) which had been diluted to 5000 times was added, and incubation was carried out for 1 hour at a room temperature. After washing, a substrate solution was added. After incubation, absorbance at 405 nm was measured using the MICROPLATE READER Model 3550 (BioRad). The concentration of human IgG in the mouse serum was calculated based on the calibration curve obtained from the absorbance values of human IgG as the standard.

(2) Preparation of Antibodies for Administration

The monomer and the dimer of the scFv/CHO polypeptide were respectively diluted to 0.4 mg/mL or 0.25 mg/mL with sterile filtered PBS(−) on the day of administration to prepare samples for the administration.

(3) Preparation of a Mouse Model of Human Myeloma

A mouse model of human myeloma was prepared as follows. KPMM2 cells passaged in vivo (JP-Appl. 7-236475) by SCID mouse (Japan Clare) were suspended in RPMI1640 medium (GIBCO-BRL) containing 10% fetal bovine serum (GIBCO-BRL) and adjusted to $3 \times 10^7$ cells/mL. 200 μL of the KPMM2 cell suspension ($6 \times 10^6$ cells/mouse) was transplanted to the SCID mouse (male, 6 week-old) via caudal vein thereof, which had been subcutaneously injected with the asialo GM1 antibody (WAKO JUNYAKU, 1 vial dissolved in 5 mL) a day before the transplantation.

(4) Administration of Antibodies

The samples of the antibodies prepared in (2), the monomer (250 μL) and the dimer (400 μL), were administered to the model mice of human myeloma prepared in (3) via caudal vein thereof. The administration was started from three days after the transplantation of KPMM2 cells and was carried out twice a day for three days. As a control, 200 μL of sterile filtered PBS(−) was likewise administered twice a day for three days via caudal vein. Each group consisted of seven mice.

(5) Evaluation of Antitumor Effect of the Monomer and the Dimer of scFv/CHO Polypeptide with the Model Mouse of Human Myeloma The antitumor effect of the monomer and the dimer of scFv/CHO polypeptide with the model mice of human myeloma was evaluated in terms of the change of human IgG (M protein) concentration in the mouse serum and survival time of the mice. The change of human IgG concentration was determined by measuring it in the mouse serum collected at 24 days after the transplantation of KPMM2 cells by ELISA described in the above (1). The amount of serum human IgG (M protein) in the serum of the PBS(−)-administered group (control) increased to about 8500 μg/mL, whereas the amount of human IgG of the scFv/CHO dimer-administered group was remarkably low, that is, as low as one-tenth or less than that of the control group. Thus, the results show that the dimer of scFv/CHO strongly inhibits the growth of the KPMM2 cells (FIG. 32). As shown in FIG. 33, a remarkable elongation of the survival time was observed in the scFv/CHO dimer-administered group in comparison with the PBS(−)-administered group.

From the above, it is confirmed that the dimer of scFv/CHO has an antitumor effect for the human myeloma model mice. It is considered that the antitumor effect of the dimer of scFv/CHO, the reconstructed polypeptide of the invention, results from the apoptosis-inducing action of the reconstructed polypeptide.

5.15 Hemagglutination Test

Hemagglutination test and determination of hemagglutination were carried out in accordance with "Immuno-Biochemical Investigation", Zoku-Seikagaku Jikken Koza, edited by the Biochemical Society of Japan, published by Tokyo Kagaku Dojin.

Blood was taken from a healthy donor using heparin-treated syringes and washed with PBS(−) three times, and then erythrocyte suspension with a final concentration of 2% in PBS(−) was prepared. Test samples were the antibody MABL-2, the monomer and the dimer of the single-chain Fv polypeptide produced by the CHO cells, and the monomer and the dimer of the single-chain Fv polypeptide produced by E. coli, and the control was mouse IgG (ZYMED). For the investigation of the hemagglutination effect, round bottom 96-well plates available from Falcon were used. 50 μL per well of the aforementioned antibody samples and 50 μL of the 2% erythrocyte suspension were added and mixed in the well. After incubation for 2 hours at 37° C., the reaction mixtures were stored at 4° C. overnight and the hemagglutination thereof was determined. As a control, 50 μL per well of PBS(−) was used and the hemagglutination test was carried out in the same manner. The mouse IgG and antibody MABL-2 were employed at 0.01, 0.1, 1.0, 10.0 or 100.0 μg/mL of the final concentration of the antibodies. The single-chain Fvs were employed at 0.004, 0.04, 0.4, 4.0, 40.0 or 80.0 μg/mL of the final concentration and further at 160.0 μg/mL only in the case of the dimer of the polypeptide produced by E. coli. Results are shown in the Table 2. In the case of antibody MABL-2, the hemagglutination was observed at a concentration of more than 0.1 μg/mL, whereas no hemagglutination was observed for both the monomer and the dimer of the single-chain Fv.

sequence coding for a linker region, and VLLAS primer containing SalI restriction enzyme recognition site (SEQ ID NO 31).

100 μl of the PCR solution comprises 10 μl of 10×PCR Buffer #1, 1 mM MgCl$_2$, 0.2 mM dNTPs (dATP, dGTP, dCTP and dTTP), 5 units of KOD DNA polymerase (Toyobo, Inc.), 1 μM of each primer and 100 ng of the template DNA (pCHOM2). The PCR solution was heated at 94° C. for 30 seconds, at 50° C. for 30 seconds and at 74° C. for 1 minute in order. This temperature cycle was repeated 30 times.

The PCR product was purified using the QIAquick PCR Purification Kit (QIAGEN) and digested by SalI. The resultant DNA fragment was cloned into pBluescript KS.sup.+ vector (Toyobo, Inc.). After DNA sequencing, a plasmid comprising the desired DNA sequence was digested by SalI and the obtained DNA fragment was connected using Rapid DNA Ligation Kit (BOEHRINGER MANNHEIM) to pCHOM2 digested by SalI. After DNA sequencing, a plasmid comprising the desired DNA sequence is designated as "pCHOM2 (Fv).sub.2" (see FIG. 34). The nucleotide sequence and the amino acid sequence of the antibody MABL-2 sc(Fv).sub.2 region contained in the plasmid pCHOM2(Fv).sub.2 are shown in SEQ ID No. 32. The corresponding amino acid sequence is shown in SEQ ID NO. 101.

TABLE 2

H magglutination Test

|  | Control | 0.01 | 0.1 | 1 | 10 | 100 | μg/mL |
|---|---|---|---|---|---|---|---|
| mIgG | − | − | − | − | − | − |  |
| MABL-2 (intact) | − | − | + | +++ | +++ | ++ |  |

|  | Control | 0.004 | 0.04 | 0.4 | 4 | 40 | 80 | μg/mL |
|---|---|---|---|---|---|---|---|---|
| scFv/CHO monomer | − | − | − | − | − | − | − |  |
| scFv/CHO dimer | − | − | − | − | − | − | − |  |

|  | Control | 0.004 | 0.04 | 0.4 | 4 | 40 | 80 | 160 | μg/mL |
|---|---|---|---|---|---|---|---|---|---|
| scFv/E.coli monomer | − | − | − | − | − | − | − |  |  |
| scFv/E.coli dimer | − | − | − | − | − | − | − | − |  |

EXAMPLE 6

Reconstructed Polypeptide sc(Fv)$_2$ Comprising Two H Chain V Regions and Two L Chain V Regions and Antibody MABL-2 scFvs Having Linkers with Different Length 6.1 Construction of Plasmid Expressing Antibody MABL-2 sc(Fv)$_2$ For the preparation of a plasmid expressing the reconstructed polypeptide [sc(FV)$_2$] which comprises two H chain V regions and two L chain V regions derived from the antibody MABL-2, the aforementioned pCHOM2, which comprises the DNA encoding scFv derived from the MABL-2 described above, was modified by the PCR method as mentioned below and the resulting DNA fragment was introduced into pCHOM2.

Primers employed for the PCR are EF1 primer (SEQ ID NO: 30) as a sense primer, which is designed to hybridize to a DNA encoding EF1α, and an antisense primer (SEQ ID NO: 19), which is designed to hybridize to the DNA encoding C-terminal of the L chain V region and to contain a DNA 6.2 Preparation of Plasmid Expressing Antibody MABL-2 scFvs Having Linkers with Various Length The scFvs containing linkers with different length and the V regions which are designed in the order of [H chain]-[L chain] (hereinafter "HL") or [L chain]-[H chain] (hereinafter "LH") were prepared using, as a template, cDNAs encoding the H chain and the L chain derived from the MABL-2 as mentioned below.

To construct HL type scFv the PCR procedure was carried out using pCHOM2(Fv)$_2$ as a template. In the PCR step, a pair of CFHL-F1 primer (SEW ID NO: 33) and CFHL-R2 primer (SEQ ID NO: 34) or a pair of CFHL-F2 primer (SEQ ID NO: 35) and CFHL-R1 primer (SEQ ID NO: 36) and KOD polymerase were employed. The PCR procedure was carried out by repeating 30 times the temperature cycle consisting of 94° C. for 30 seconds, 60° C. for 30 seconds and 72° C. for 1 minute in order to produce a cDNA for the H chain containing a leader sequence at 5'-end or a cDNA for the L chain containing FLAG sequence at 3'-end thereof. The resultant cDNAs for the H chain and the L chain were mixed and PCR was carried out by repeating 5 times the temperature cycle consisting of 94° C. for 30 seconds, 60° C. for 30 seconds and 72° C. for 1 minute in order using the mixture as templates and the KOD polymerase. To the reaction mixture were added CFHL-F1 and CFHL-R1 primers and then the PCR reaction was performed by repeating 30 times of the aforementioned temperature cycle to produce a cDNA for HL-0 type without a linker.

To construct LH type scFv, the PCR reaction was carried out using, as a template, pGEM-M2L and pGEM-M2H which contain cDNAs encoding the L chain V region and the H chain V region from the antibody MABL-2, respectively (see JP-Appl. 11-63557). A pair of T7 primer (SEQ ID NO: 37) and CFLH-R2 primer (SEQ ID NO: 38) or a pair of CFLH-F2 primer (SEQ ID NO: 39) and CFLH-R1 (SEQ ID NO: 40) and the KOD polymerase (Toyobo Inc.) were employed. The PCR reaction was performed by repeating 30 times the temperature cycle consisting of 94° C. for 30 seconds, 60° C. for 30 seconds and 72° C. for 1 minute in sequential order to produce a cDNA of an L chain containing a leader sequence at 5'-end or a cDNA of an H chain containing FLAG sequence at 3'-end thereof. The resultant cDNAs of the L chain and the H chain were mixed and PCR was carried out using this mixture as templates and the KOD polymerase by repeating 5 times the temperature cycle consisting of 94° C. for 30 seconds, 60° C. for 30 seconds and 72° C. for 1 minute in order. To the reaction mixture were added T7 and CFLH-R1 primers and the reaction was performed by repeating 30 times of the aforementioned temperature cycle. The reaction product was used as a template and PCR was carried out using a pair of CFLH-F4 primer (SEQ ID NO: 41) and CFLH-R1 primer by repeating 30 times the temperature cycle consisting of 94° C. for 30 seconds, 60° C. for 30 seconds and 72° C. for 1 minute in order to produce a cDNA of LH-0 type without a linker.

The resultant cDNAs of LH-0 and HL-0 types were digested by EcoRI and BamHI restriction enzymes (Takara Shuzo) and the digested cDNAs were introduced into an expression plasmid INPEP4 for mammalian cells using Ligation High (Toyobo Inc.), respectively. Competent *E. coli* JM109 (Nippon Gene) was transformed with each plasmid and the desired plasmids were isolated from the transformed *E. coli* using QIAGEN Plasmid Maxi Kit (QUIAGEN). Thus plasmids pCF2LH-0 and pCF2HL-0 were prepared.

To construct the expression plasmids of HL type containing linkers with different size, pCF2HL-0, as a template, and CFHL-X3 (SEQ ID NO: 42), CFHL-X4 (SEQ ID NO: 43), CFHL-X5 (SEQ ID NO: 44), CFHL-X6 (SEQ ID NO: 45) or CFHL-X7 (SEQ ID NO: 46), as a sense primer, and BGH-1 (SEQ ID NO: 47) primer, as an antisense primer, which is complementary with the vector sequence were employed. PCR reaction was carried out using the KOD polymerase by repeating 30 times the temperature cycle consisting of 94° C. for 30 seconds, 60° C. for 30 seconds and 72° C. for 1 minute in order and the reaction products were digested by restriction enzymes XhoI and BamHI (Takara Shuzo). The digested fragments were introduced between XhoI and BamHI sites in the pCF2HL-0 using Ligation High (Toyobo Inc.), respectively. Competent *E. coli* JM109 was transformed with each plasmid and the desired plasmids were isolated from the transformed E. coli by using Qiagen Plasmid Maxi kit. Thus expression plasmids pCF2HL-3, pCF2HL-4, pCF2HL-5, pCF2HL-6 and pCF2HL-7 were prepared.

To construct expression plasmid for the transient expression in COS7 cells the plasmids pCF2HL-0, pCF2HL-3, pCF2HL-4, pCF2HL-5, pCF2HL-6 and pCF2HL-7 were digested by restriction enzymes EcoRI and BamHI (Takara Shuzo) and the resultant fragments of approximately 800 bp were purified with agarose gel electrophoresis. The obtained fragments were introduced between EcoRI and BamHI sites in an expression plasmid pCOS1 for the expression in mammalian cells by using Ligation High (Toyobo Inc.), respectively. Competent *E. coli* DH5α (Toyobo Inc.) was transformed with each plasmid and the desired plasmids were isolated from the transformed *E. coli* using Qiagen Plasmid Maxi kit. Thus the expression plasmids CF2HL-0/pCOS1, CF2HL-3/pCOS1, CF2HL-4/pCOS1, CF2HL-5/pCOS1, CF2HL-6/pCOS1 and CF2HL-7/pCOS1 were prepared.

As a typical example of these plasmids, the construction of the plasmid CF2HL-0/pCOS1 is illustrated in FIG. 35 and the nucleotide sequence and the amino acid sequence of MABL2-scFv <HL-0> contained in the plasmid are shown in SEQ ID No. 48. Nucleotide sequences and amino acid sequences of the linker regions in these plasmids are also shown in FIG. 36. The corresponding amino acid sequence is shown in SEQ ID NO. 102.

To construct the expression plasmids of LH type containing linkers with different size, pCF2LH-0, as a template, and CFLH-X3 (SEQ ID NO: 49), CFLH-X4 (SEQ ID NO: 50), CFLH-X5 (SEQ ID NO: 51), CFLH-X6 (SEQ ID NO: 52) or CFLH-X7 (SEQ ID NO: 53), as a sense primer, and BGH-1 primer, as an antisense primer, which is complementary with the vector sequence were employed. PCR reaction was carried out using the KOD polymerase by repeating 30 times the temperature cycle consisting of 94° C. for 30 seconds, 60° C. for 30 seconds and 72° C. for 1 minute in order and the reaction products were digested by restriction enzymes XhoI and BamHI. The digested fragments were introduced into the pCF2LH-0 between XhoI and BamHI sites using Ligation High, respectively. Competent *E. coli* DH5α (Toyobo Inc.) was transformed with each plasmid and the desired plasmids were isolated from the transformed *E. coli* using Qiagen Plasmid Maxi kit. Thus expression plasmids pCF2LH-3, pCF2LH-4, pCF2LH-5, pCF2LH-6 and pCF2LH-7 were prepared.

To construct expression plasmid for the transient expression in COS7 cells the plasmids pCF2LH-0, pCF2LH-3, pCF2LH-4, pCF2LH-5, pCF2LH-6 and pCF2LH-7 were digested by restriction enzymes EcoRI and BamHI (Takara Shuzo) and the resultant fragments of approximately 800 bp were purified with agarose gel electrophoresis. The obtained fragments were introduced between XhoI and BamHI sites in an expression plasmid pCOS1 for the expression in mammalian cells by using the Ligation High, respectively. Competent *E. coli* DH5α (Toyobo Inc.) was transformed with each plasmid and the desired plasmids were isolated from the transformed *E. coli* using the Qiagen Plasmid Maxi kit. Consequently, the expression plasmids CF2LH-0/pCOS1, CF2LH-3/pCOS1, CF2LH-4/pCOS1, CF2LH-5/pCOS1, CF2LH-6/pCOS1 and CF2LH-7/pCOS1 were prepared.

As a typical example of these plasmids, the construction of the plasmid CF2LH-0/pCOS1 is illustrated in FIG. 37 and the nucleotide sequence and the amino acid sequence of MABL2-scFv <LH-0> contained in the plasmid are shown in SEQ ID No. 54. Nucleotide sequences and amino acid sequences of the linker regions in these plasmids are also shown in FIG. 38. The corresponding amino acid sequence is shown in SEQ ID NO. 103.

6.3 Expression of scFvs and sc(Fv)$_2$ in COS7 Cells (1) Preparation of Culture Supernatant Using Serum-Containing Culture Medium The HL type and LH type of scFvs and sc(FV)$_2$ were transiently expressed in COS7 cells (JCRB9127, Japan Health Sciences Foundation). COS7 cells were subcultured in DMEM media (GIBCO BRL) containing 10% fetal bovine serum (HyClone) at 37° C. in carbon dioxide atmosphere incubator. The COS7 cells were transfected with CF2HL-0, 3~7/pCOS1, or CF2LH-0, 3~7/pCOS1 prepared in Example 6.2 or pCHOM2(Fv)$_2$ vectors by electroporation using the Gene Pulser apparatus (BioRad). The DNA (10 µg) and 0.25 ml of 2×10$^7$ cells/ml in DMEM culture medium containing 10% FBS and 5 mM BES (SIGMA) were added to a cuvette. After standing for 10 minutes the mixtures were treated with pulse at 0.17 kV, 950 µF of electric capacity. After the restoration for 10 minutes at room temperature, the electroporated cells were transferred into the DMEM culture medium (10% FBS) in 75 cm$^3$ flask. After culturing for 72 hours, the culture supernatant was collected and centrifuged to remove cell fragments. The culture supernatant was subjected to the filtration using 0.22 µm bottle top filter (FALCON) to obtain the culture supernatant (hereinafter "CM").

(2) Preparation of Culture Supernatant Using Serum-Free Culture Medium

Cells transfected in the same manner as (1) were transferred to the DMEM medium (10% FBS) in 75 cm$^3$ flask and cultured overnight. After the culture, the supernatant was discarded and the cells were washed with PBS and then added to CHO-S-SFM II medium (GIBCO BRL). After culturing for 72 hours, the culture supernatant was collected, centrifuged to remove cell fragments and filtered using 0.22 µm bottle top filter (FALCON) to obtain CM.

6.4 Detection of scFvs and sc(Fv)$_2$ in CM of COS7

The various MABL2-scFVs and sc(Fv)$_2$ in CM of COS7 prepared in the aforementioned Example 6.3 (2) were detected by Western Blotting method.

Each CM of COS7 was subjected to SDS-PAGE electrophoresis and transferred to REINFORCED NC membrane (Schleicher & Schuell). The membrane was blocked with 5% skim milk (Morinaga Nyu-gyo) and washed with TBS. Then an anti-FLAG antibody (SIGMA) was added thereto. The membrane was incubated at room temperature and washed. A peroxidase labeled mouse IgG antibody (Jackson Immuno Research) was added. After incubating and washing at room temperature, the substrate solution (Kirkegaard Perry Laboratories) was added to develop color (FIG. 39).

6.5 Flow Cytometry

Flow cytometry was performed using the culture supernatants of COS7 cells prepared in Example 6.3 (1) to measure the binding of the MABL2-scFVs and sc(Fv)$_2$ to human Integrin Associated Protein (IAP) antigen. The culture supernatants to be tested or a culture supernatant of COS7 cells as a control was added to 2×10$^5$ cells of the mouse leukemia cell line L1210 expressing human IAP. After incubating on ice and washing, 10 µg/mL of the mouse anti-FLAG antibody (SIGMA) was added and then the cells were incubated and washed. Then, the FITC labeled anti-mouse IgG antibody (BECTON DICKINSON) was added thereto and the cells were incubated and washed again. The fluorescence intensity was measured using the FACScan apparatus (BECTON DICKINSON). The results of the flow cytometry show that the MABL2-scFvs having linkers with different length and the sc(Fv)$_2$ in the culture supernatants of COS7 have high affinity to human IAP (see FIGS. 40a and 40b).

6.6 Apoptosis-Inducing Effect in Vitro

An apoptosis-inducing action of the culture supernatants of COS7 prepared in Example 6.3 (1) was examined by Annexin-V staining (Boehringer Mannheim) using the L1210 cells transfected with human IAP gene (hIAP/L1210).

To 5×10$^4$ cells of the hIAP/L1210 cells were added the culture supernatants of COS7 cells transfected with each vectors or a culture supernatant of COS7 cells as a control at 10% of the final concentration and the mixtures were cultured for 24 hours. Then, the Annexin-V/PI staining was performed and the fluorescence intensity was measured using the FACScan apparatus (BECTON DICKINSON). The results revealed that scFvs <HL3, 4, 6, 7, LH3, 4, 6, 7> and sc(Fv)$_2$ in CM of COS7 induced remarkable cell death of hIAP/L1210 cells. These results are shown in FIG. 41.

6.7 Construction of Vectors for the Expression of scFvs and sc(Fv)$_2$ in CHO Cells To isolate and purify MABL2-scFvs and sc(Fv)2 from culture supernatant, the expression vectors for expressing in CHO cells were constructed as below.

The EcoRI-BamHI fragments of pCF2HL-0, 3~7, and pCF2LH-0, 3~7 prepared in Example 6.2 were introduced between EcoRI and BamHI sites in an expression vector pCHO1 for CHO cells using the Ligation High. Competent *E. coli* DH5α was transformed with them. The plasmids were isolated from the transformed E. coli using QIAGEN Plasmid Midi kit (QIAGEN) to prepare expression plasmids pCHOM2HL-0, 3~7, and pCHOM2LH-0, 3~7.

6.8 Production of CHO Cells Expressing MABL2-scFvs <HL-0, 3~7>, MABL2-scFvs <LH-0, 3~7> and sc(Fv)$_2$ and Preparation of the Culture Supernatants Thereof CHO cells were transformed with each of the expression plasmids pCHOM2HL-0, 3~7, and pCHOM2LH-0, 3~7, constructed in Example 6.7 and pCHOM2(Fv)$_2$ vector to prepare the CHO cells constantly expressing each reconstructed polypeptide. As a typical example thereof, the production of the CHO cells constantly expressing MABL2-scFv <HL-5> or sc(Fv)$_2$ is illustrated as follows.

The expression plasmids pCHOM2HL-5 and pCHOM2(Fv)$_2$ were linearized by digesting with a restriction enzyme PvuI and subjected to transfection to CHO cells by electroporation using Gene Pulser apparatus (BioRad). The DNA (10 µg) and 0.75 ml of PBS with 1×10$^7$ cells/ml were added to a cuvette and treated with pulse at 1.5 kV, 25 µF of electric capacity. After the restoration for 10 minutes at room temperature, the electroporated cells were transferred into nucleic acid-containing α-MEM culture medium (GIBCO BRL) containing 10% fetal bovine serum and cultured. After culturing overnight, the supernatant was discarded. The cells were washed with PBS and added to nucleic acid-free α-MEM culture medium (GIBCO BRL) containing 10% fetal bovine serum. After culturing for two weeks, the cells were cultured in a medium containing 10 nM (final concentration) methotrexate (SIGMA), then 50 nM and 100 nM methotrexate. The resultant cells were cultured in serum-free CHO-S-SFM II medium (GIBCO BRL) in a roller bottle. The culture supernatant was collected, centrifuged to remove cell fragments and filtered using a filter with 0.22 µm of pore size to obtain CM, respectively.

According to the above, CHO cells which constantly express MABL2-scFvs <HL-0, -3, -4, -6, -7> and <LH-0, -3, -4, -5, -6, -7> and CMs thereof were obtained.

6.9 Purification of Dimer of MABL2-scFv <HL-5> and sc(Fv)$_2$

The MABL2-scFv <HL-5> and the sc(Fv)$_2$ were purified from CMs prepared in Example 6.8 by two types of purification method as below.

<Purification Method 1>

HL-5 and sc(Fv)$_2$ were purified by the anti-FLAG antibody affinity column chromatography utilizing the FLAG sequence located at C-terminal of the polypeptides and by gel filtration. One liter of CM as obtained in 6.8 was applied onto a column (7.9 ml) prepared with anti-FLAG M2 Affinity gel (SIGMA) equilibrated with 50 mM Tris-HCl buffer (TBS, pH 7.5) containing 150 mM NaCl. After washing the column with TBS, the scFv was eluted by 0.1 M glycine-HCl buffer, pH 3.5. The resultant fractions were analyzed by SDS-PAGE and the elution of the scFv was confirmed. The scFv fraction was mixed with Tween 20 up to 0.01% of the final concentration and concentrated using Centricon-10 (MILIPORE). The concentrate was applied onto TSKgel G3000SWG column (7.5×600 mm) equilibrated with 20 mM acetate buffer (pH 6.0) containing 150 mM NaCl and 0.01% Tween 20. At 0.4 mL/minute of the flow rate, the scFv was detected by the absorption at 280 nm. The HL-5 was eluted as the major fraction in the position of the dimer and the sc(FV)$_2$ was eluted in the position of the monomer.

<Purification Method 2>

HL-5 and sc(Fv)$_2$ were purified using three steps comprising ion exchange chromatography, hydroxyapatite and gel filtration. In the ion exchange chromatography, Q sepharose fast flow column (Pharmacia) was employed for HL-5 and SP-sepharose fast flow column was employed for sc(FV)$_2$. In and after the second step, HL-5 and sc(Fv)$_2$ were processed by the same procedure.

First Step for HL-5

CM of HL-5 was diluted to two times with 20 mM Tris-HCl buffer (pH 9.0) containing 0.02% Tween 20 and then the pH was adjusted to 9.0 with 1 M Tris. The solution was applied onto Q Sepharose fast flow column equilibrated with 20 mM Tris-HCl buffer (pH 8.5) containing 0.02% Tween 20. A polypeptide adsorbed to the column was eluted by a linear gradient of NaCl in the same buffer, from 0.1 to 0.55 M. Monitoring the eluted fractions by SDS-PAGE, the fractions containing HL-5 were collected and subjected to hydroxyapatite of the second step.

First Step for sc(Fv)$_2$

CM of the sc(FV)$_2$ was diluted to two times with 20 mM acetate buffer (pH 5.5) containing 0.02% Tween 20 and its pH was adjusted to 5.5 with 1 M acetic acid. The solution was applied onto a SP-Sepharose fast flow column equilibrated with 20 mM acetate buffer (pH 5.5) containing 0.02% Tween 20. A polypeptide adsorbed to the column was eluted by a linear gradient of NaCl in the buffer, from 0 to 0.5 M. Monitoring the eluted fractions by SDS-PAGE, the fractions containing the Sc(Fv)$_2$ were collected and subjected to hydroxyapatite of the second step.

Second Step: Hydroxyapatite Chromatography of HL-5 and sc(Fv)$_2$

The fractions of HL-5 and sc(Fv)$_2$ obtained in the first step were separately applied onto the hydroxyapatite column (Type I, BIORAD) equilibrated with 10 mM phosphate buffer containing 0.02% Tween 20, pH 7.0. After washing the column with the same buffer, polypeptides adsorbed to the column were eluted by a linear gradient of the phosphate buffer up to 0.5 M. Monitoring the eluted fractions by SDS-PAGE, the fractions containing the desired polypeptides were collected.

Third Step: Gel Filtration of HL-5 and sc(Fv)$_2$

Each fraction obtained at the second step was separately concentrated with CentriPrep-10 (MILIPORE) and applied onto a Superdex 200 column (2.6×60 cm, Pharmacia) equilibrated with 20 mM acetate buffer (pH 6.0) containing 0.02% Tween 20 and 0.15 M NaCl. HL-5 was eluted in the position of the dimer, and sc(Fv)HL-5 and sc(Fv)$_2$ were eluted in the position of the monomer as a major peek respectively.

Since the monomer of HL-5 was hardly detected by both purification methods, it is proved that the dimers of single-chain Fvs are formed in high yields when the linker for the single-chain Fv contains around 5 amino acids. Furthermore, the dimer of HL-5 and the sc(Fv)$_2$ were stably preserved for a month at 4° C. after the purification.

6.10 Evaluation of the Binding Activity of Purified Dimer of scFv <HL-5> and sc(Fv)$_2$ Against Antigen Flow cytometry was performed using the purified dimer of MABL2-scFv <HL-5> and the purified sc(Fv)$_2$ in order to evaluate the binding to human Integrin Associated Protein (IAP) antigen. 10 g/ml of the purified dimer of MABL2-scFv <HL-5>, the purified sc(Fv)$_2$, the antibody MABL-2 as a positive control or a mouse IgG (Zymed) as a negative control was added to 2×10$^5$ cells of the mouse leukemia cell line L1210 expressing human IAP (hIAP/L1210) or the cell line L1210 transformed with pCOS1 (pCOS1/L1210) as a control. After incubating on ice and washing, 10 g/mL of the mouse anti-FLAG antibody (SIGMA) was added and then the cells were incubated and washed. FITC labeled anti-mouse IgG antibody (BECTON DICKINSON) was added thereto and the cells were incubated and washed again. Then the fluorescence intensity was measured using the FACScan apparatus (BECTON DICKINSON).

Since the purified dimer of MABL2-scFv <HL-5> and the purified sc(FV)$_2$ were specifically bound to hIAP/L1210 cells, it is confirmed that the dimer of scFv <HL-5> and the sc(Fv)$_2$ have high affinity to human IAP (see FIG. 42).

6.11 Apoptosis-Inducing Activity in Vitro of Purified Dimer of scFv <HL-5> and sc(Fv)$_2$ An apoptosis-inducing action of the purified dimer of MABL2-scFv <HL-5> and the purified sc(Fv)$_2$ were examined by Annexin-V staining (Boehringer Mannheim) using the L1210 cells (hIAP/L1210) in which human IAP gene had been introduced and cells of human leukemic cell line CCRF-CEM.

Different concentrations of the purified dimer of MABL2-scFv <HL-5>, the purified MABL2-sc(Fv)$_2$, the antibody MABL-2 as a positive control or a mouse IgG as a negative control were added to 5×10$^4$ cells of hIAP/L1210 cell line or 1×10$^5$ cells of CCRF-CEM cell line. After culturing for 24 hours, the Annexin-V staining was carried out and the fluorescence intensity thereof was measured using the FACScan apparatus (BECTON DICKINSON). As a result the dimer of MABL2-scFv <HL-5> and the MABL2-sc(Fv)$_2$ remarkably induced cell death of hHIAP/L1210 and CCRF-CEM in concentration-dependent manner (see FIG. 43).

6.12 Hemagglutination Test of the Purified Dimer of scFv <HL-5> and the sc(Fv)$_2$ Hemagglutination test was carried out using different concentrations of the purified dimer of scFv <HL-5> and the purified sc(Fv)$_2$ in accordance with Example 5.15.

The hemagglutination was observed with the antibody MABL-2 as a positive control, whereas no hemagglutination was observed with both the single chain antibody MABL2-sc(Fv)$_2$ and the MABL2-scFv <HL-5>. Further, there was no substantial difference in the hemagglutination between two buffers employed with the antibody MABL-2. These results are shown in Table 3.

TABLE 3

| | | | | | | | H magglutination Test | | | | | | | | | |
|---|---|---|---|---|---|---|---|---|---|---|---|---|---|---|---|---|
| Diluent:PBS | cont | 28.9 | 14.45 | 7.225 | 3.6125 | 1.8063 | 0.9031 | 0.4516 | 0.2258 | 0.1129 | 0.0564 | 0.0282 | 0.0141 | 0.0071 | 0.0035 | 0.0018 (μg/ml) |
| MABL2-sc(Fv)2 | – | – | – | – | – | – | – | – | – | – | – | – | – | – | – | – |
| | cont | 28.0 | 14.0 | 7.0 | 3.5 | 1.75 | 0.875 | 0.4375 | 0.2188 | 0.1094 | 0.0547 | 0.0273 | 0.0137 | 0.0068 | 0.0034 | 0.0017 |
| MABL2-sc(Fv)<HL-5> | – | – | – | – | – | – | – | – | – | – | – | – | – | – | – | – |
| | cont | 80 | 40 | 20 | 10 | 5 | 2.5 | 1.25 | 0.625 | 0.3125 | 0.1563 | 0.0781 | 0.0391 | 0.0195 | 0.0098 | 0.0049 |
| MABL2-(intact) | – | + | + | + | + | + | + | + | + | + | ± | – | – | – | – | – |
| mIgG | – | – | – | – | – | – | – | – | – | – | – | – | – | – | – | – |
| Diluent:Acetate | cont | 80 | 40 | 20 | 10 | 5 | 2.5 | 1.25 | 0.625 | 0.3125 | 0.1563 | 0.0781 | 0.0391 | 0.0195 | 0.0098 | 0.0049 (μg/ml) |
| MABL2-(intact) | – | + | + | + | + | + | + | + | + | + | + | + | – | – | – | – |

6.13 Antitumor Effect of the Purified Dimer of scFv <HL-5> and the sc(Fv)$_2$ for a Model Mouse of Human Myeloma The antitumor effects were tested for the dimer of scFv <HL-5> and the sc(Fv)$_2$ prepared and purified in Examples 6.8 and 6.9. The test was performed by using the mouse model for human myeloma produced in Example 5.1 and determining the amount of M protein produced by human myeloma cells in the mouse serum using ELISA and examine survival time of the mice. Then, the antitumor effects of the dimer of scFv <HL-5> and the sc(Fv)$_2$ were evaluated in terms of the change of the amount of M protein in the mouse serum and the survival time of the mice.

In the test, the HL-5 and the sc(Fv)2 were employed as a solution at 0.01, 0.1 or 1 mg/mL in vehicle consisting of 150 mM NaCl, 0.02% Tween and 20 mM acetate buffer, pH 6.0 and administered to the mice at 0.1, 1 or 10 mg/kg of dosage. Control group of mice were administered only with the vehicle.

The mouse serum was gathered 26 days after the transplantation of the human myeloma cells and the amount of M protein in the serum was measured using ELISA according to Example 5.14. As a result, the amount of M protein in the serum of both mice groups administered with HL-5, the dimer and the sc(FV)$_2$ decreased in dose-dependent manner (see FIG. 44). Furthermore, a significant elongation of the survival time was observed in both groups administered with the HL-5 (FIG. 45) and with the sc(Fv)2 (FIG. 46) in comparison with the control group administered with the vehicle. These results show that the HL-5 and the sc(Fv)$_2$ of the invention have excellent antitumor effect in vivo.

EXPLANATION OF DRAWINGS

FIG. 36 illustrates a structure of the HL-type nucleotide (SEQ ID NOS 56, 58, 60, 62, 64 and 66, respectively, in order of appearance) and amino acid sequences (SEQ ID NOS 57, 59, 61, 63, 65 and 67, respectively, in order of appearance) of peptide linkers.

FIG. 38 illustrates a structure of the LH-type nucleotide (SEQ ID NOS 68, 70, 72, 74, 76 and 78, respectively, in order of appearance) and amino acid sequences (SEQ ID NOS 69, 71, 73, 75, 77 and 79, respectively, in order of appearance) of peptide linkers.

INDUSTRIAL APPLICABILITY

Figure 1:
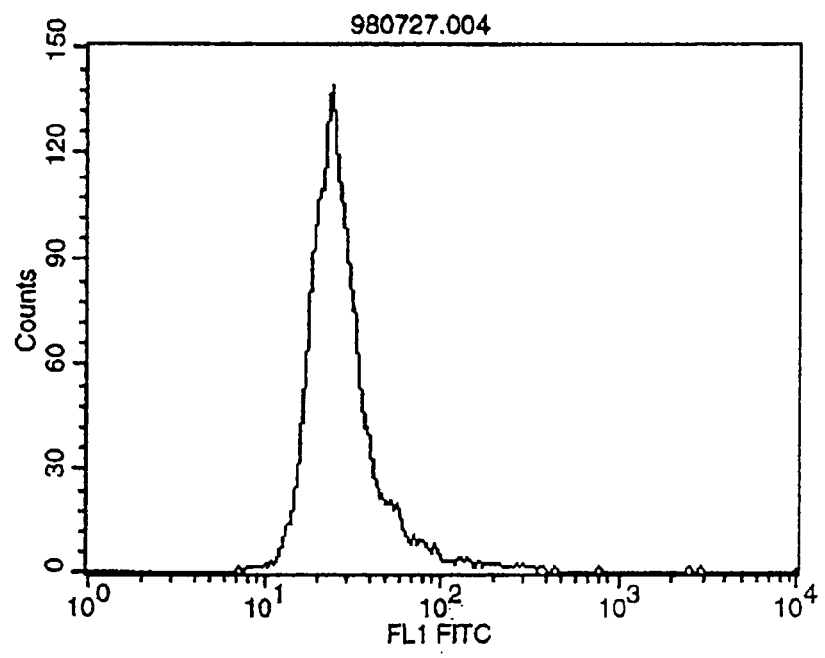
FIG. 1 shows the result of flow cytometry, illustrating that human IgG antibody does not bind to L1210 cells expressing human IAP (hIAP/L1210).
Figure 2:
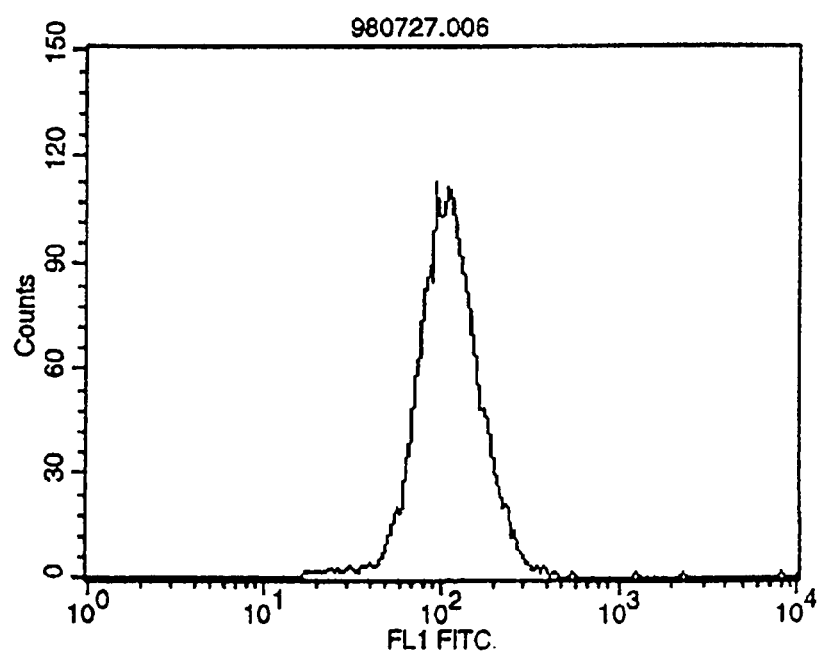
FIG. 2 shows the result of flow cytometry, illustrating that the chimera MABL-1 antibody specifically binds to L1210 cells expressing human IAP (hIAP/L1210).
Figure 3:
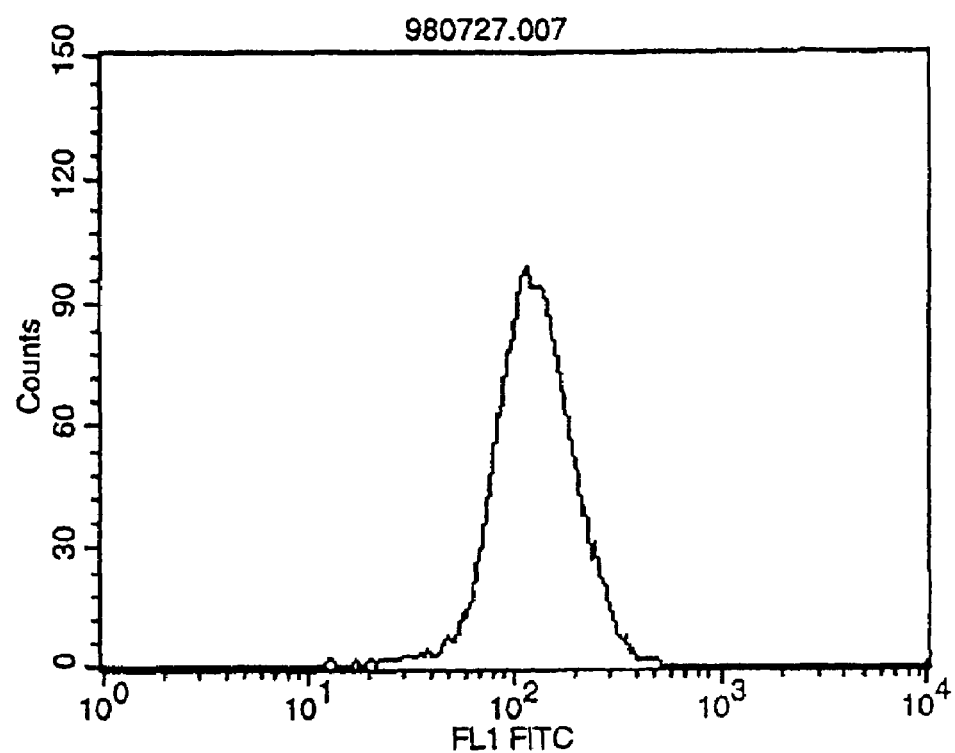
FIG. 3 shows the result of flow cytometry, illustrating that the chimera MABL-2 antibody specifically binds to L1210 cells expressing human IAP (hIAP/L1210).
Figure 4:
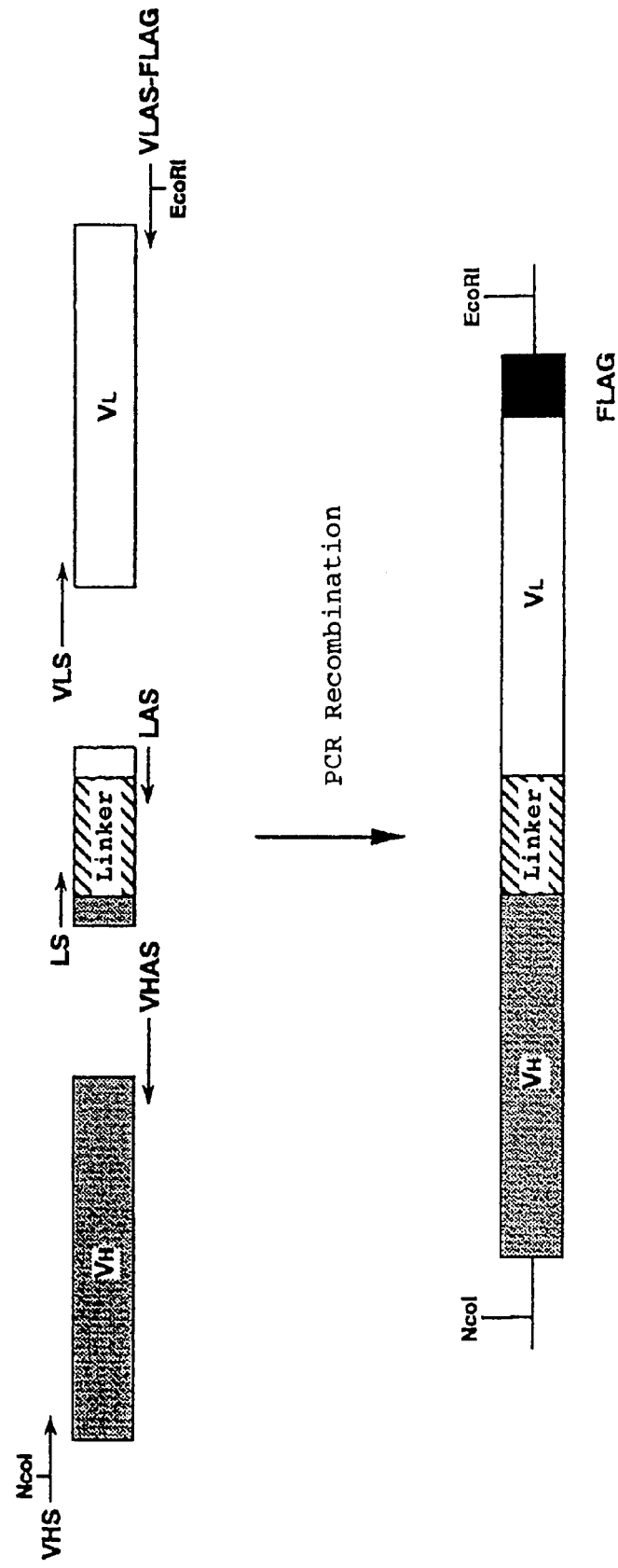
FIG. 4 schematically illustrates the process for producing the single-chain Fv according to the present invention.
Figure 5:
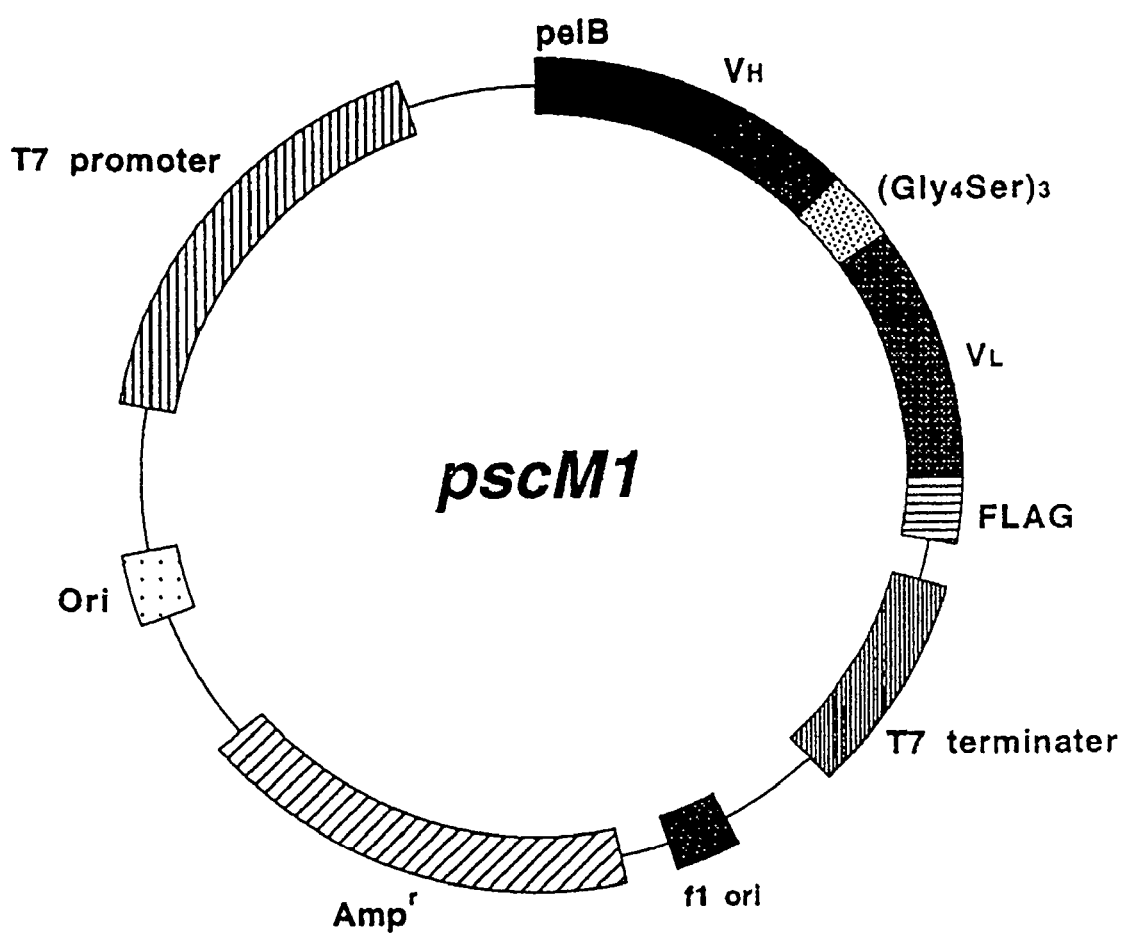
FIG. 5 illustrates a structure of an expression plasmid which can be used to express a DNA encoding the single-chain Fv of the invention in E. coli. The (Gly$_4$Ser)$_3$ linker is shown in SEQ ID NO: 19.
Figure 6:
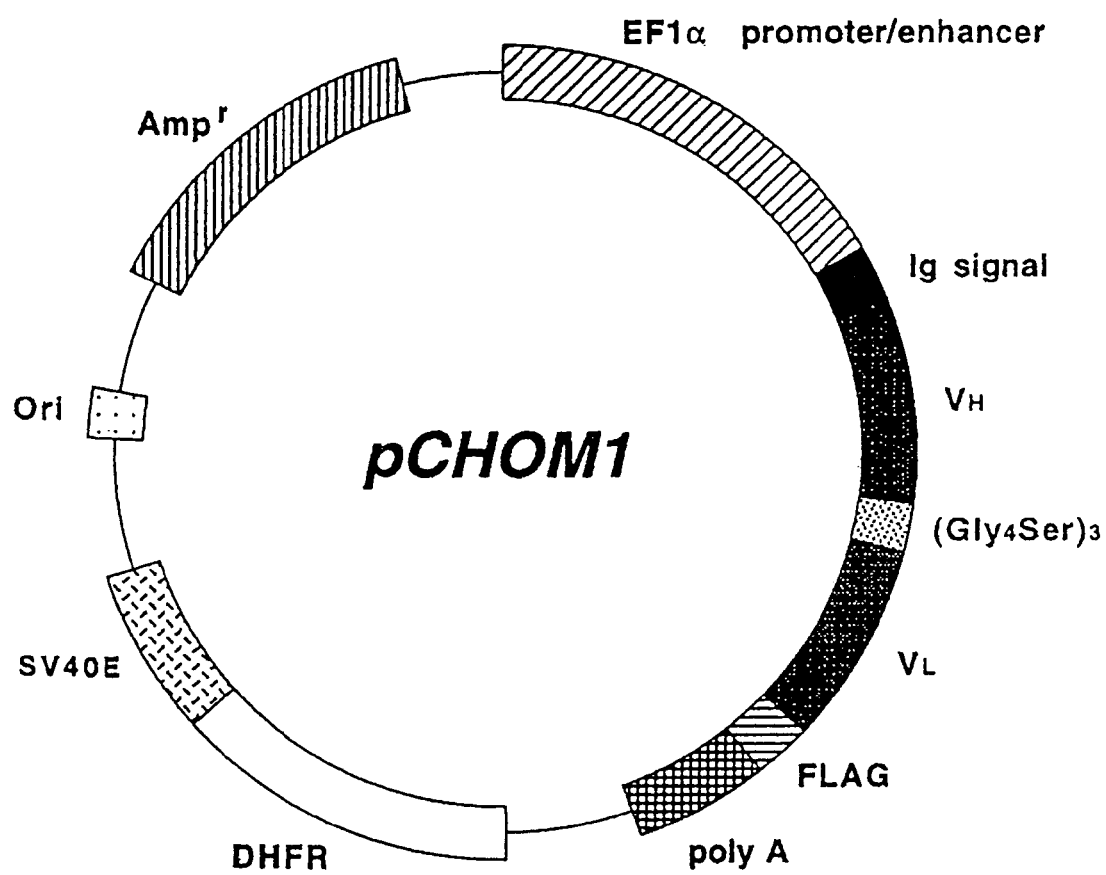
FIG. 6 illustrates a structure of an expression plasmid which is used to express a DNA encoding the single-chain Fv of the invention in mammalian cells. The (Gly$_4$Ser)$_3$ linker is shown in SEQ ID NO: 19.
Figure 7:
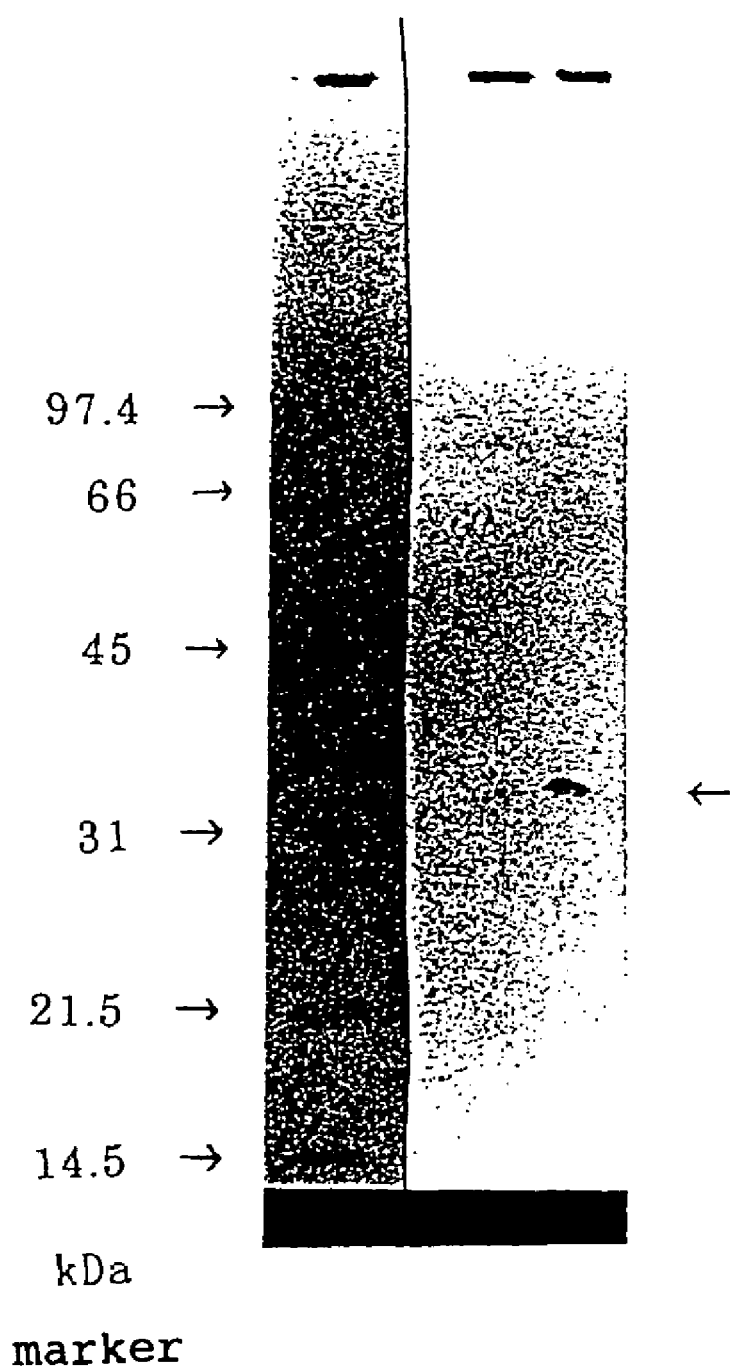
FIG. 7 shows a photograph showing the result of western blotting in Example 5.4. From the left, a molecular weight marker (which indicates 97.4, 66, 45, 31, 21.5 and 14.5 kDa from the top), the culture supernatant of pCHO1-introduced COS7 cells and the culture supernatant of pCHOM2-introduced COS7 cells. It illustrates that the reconstructed single-chain Fv of the antibody MABL-2 (arrow) is contained in the culture supernatant of the pCHOM2-introduced cells.
Figure 8:
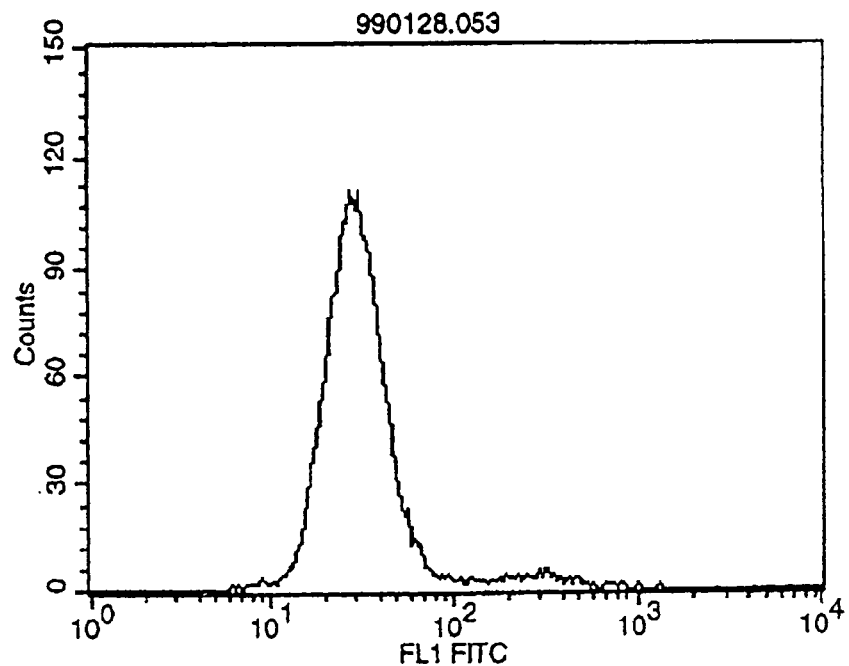
FIG. 8 shows the result of flow cytometry, illustrating that an antibody in the culture supernatant of pCHO1/COS7 cell as a control does not bind to pCOS1/L1210 cell as a control.
Figure 9:
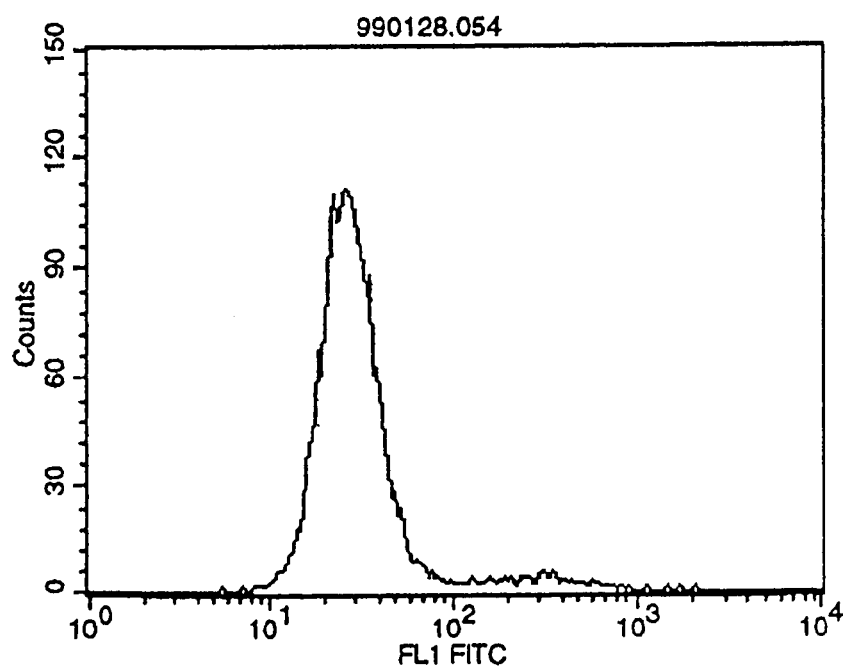
FIG. 9 shows the result of flow cytometry, illustrating that an antibody in the culture supernatant of MABL2-scFv/COS7 cells does not bind to pCOS1/L1210 cells as a control.
Figure 10:
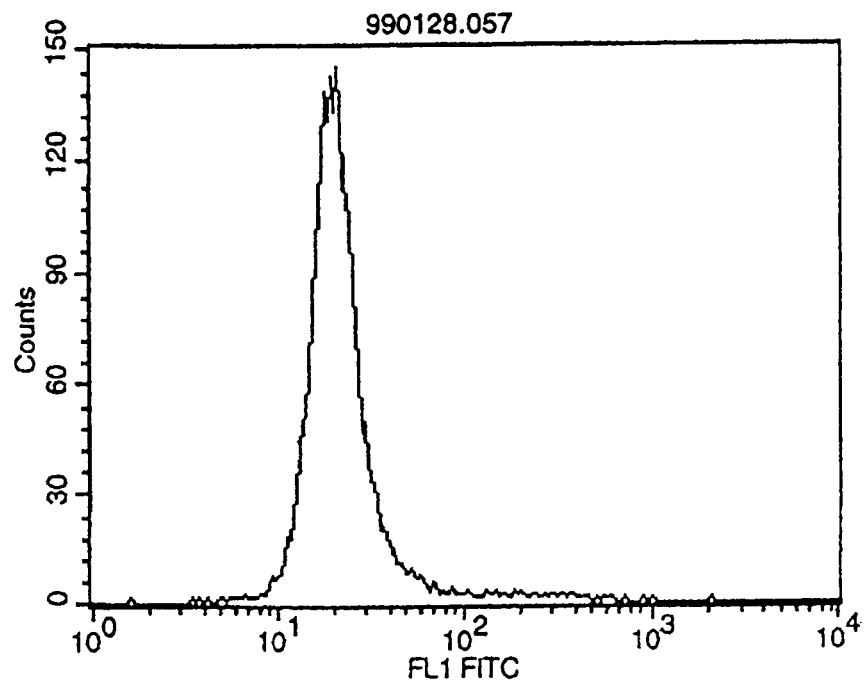
FIG. 10 shows the result of flow cytometry, illustrating that an antibody in the culture supernatant of pCOS1/COS7 cells as a control does not bind to hIAP/L1210 cells.
Figure 11:
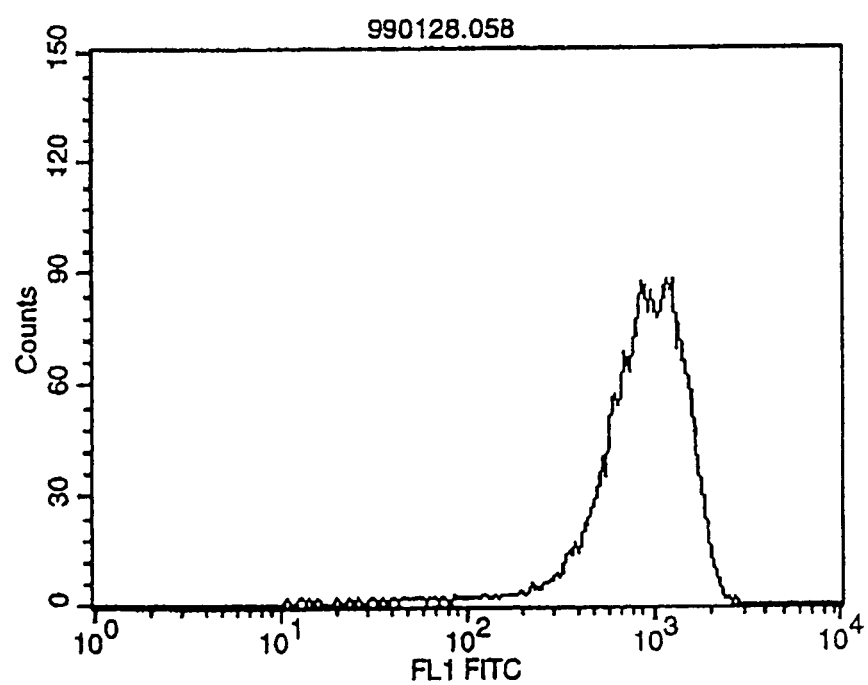
FIG. 11 shows the result of flow cytometry, illustrating that an antibody in the culture supernatant of MABL2-scFv/COS7 cells specifically binds to hIAP/L1210 cells.
Figure 12:
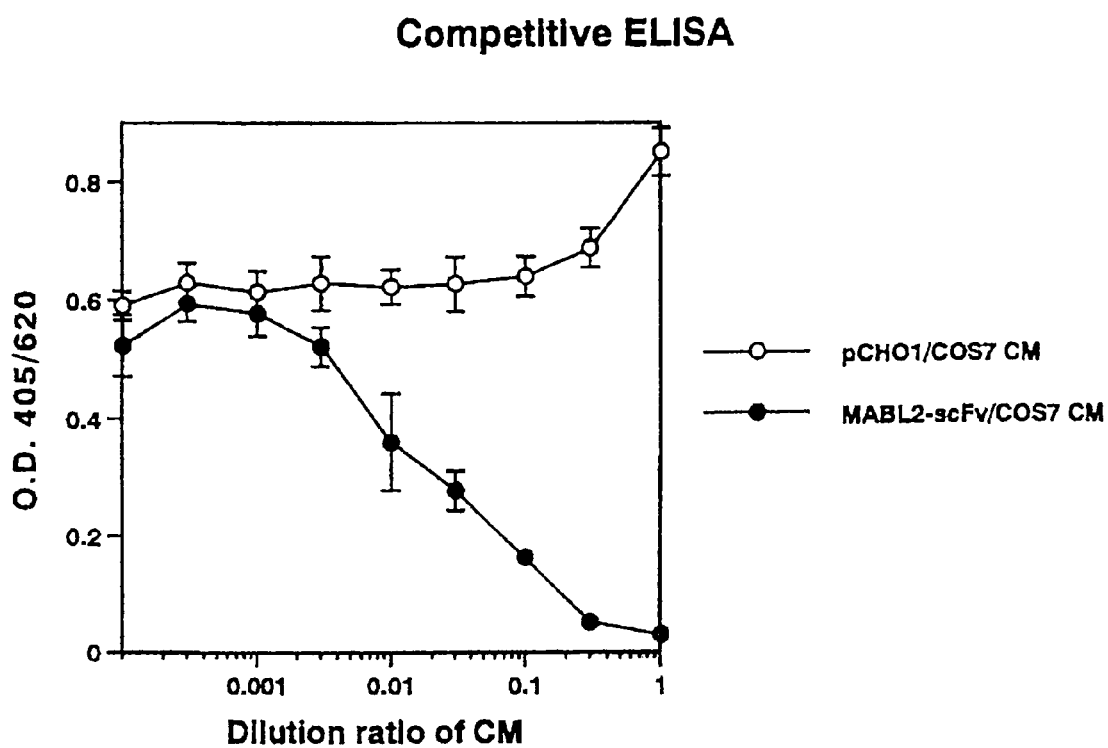
FIG. 12 shows the result of the competitive ELISA in Example 5.6, wherein the binding activity of the single-chain Fv of the invention (MABL2-scFv) to the antigen is demonstrated in terms of the inhibition of binding of the mouse monoclonal antibody MABL-2 to the antigen as an index, in comparison with the culture supernatant of pCHO1/COS7 cells as a control.
Figure 13:
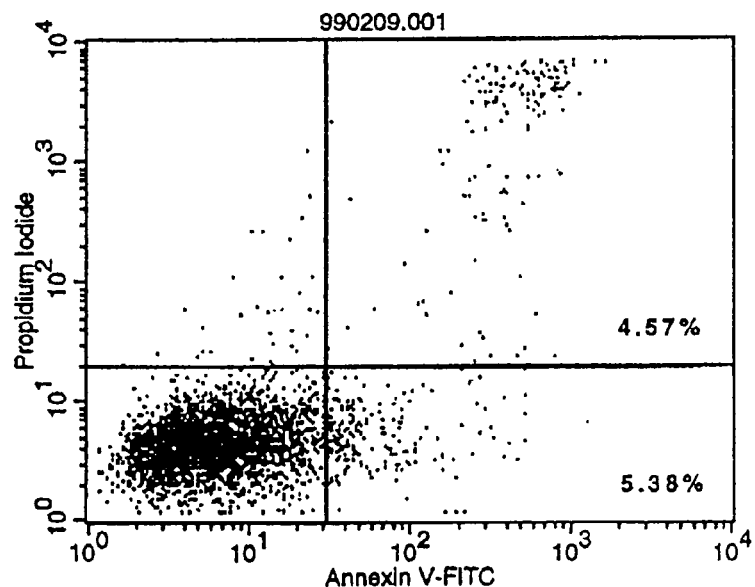
FIG. 13 shows the results of the apoptosis-inducing effect in Example 5.7, illustrating that the antibody in the culture supernatant of pCHO1/COS7 cells as a control does not induce the apoptosis of pCOS1/L1210 cells as a control.
Figure 14:
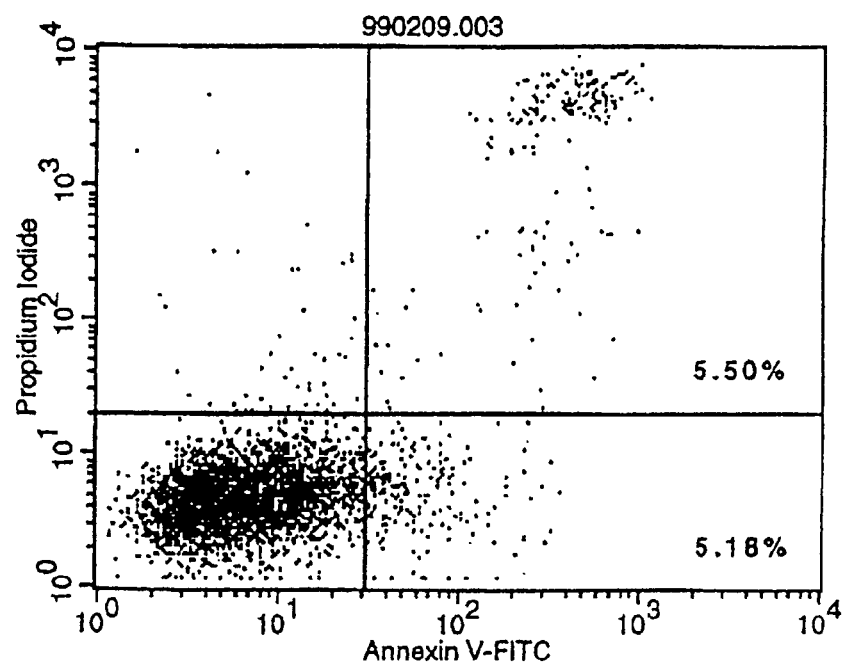
FIG. 14 shows the results of the apoptosis-inducing effect in Example 5.7, illustrating that the antibody in the culture supernatant of MABL2-scFv/COS7 cells does not induce apoptosis of pCOS1/L1210 cells as a control.
Figure 15:
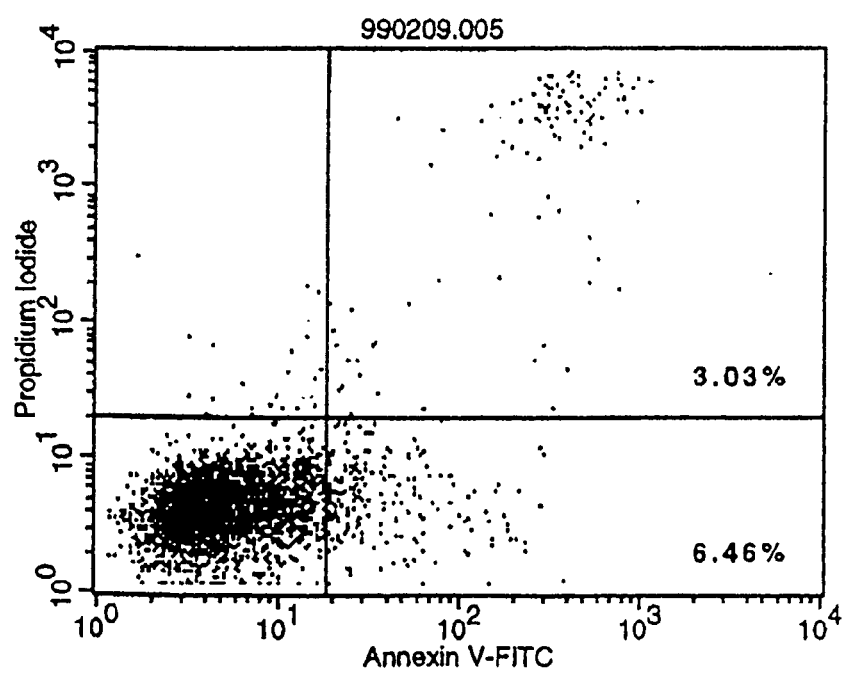
FIG. 15 shows the results of the apoptosis-inducing effect in Example 5.7, illustrating that the antibody in the culture supernatant of pCHO1/COS7 cells as a control does not induce apoptosis of hIAP/L1210 cells.
Figure 16:
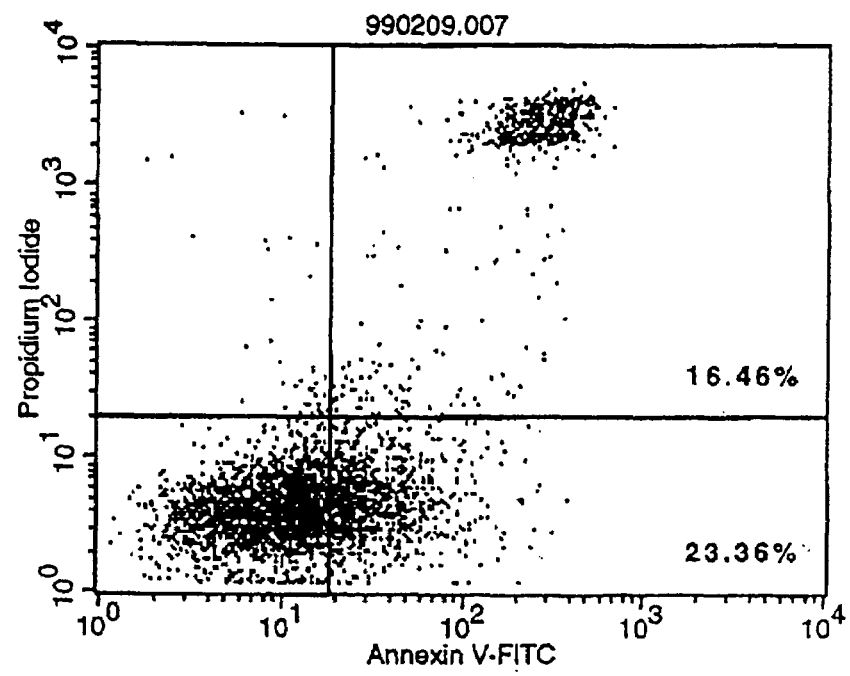
FIG. 16 shows the results of the apoptosis-inducing effect in Example 5.7, illustrating that the antibody in the culture supernatant of MABL2-scFv/COS7 cells specifically induces apoptosis of hIAP/L1210 cells.
Figure 17:
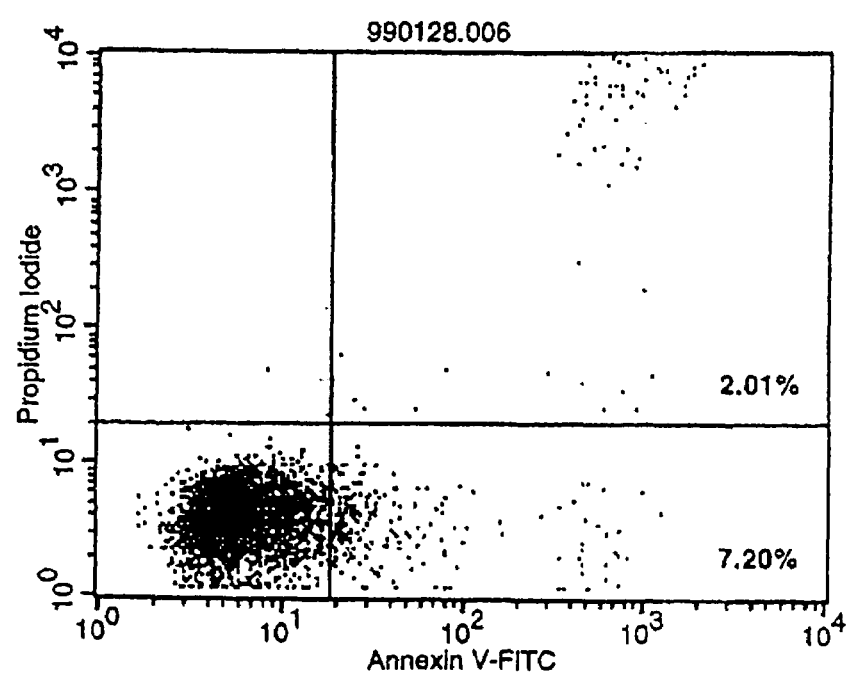
FIG. 17 shows the results of the apoptosis-inducing effect in Example 5.7, illustrating that the antibody in the culture supernatant of pCHO1/COS7 cells as a control does not induce apoptosis of CCRF-CEM cells (at 50% of the final concentration).
Figure 18:
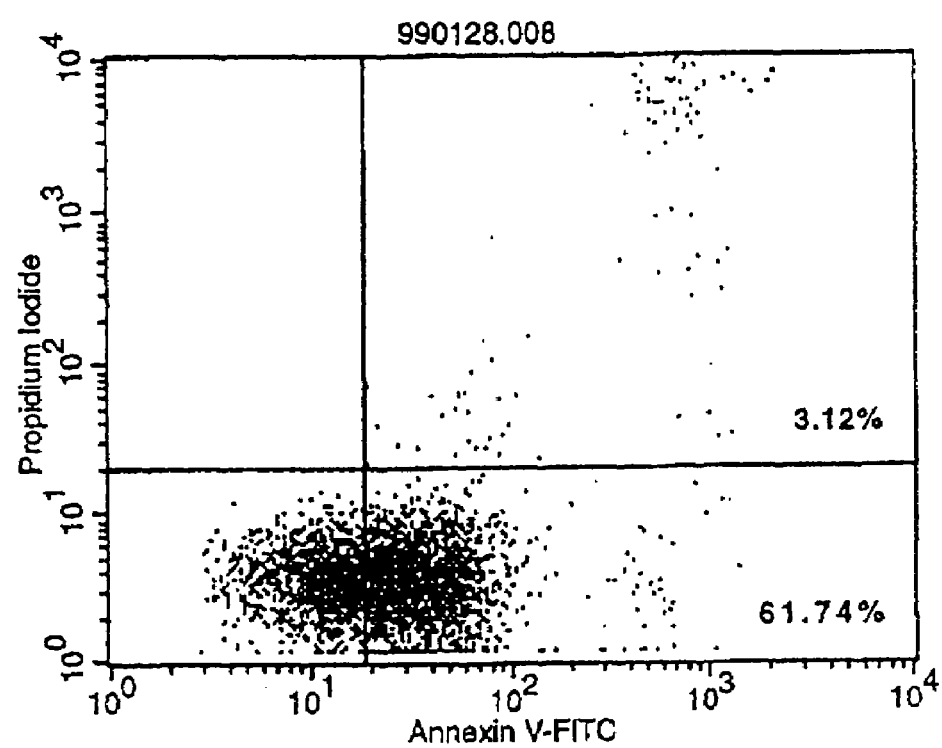
FIG. 18 shows the results of the apoptosis-inducing effect in Example 5.7, illustrating that the antibody in the culture supernatant of MABL2-scFv/COS7 cells specifically induces apoptosis of CCRF-CEM cells (at 50% of the final concentration).
Figure 19:
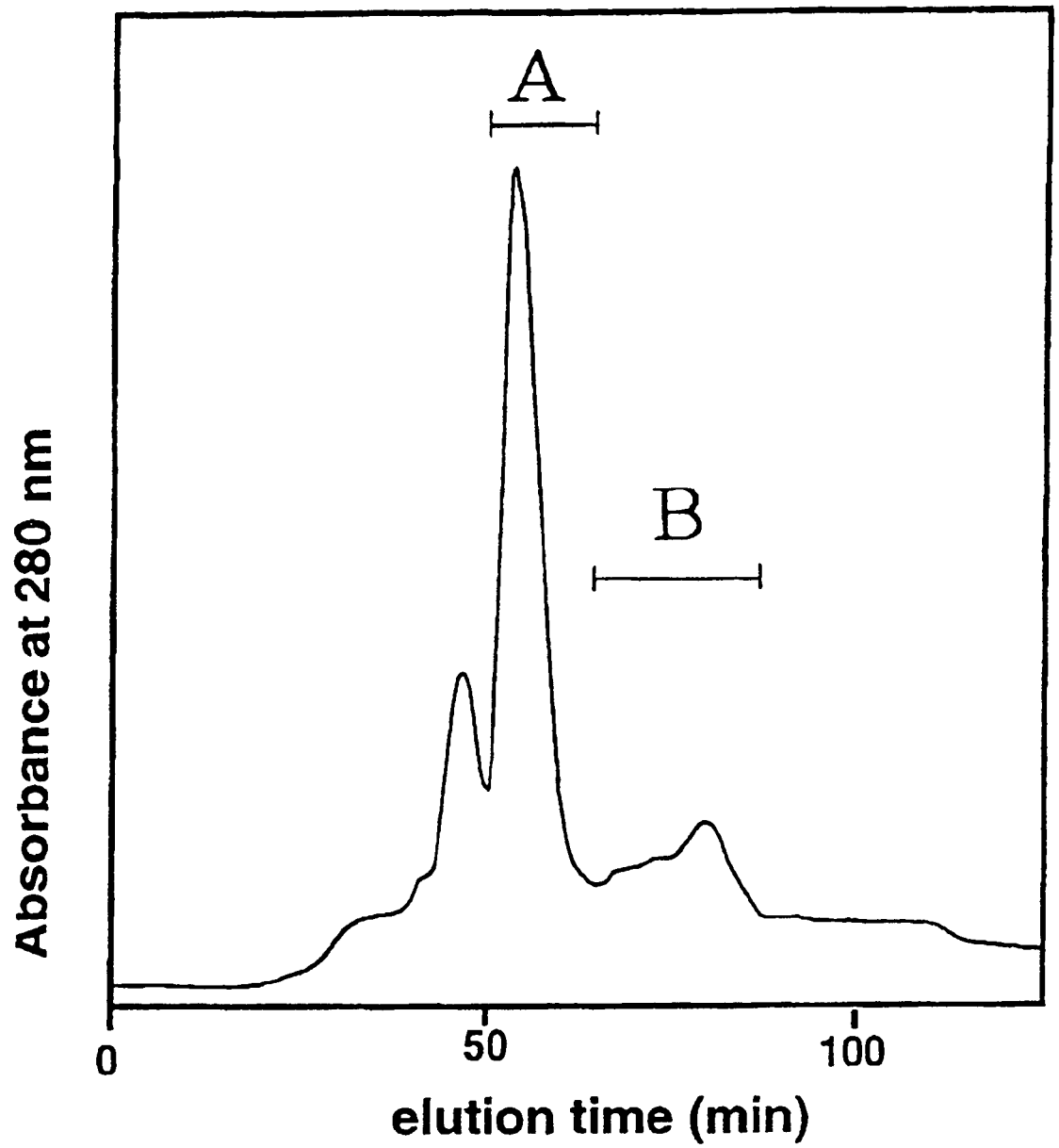
FIG. 19 shows the chromatogram obtained in the purification of the single-chain Fv derived form the antibody MABL-2 produced by the CHO cells in Example 5.9, illustrating that fraction A and fraction B were obtained as the major peaks when the fraction from Blue-sepharose column was purified with hydroxyapatite column.
Figure 20:
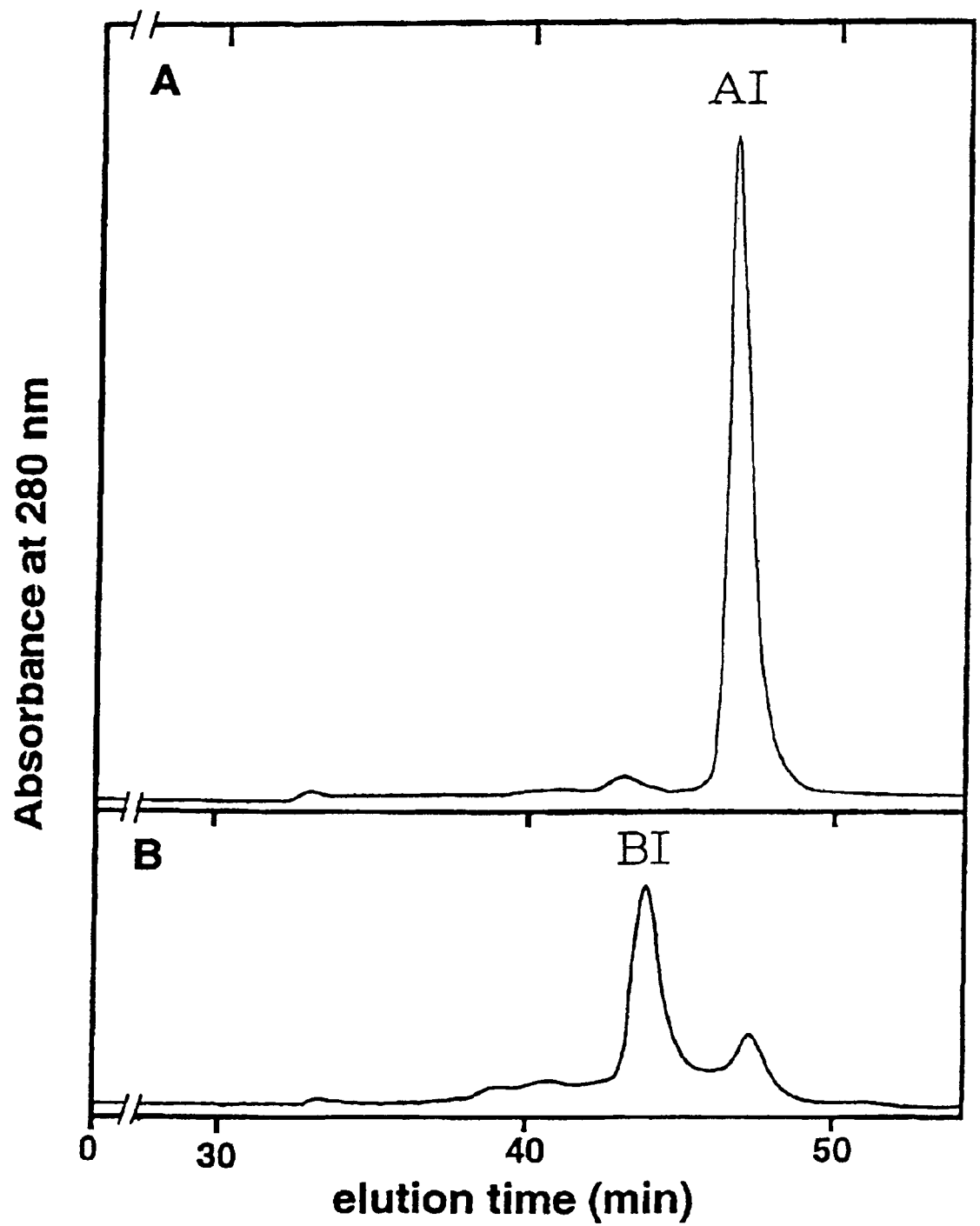
FIG. 20 shows the results of purification by gel filtration of fraction A and fraction B obtained in Example 5.9-(2), illustrating that the major peaks (AI and BI, respectively) were eluted from fraction A at approximately 36 kD of the apparent molecular weight and from fraction B at approximately 76 kD.
Figure 21:
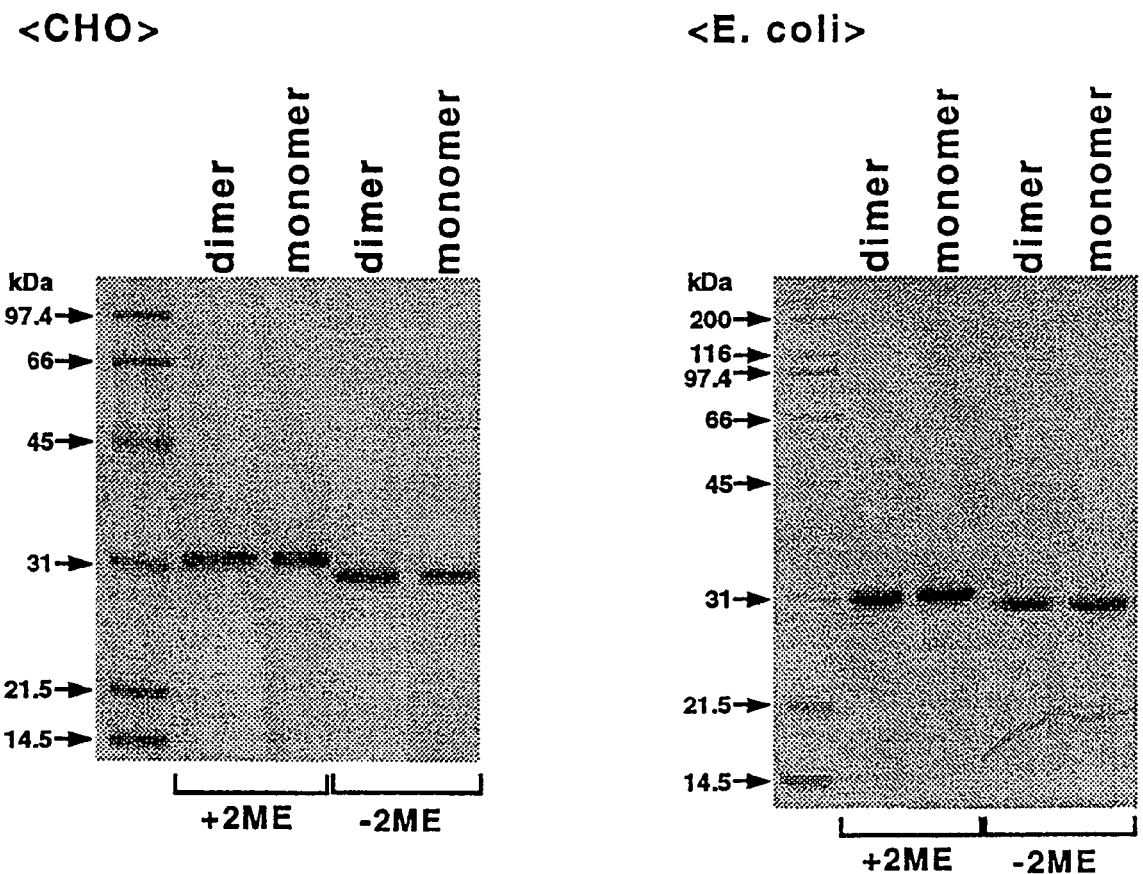
FIG. 21 is the analysis on SDS-PAGE of the fractions obtained in the purification of the single chain Fv derived from the antibody MABL-2 produced by the CHO cells in Example 5.9, illustrating that a single band of approximately 35 kD of molecular weight was observed in both fractions.
Figure 22:
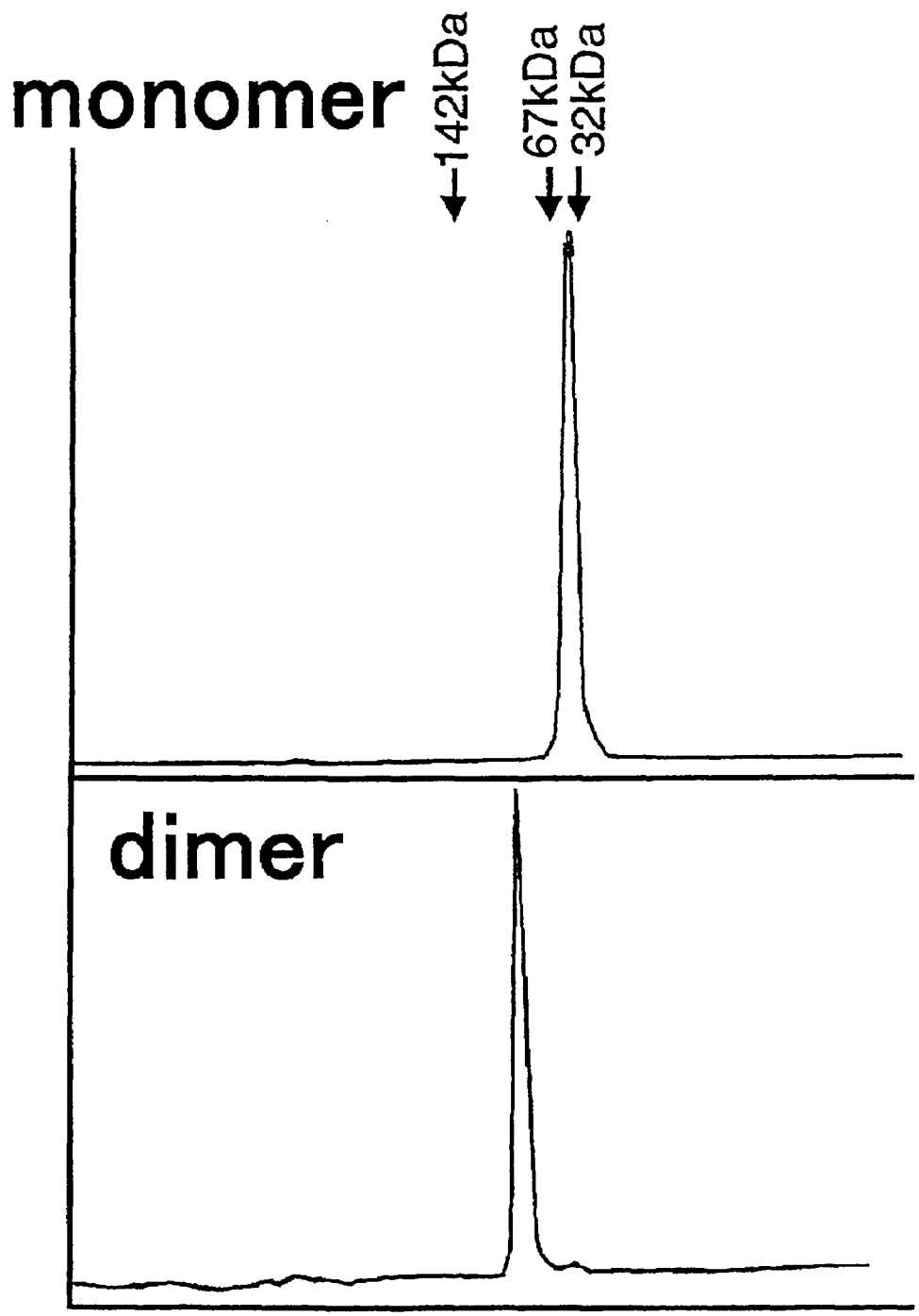
FIG. 22 shows the results of analysis of fractions AI and BI obtained by gel filtration in the purification of the single-chain Fv derived from the antibody MABL-2 produced by the CHO cells, wherein fraction AI comprises monomer and fraction BI comprises dimer.
Figure 23:
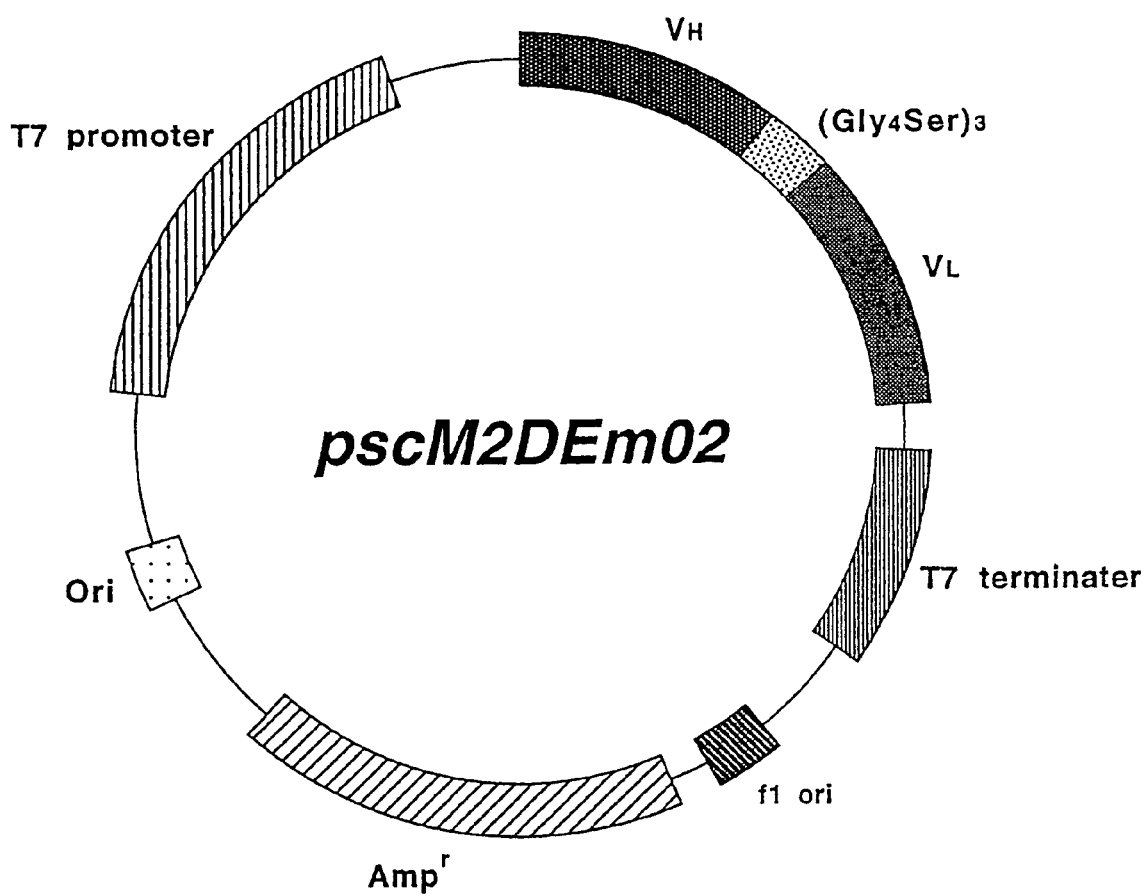
FIG. 23 illustrates a structure of an expression plasmid which can be used to express a DNA encoding the single-chain Fv of the invention in E. coli. The $(Gly_4Ser)_3$ linker is shown in SEQ ID NO: 19.
Figure 24:
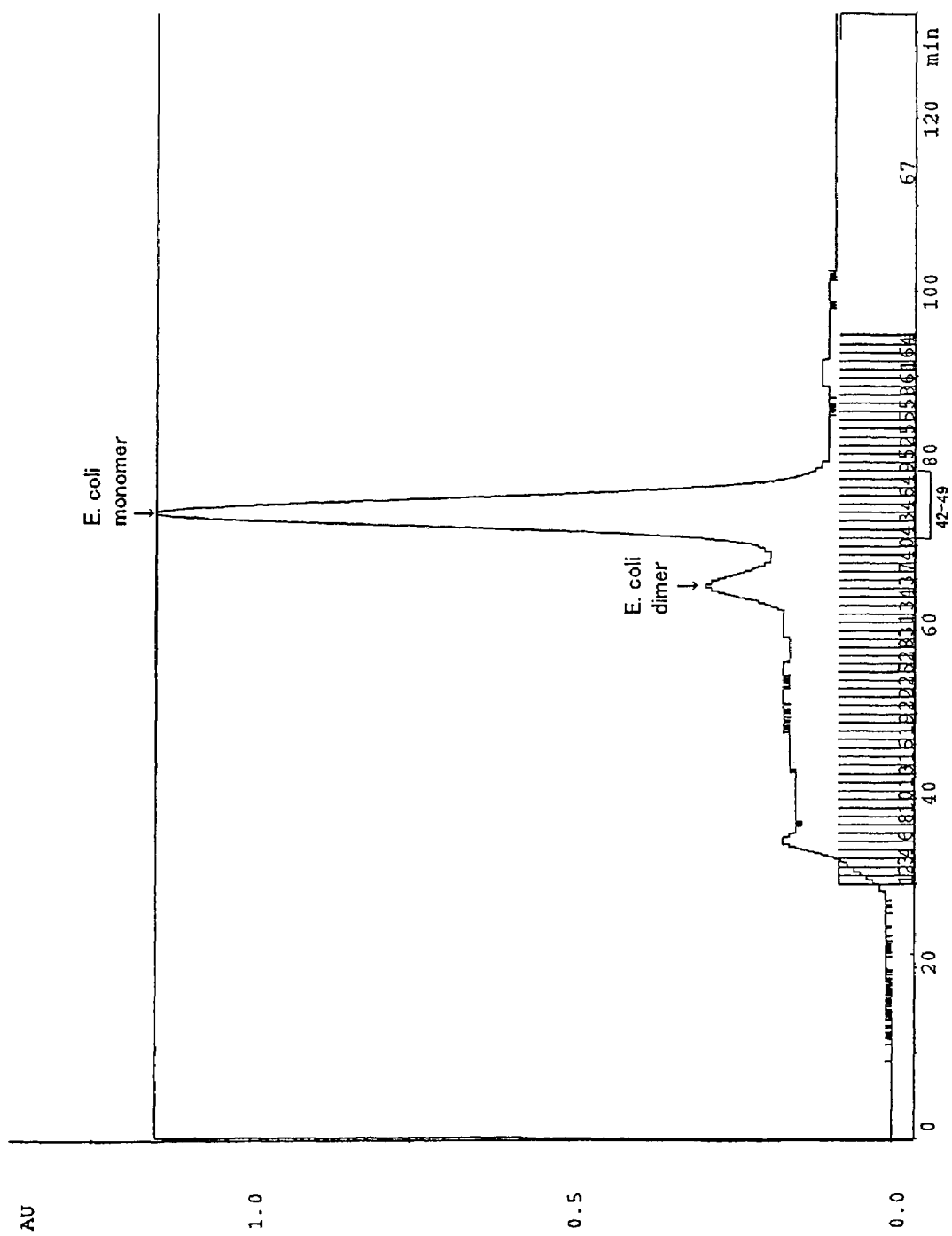
FIG. 24 shows the results of purification on the gel filtration column of crude products of the single-chain Fv polypeptide derived from the antibody MABL-2 produced by E. coli obtained in Example 5.12, wherein each peak indicates monomer or dimer, respectively, of the single-chain Fv produced by E. coli.
Figure 25:
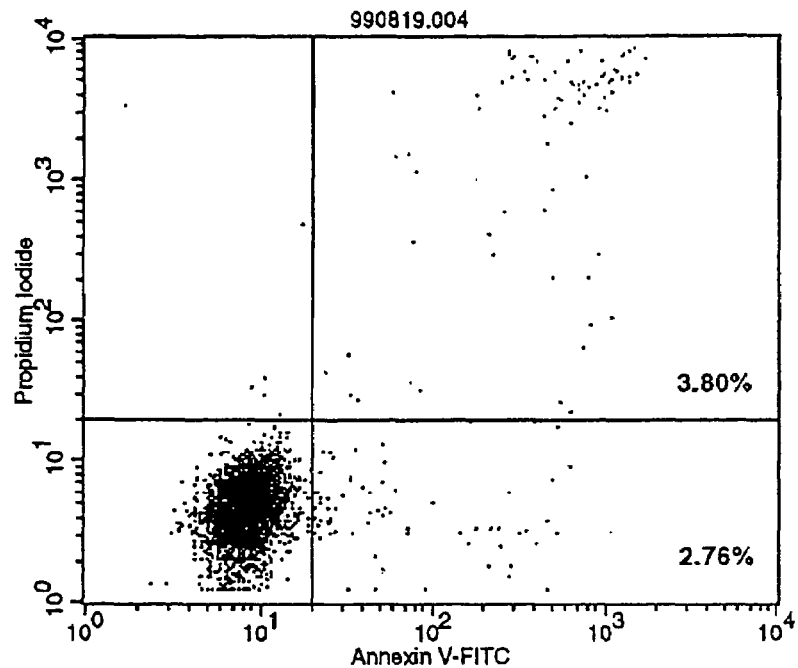
FIG. 25 shows the results of the apoptosis-inducing effect in Example 5.13, illustrating that mouse IgG antibody as a control does not induce apoptosis of hIAP/L1210 cells (the final concentration of 3 μg/ml).
Figure 26:
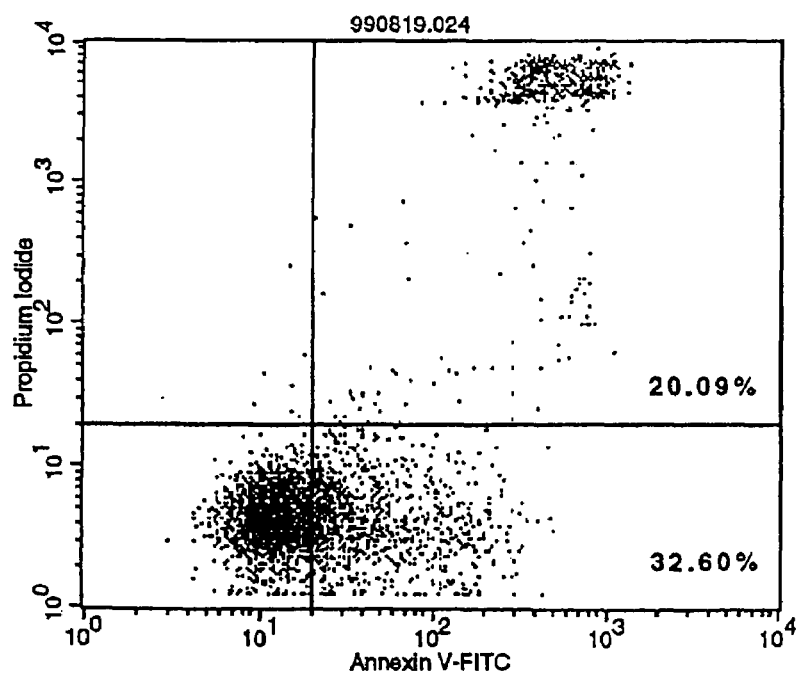
FIG. 26 shows the results of the apoptosis-inducing effect in Example 5.13, illustrating that the dimer of MABL2-scFv produced by the CHO cells remarkably induces apoptosis of hIAP/L1210 cells (the final concentration of 3 μg/ml).
Figure 27:
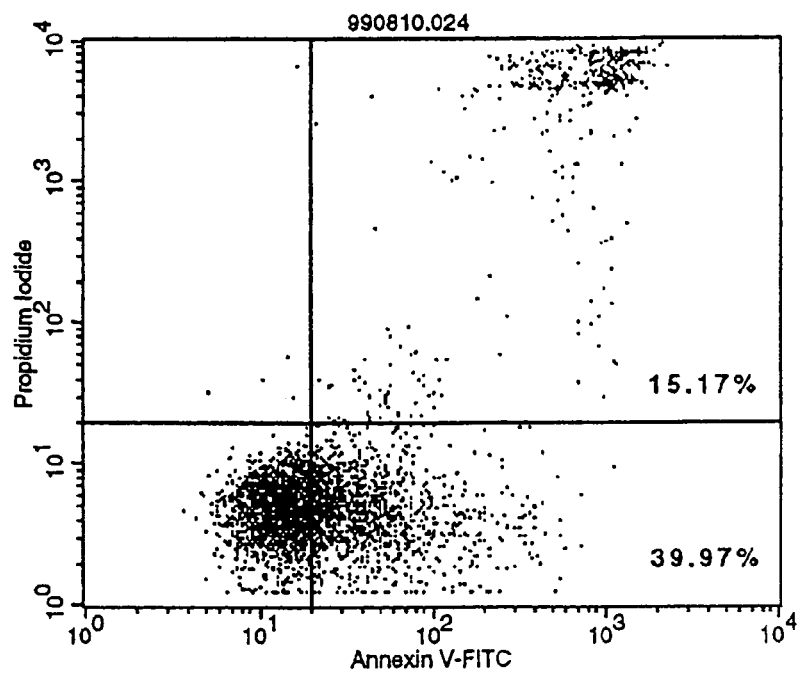
FIG. 27 shows the results of the apoptosis-inducing effect in Example 5.13, illustrating that the dimer of MABL2-scFv produced by E. coli remarkably induces apoptosis of hIAP/L1210 cells (the final concentration of 3 μg/ml).
Figure 28:
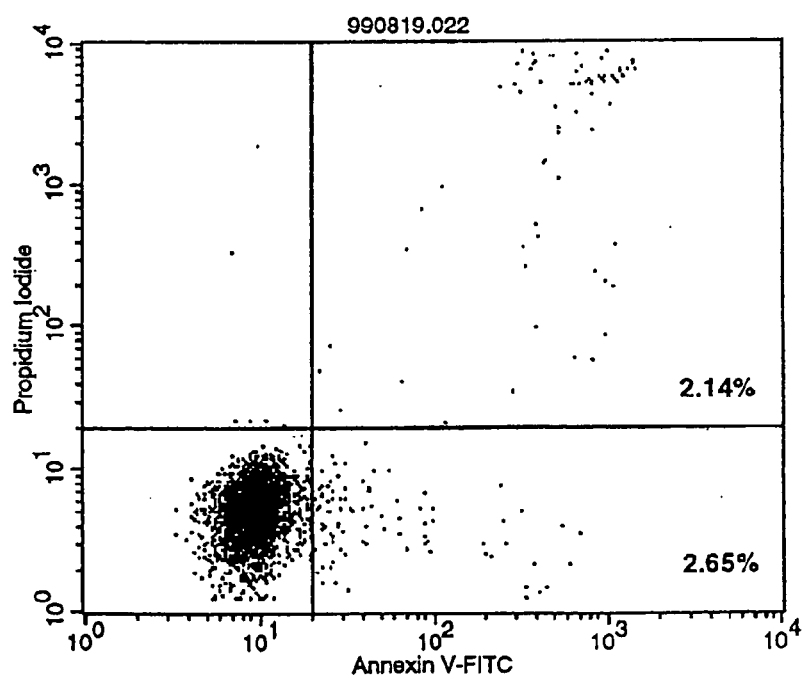
FIG. 28 shows the results of the apoptosis-inducing effect in Example 5.13, illustrating that apoptosis induction to hIAP/L1210 cells by the MABL2-scFv monomer produced by the CHO cells is the same level as that of the control (the final concentration of 3 μg/ml).
Figure 29:
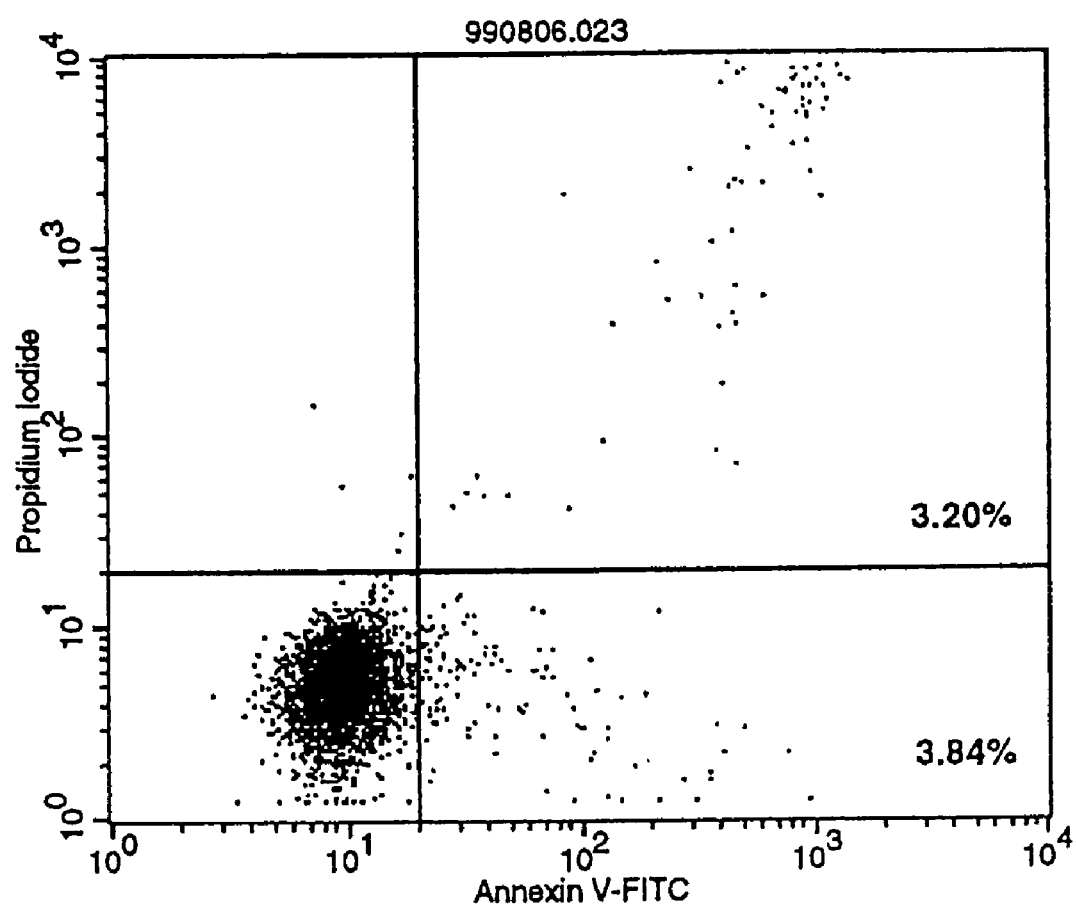
FIG. 29 shows the results of the apoptosis-inducing effect in Example 5.13, illustrating that apoptosis induction to hIAP/L1210 cells of the MABL2-scFv monomer produced by E. coli is the same level as that of control (the final concentration of 3 μg/ml).
Figure 30:
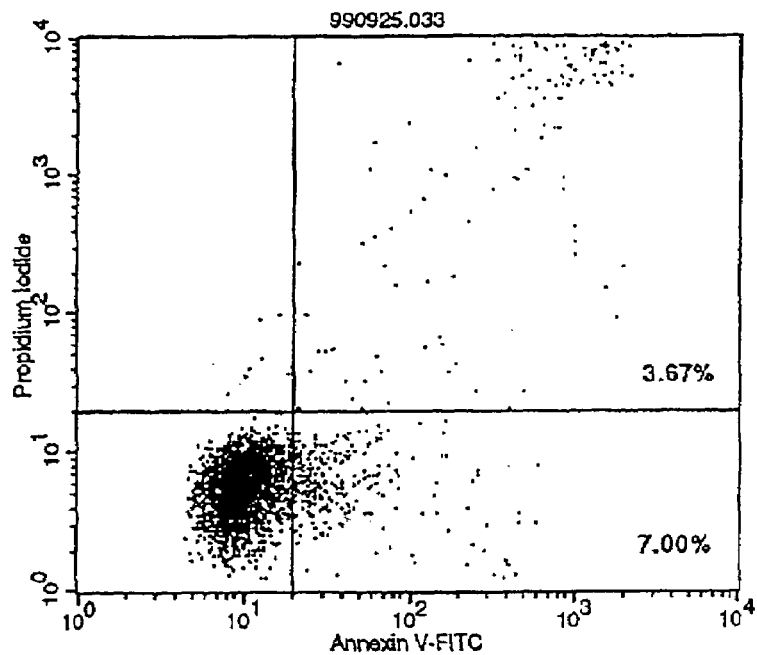
FIG. 30 shows the results of the apoptosis-inducing effect in Example 5.13, illustrating that mouse IgG antibody used as a control does not induce apoptosis of hIAP/L1210 cells even when anti-FLAG antibody is added (the final concentration of 3 μg/ml).
Figure 31:
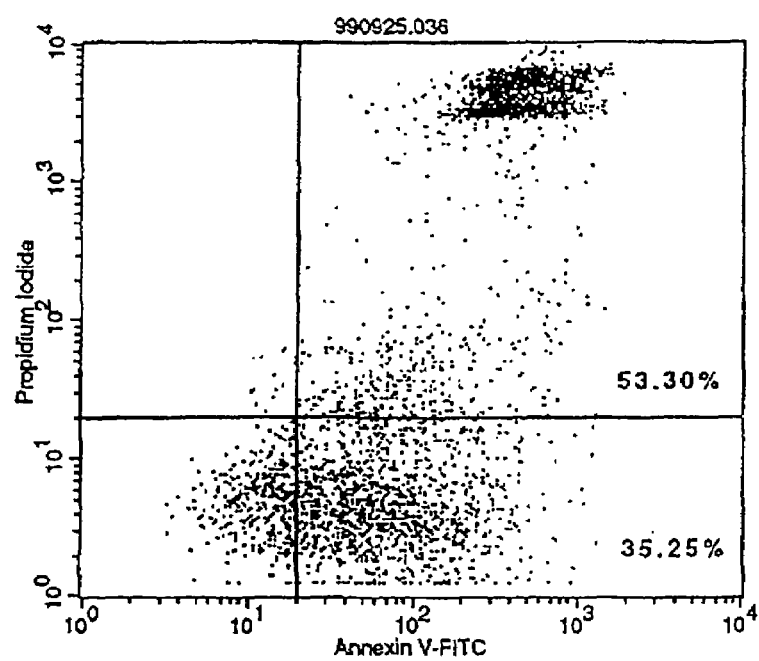
FIG. 31 shows the results of the apoptosis-inducing effect in Example 5.13, illustrating that MABL2-scFv monomer produced by the CHO cells remarkably induces apoptosis of hIAP/L1210 cells when anti-FLAG antibody is added (the final concentration of 3 μg/ml).
Figure 32:
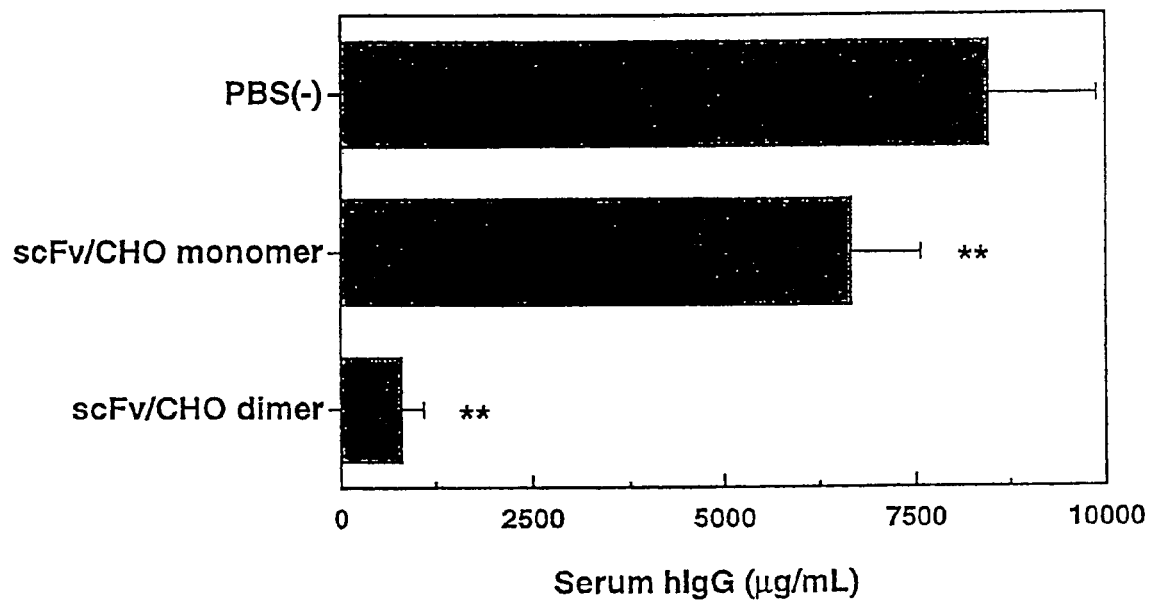
FIG. 32 shows the results of quantitative measurement of human IgG in the serum of a human myeloma cell line KPMM2-transplanted mouse, indicating amounts of human IgG produced by the human myeloma cells in the mouse. It illustrates that the dimer of scFv/CHO remarkably inhibited growth of the KPMM2 cells.
Figure 33:
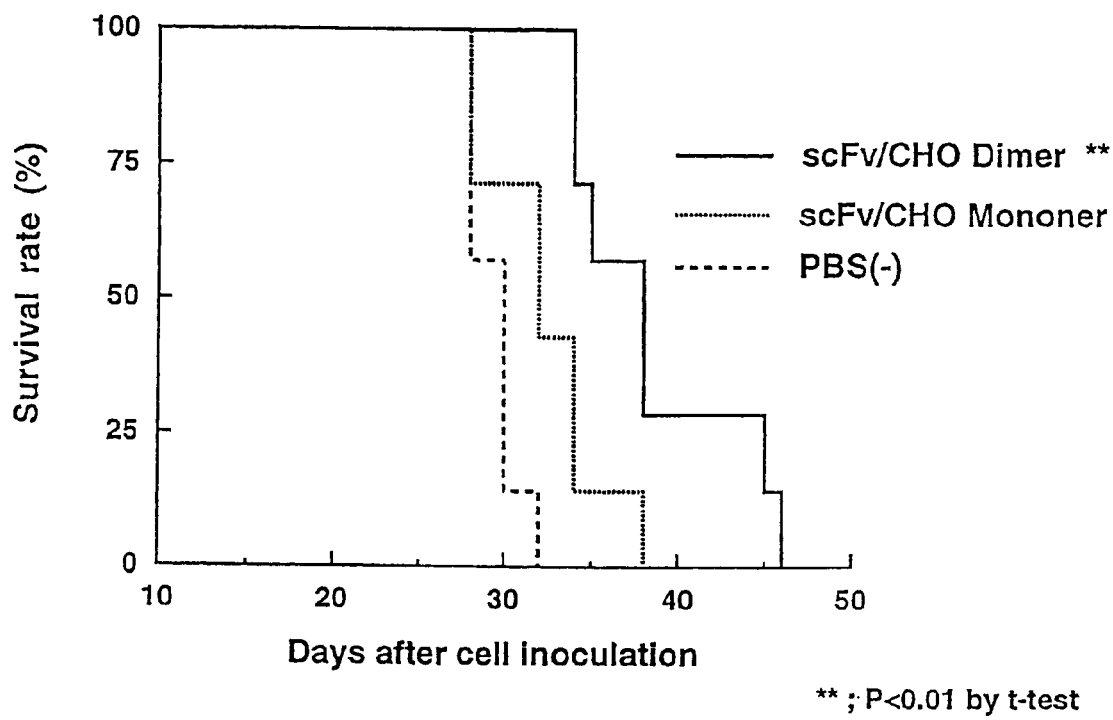
FIG. 33 shows the survival time of the mouse after the transplantation of tumor, illustrating that the scFv/CHO dimer-administered group elongated remarkably the survival time.
Figure 34:
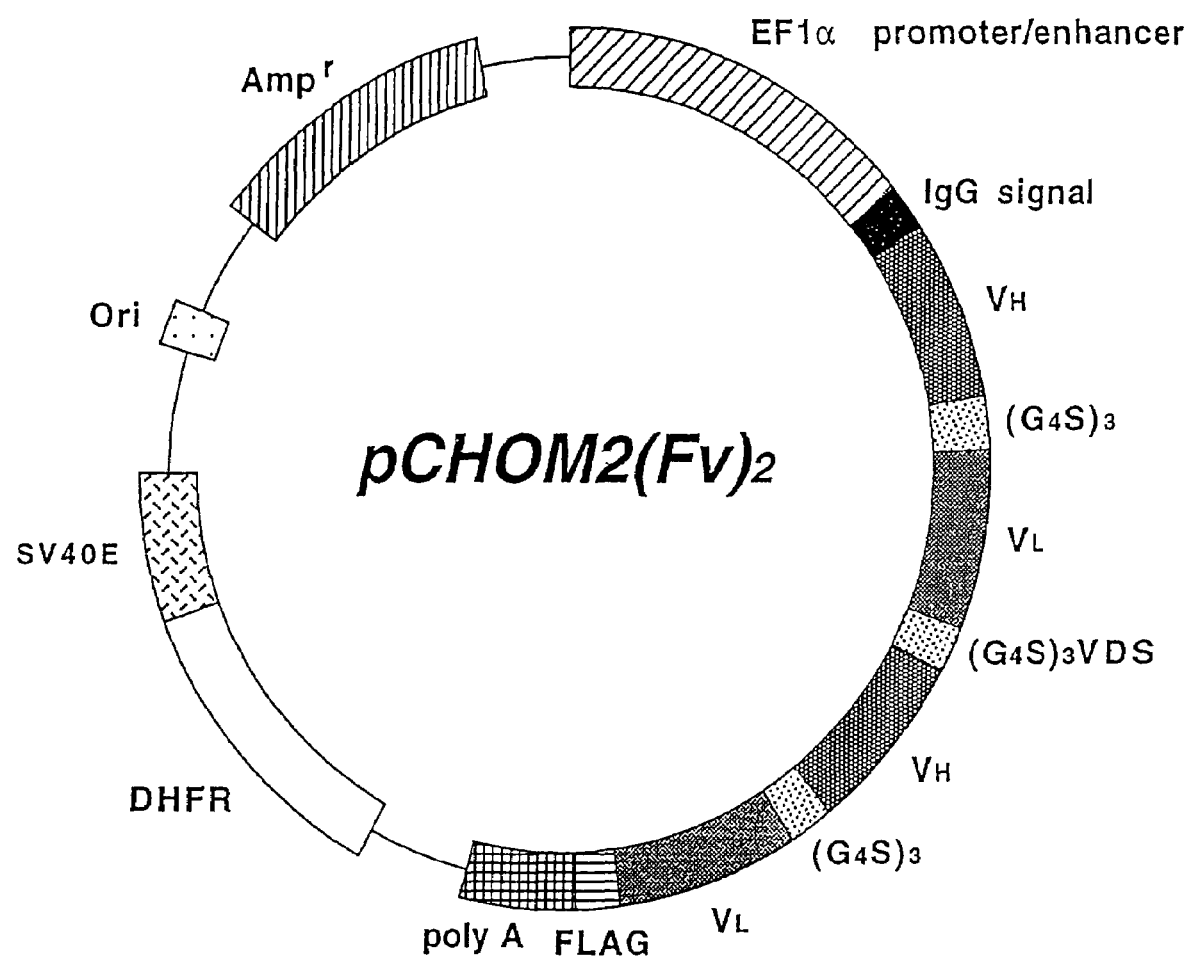
FIG. 34 illustrates a structure of an expression plasmid which expresses a reconstructed polypeptide comprising two H chain V regions and two L chain V regions derived from the antibody MABL-2. The $(Gly_4Ser)_3$ linker is shown in SEQ ID NO: 19 and the $(Gly_4Ser)_3$VSD linker is shown in SEQ ID NO: 55.
Figure 35:
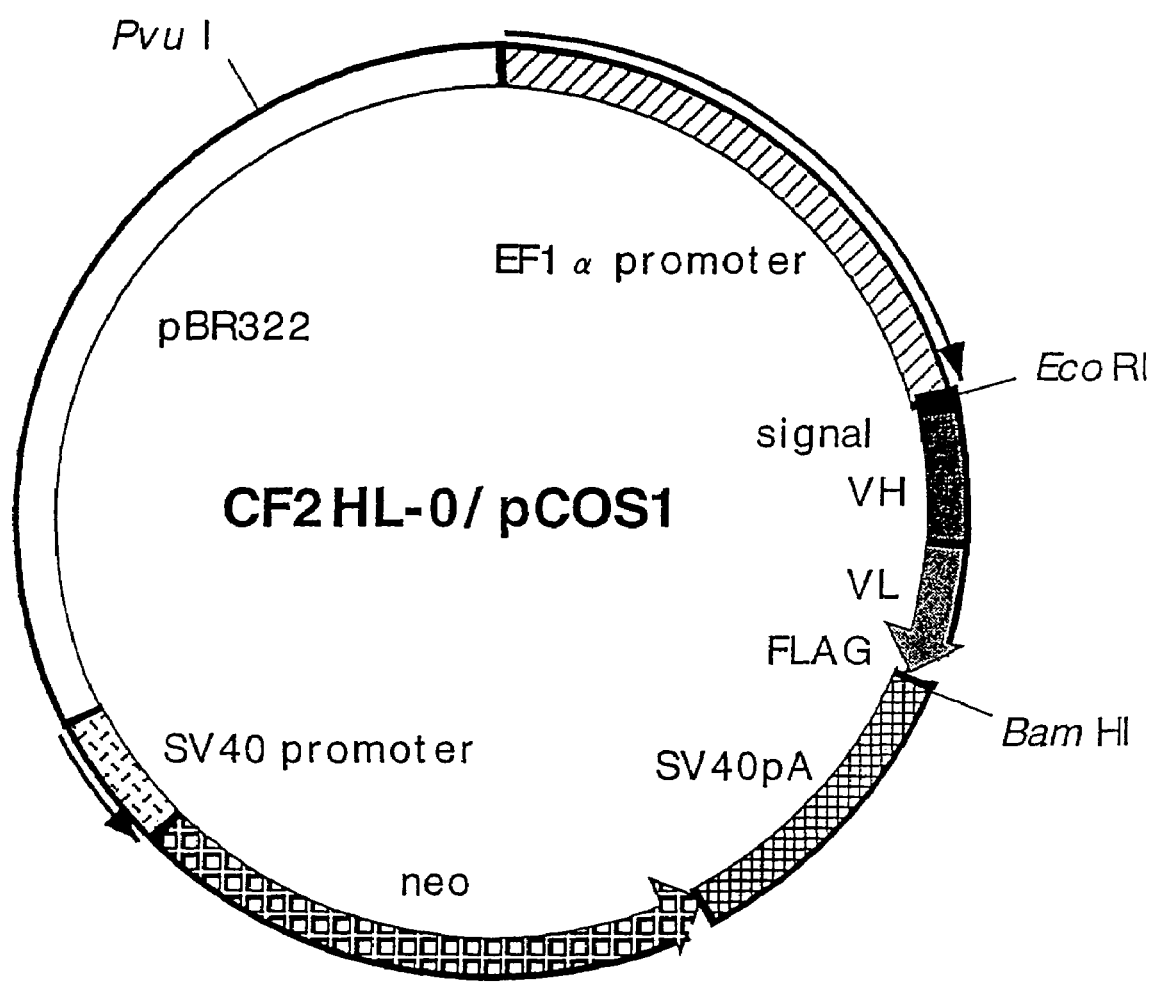
FIG. 35 illustrates a structure of a plasmid which expresses a scFv (HL type) wherein the V regions are linked in the manner of [H chain]-[L chain] without a peptide linker.
Figure 37:
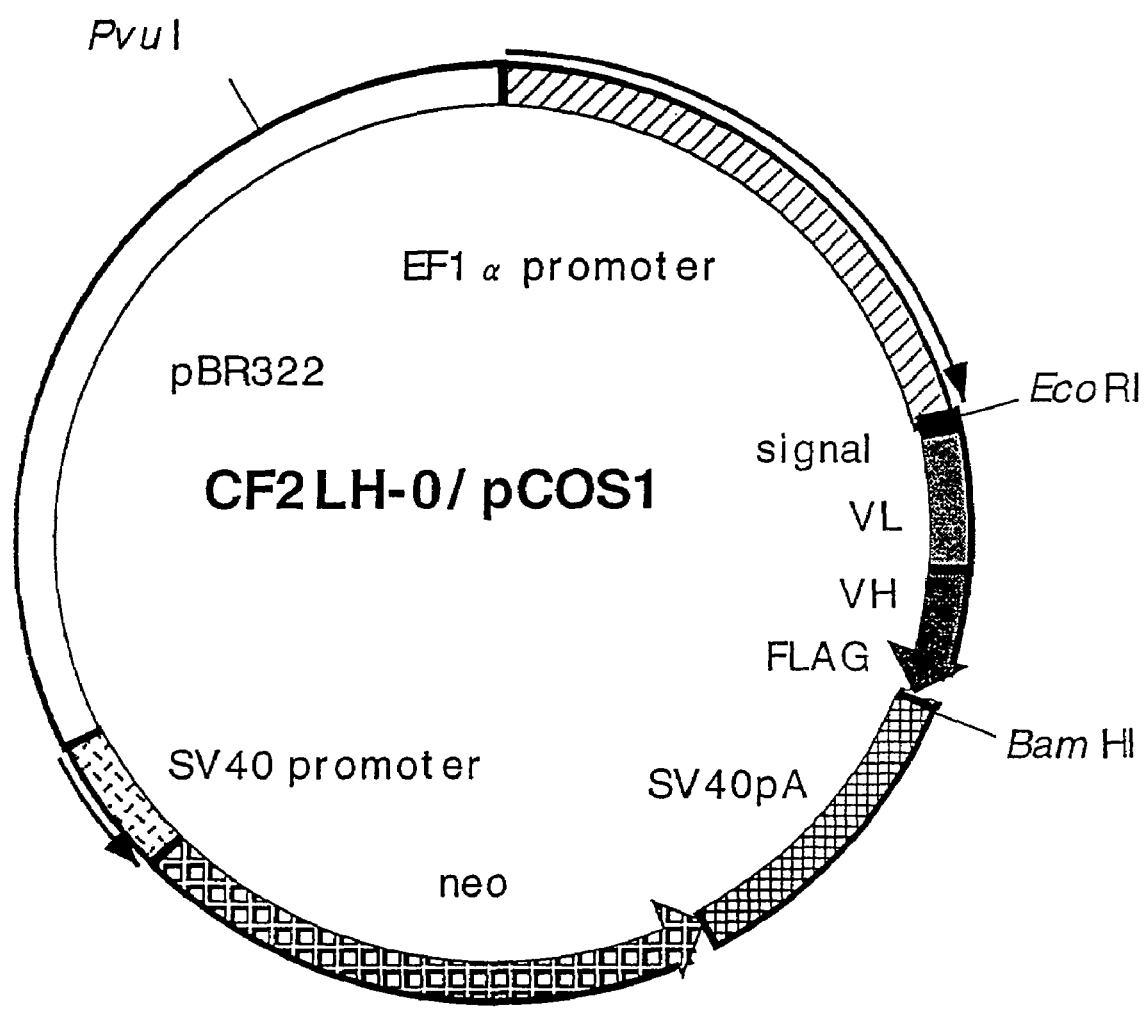
FIG. 37 illustrates a structure of a plasmid which expresses a scFv (LH type) wherein the V regions are linked in the manner of [L chain]-[H chain] without a peptide linker.
Figure 39:
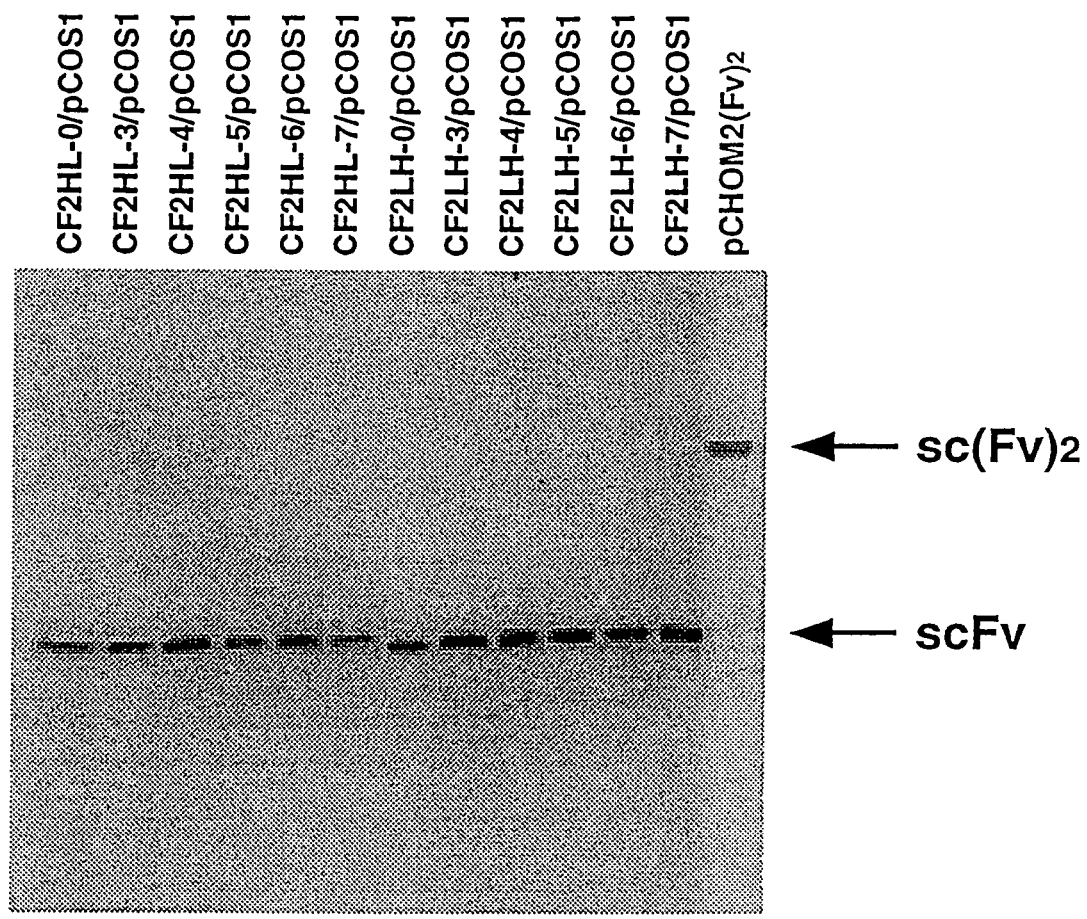
FIG. 39 shows the results of the western blotting in Example 6.4, illustrating that the reconstructed polypeptide sc(FV)$_2$ comprising two H chain V regions and two L chain V regions, and the MABL2-scFv having peptide linkers with different length are expressed.
Figure 40A:
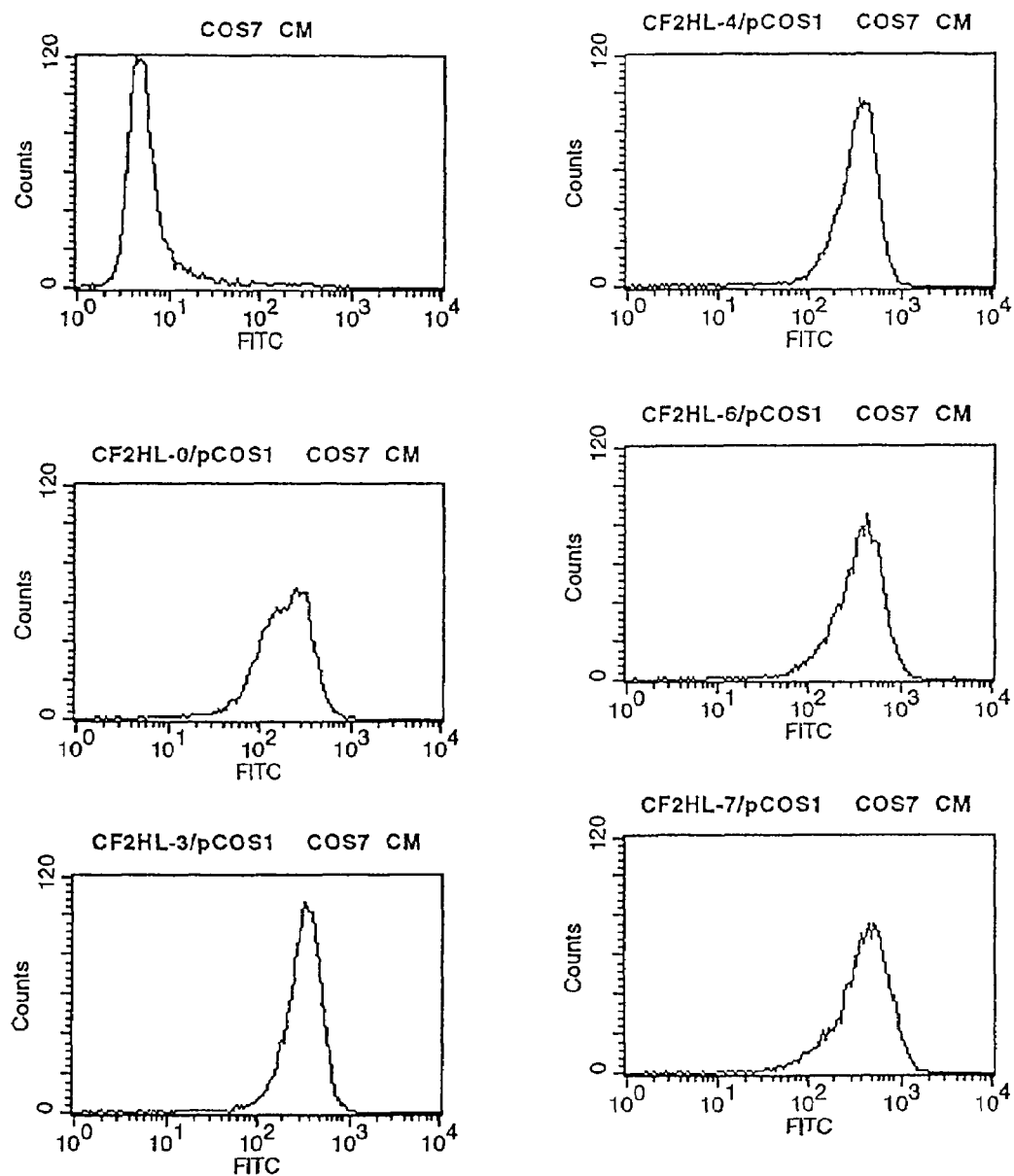
FIGS. 40a and 40b show the results of flow cytometry using the culture supernatant of COS7 cells prepared in Example 6.3 (1), illustrating that the MABL2-scFv and sc(Fv)$_2$ having peptide linkers with different length have high affinities against human IAP.
Figure 40B:
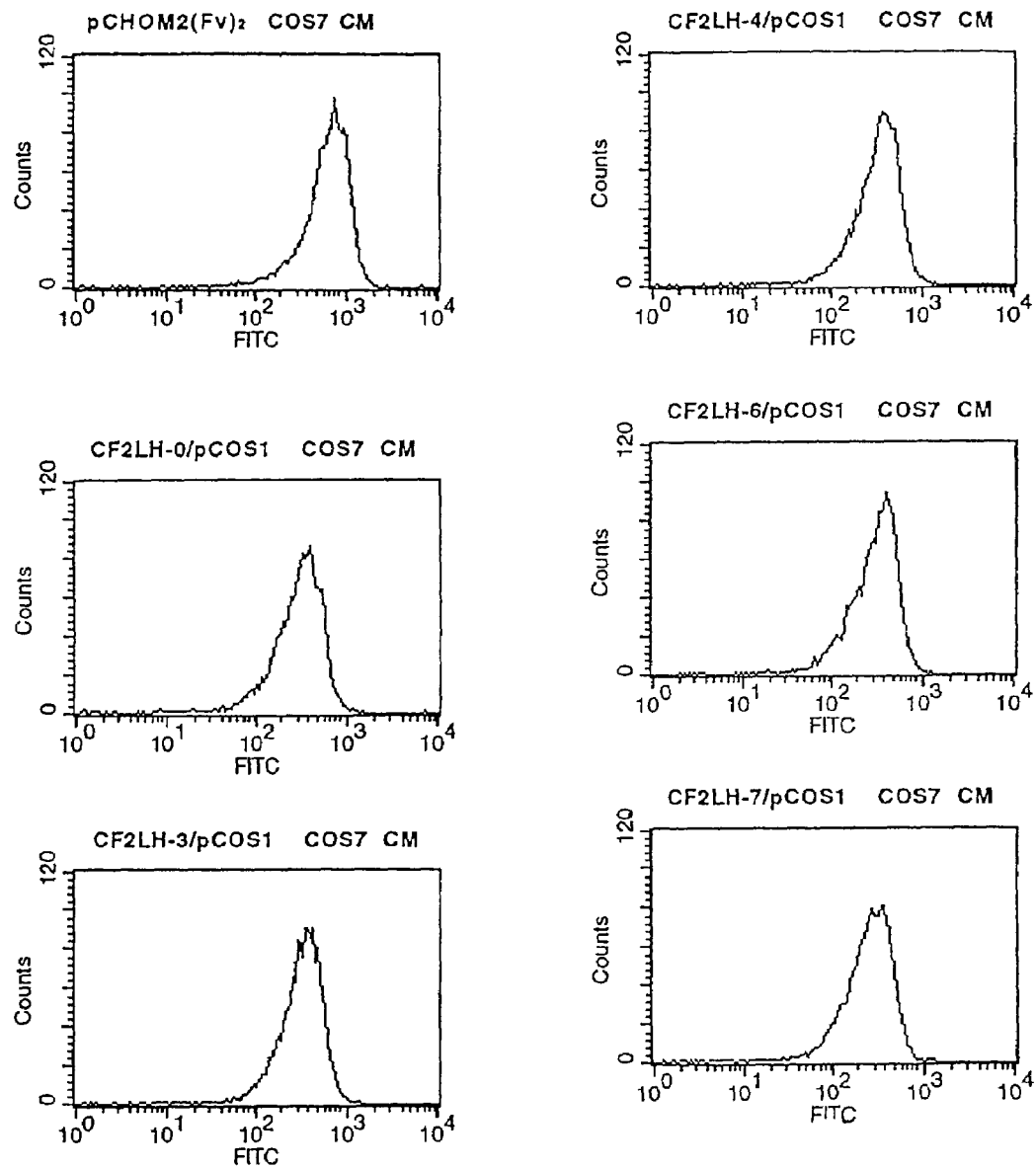
Figure 41:
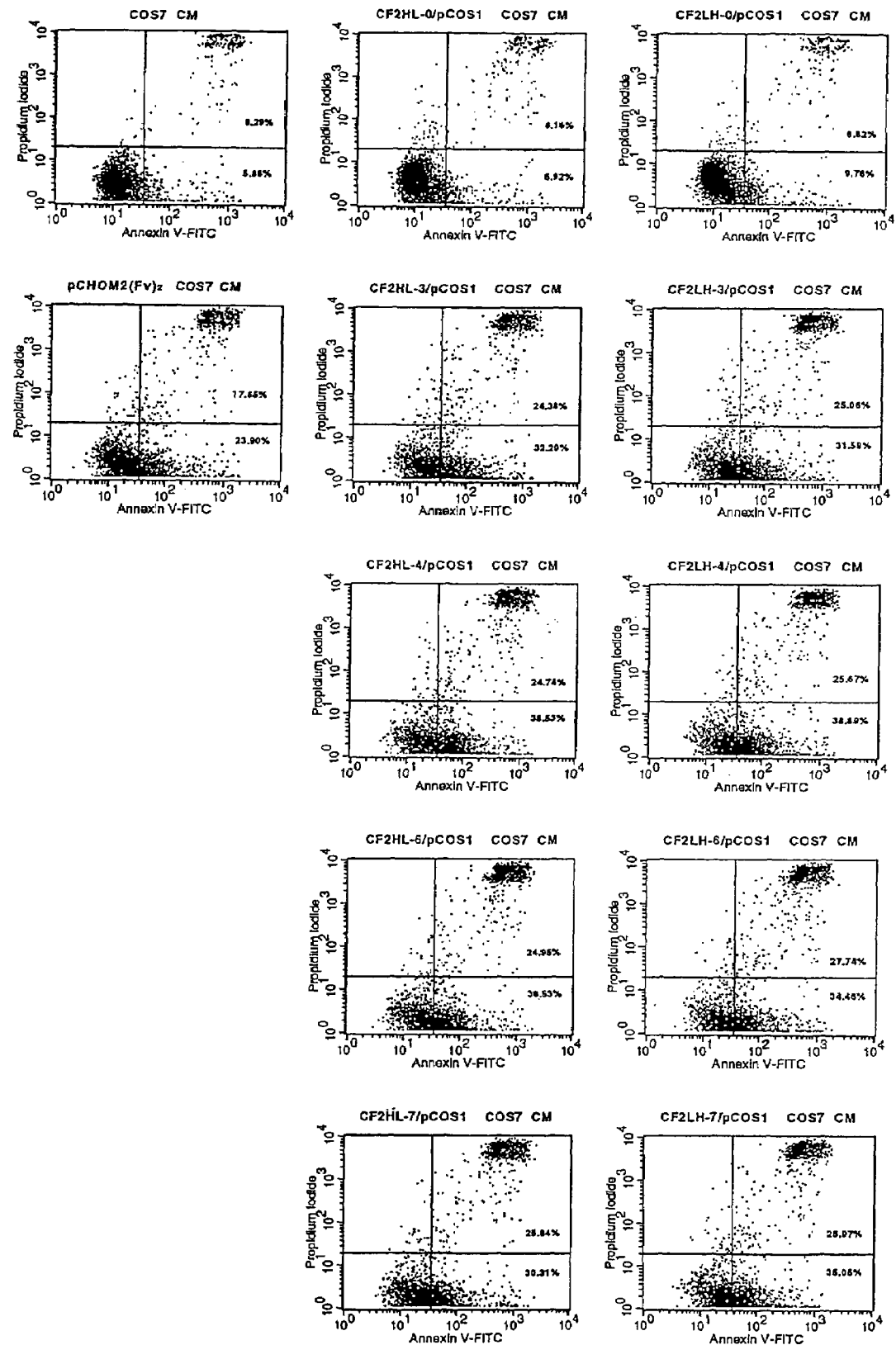
FIG. 41 shows the results of the apoptosis-inducing effect in Example 6.6, illustrating that the scFv <HL3, 4, 6, 7, LH3, 4, 6 and 7> and the sc(Fv)$_2$ remarkably induce cell death of hIAP/L1210 cells.
Figure 42:
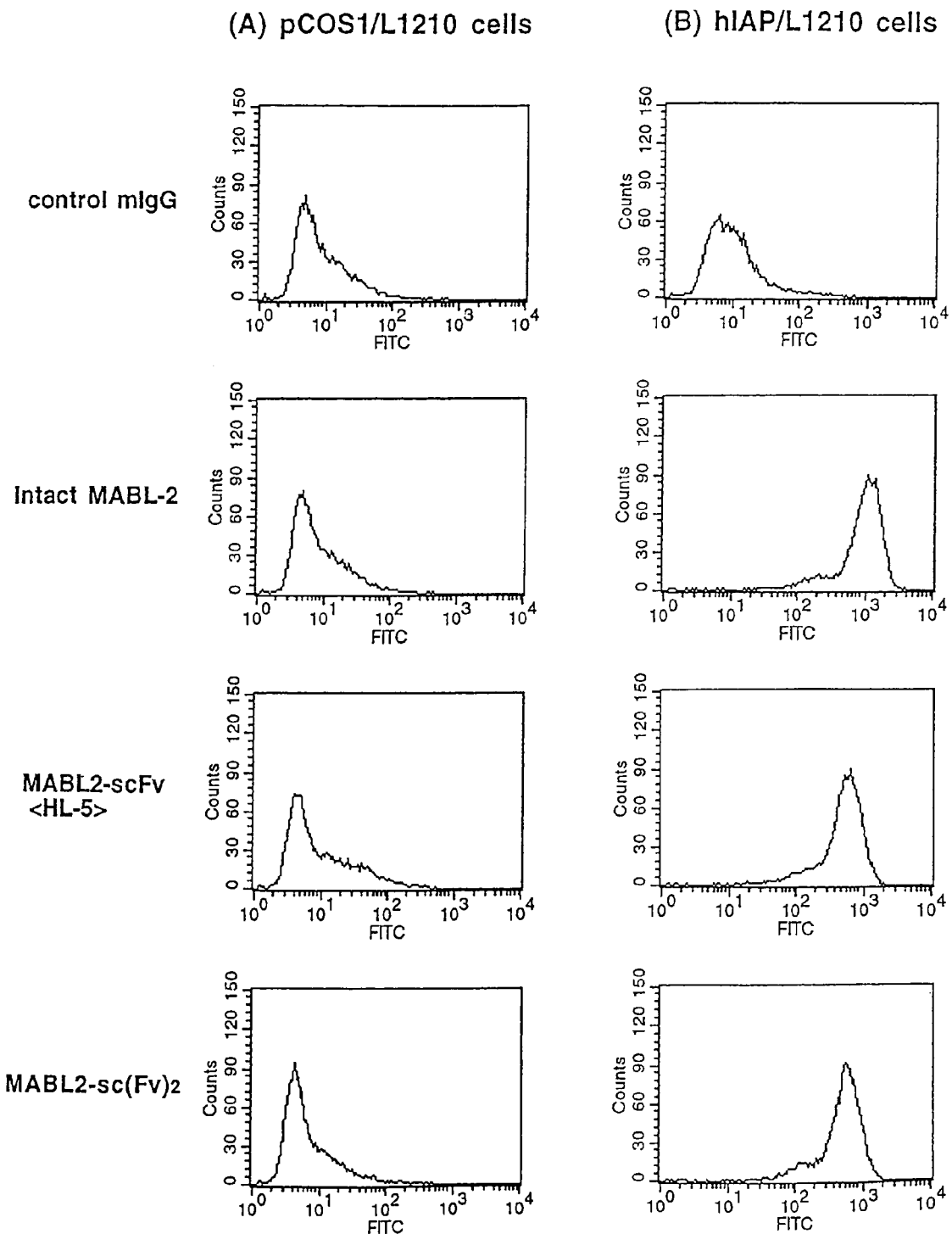
FIG. 42 shows the results of the evaluation of antigen binding capacity in Example 6.10, illustrating that the dimer of scFv <HL5> and sc(FV)$_2$ have high affinities against human IAP.
Figure 43:
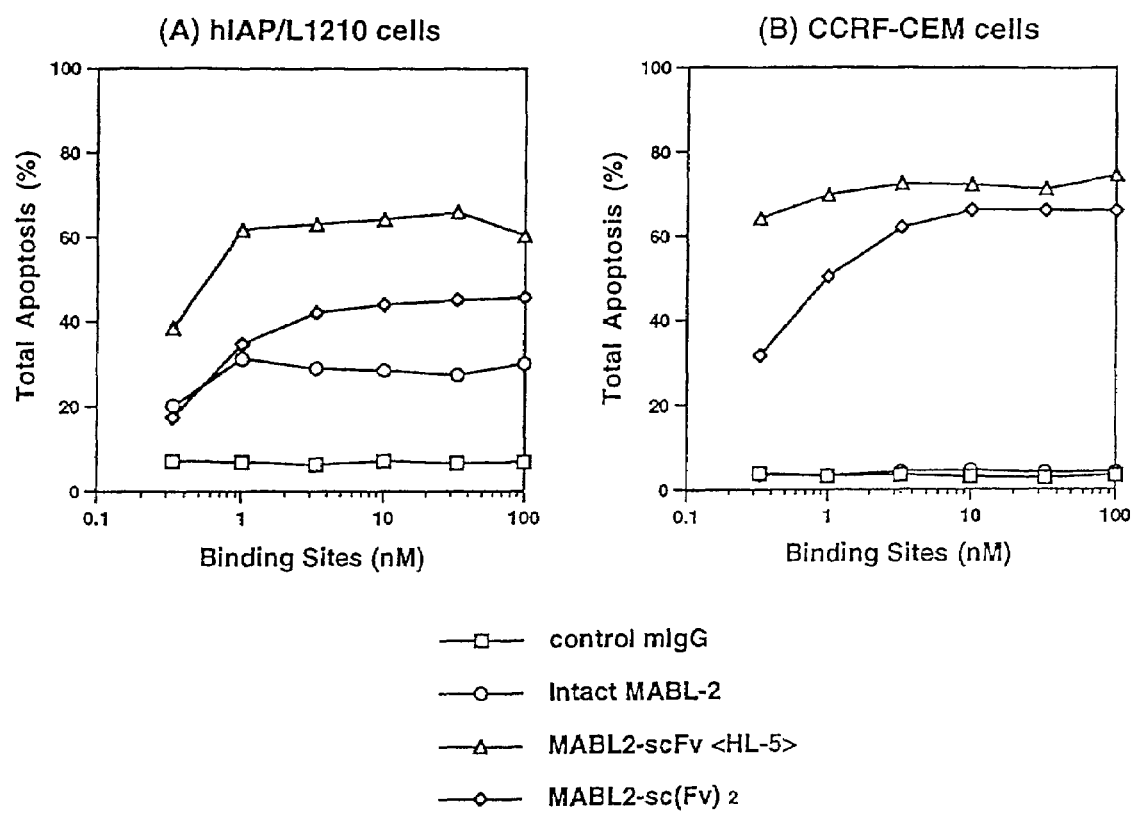
FIG. 43 shows the results of the in vitro apoptosis-inducing effect in Example 6.11, illustrating that the dimer of scFv <HL5> and the sc(Fv)$_2$ induce apoptosis of hIAP/L1210 cells and CCRF-CEM cells in concentration-dependent manner.
Figure 44:
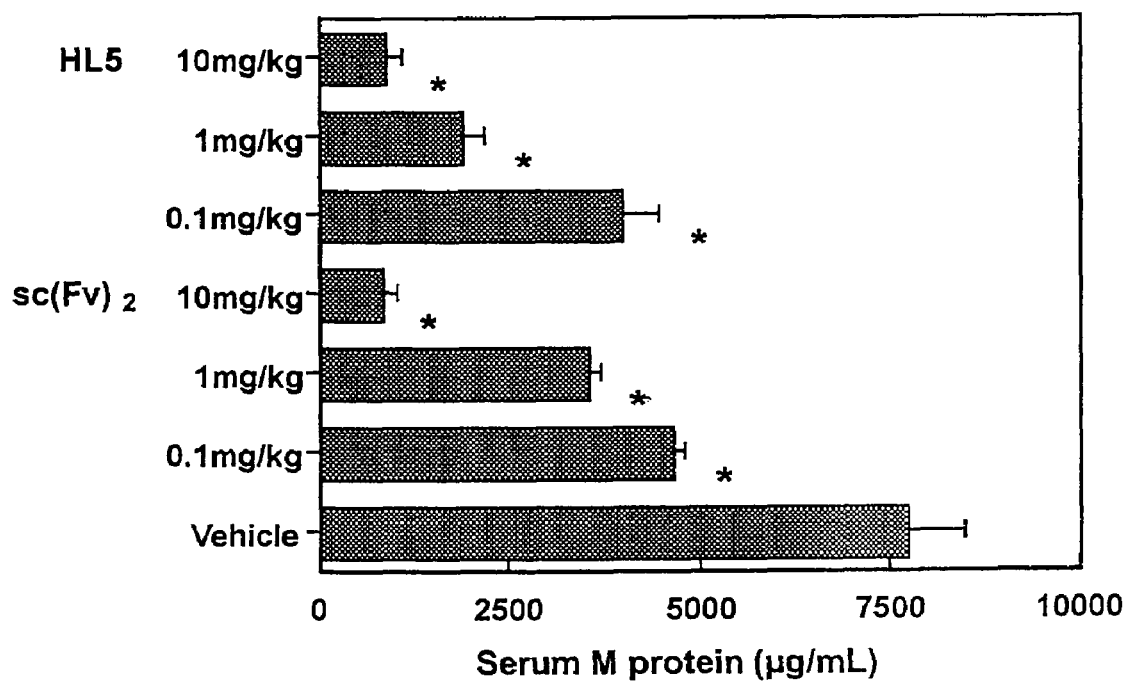
FIG. 44 shows the results of the quantitative measurement of M protein produced by a human myeloma cell line KPMM2 in the serum of the human myeloma cell-transplanted mouse. It illustrates that the dimer of scFv <HL5> and the sc(Fv)$_2$ remarkably inhibited growth of the KPMM2 cells.
Figure 45:
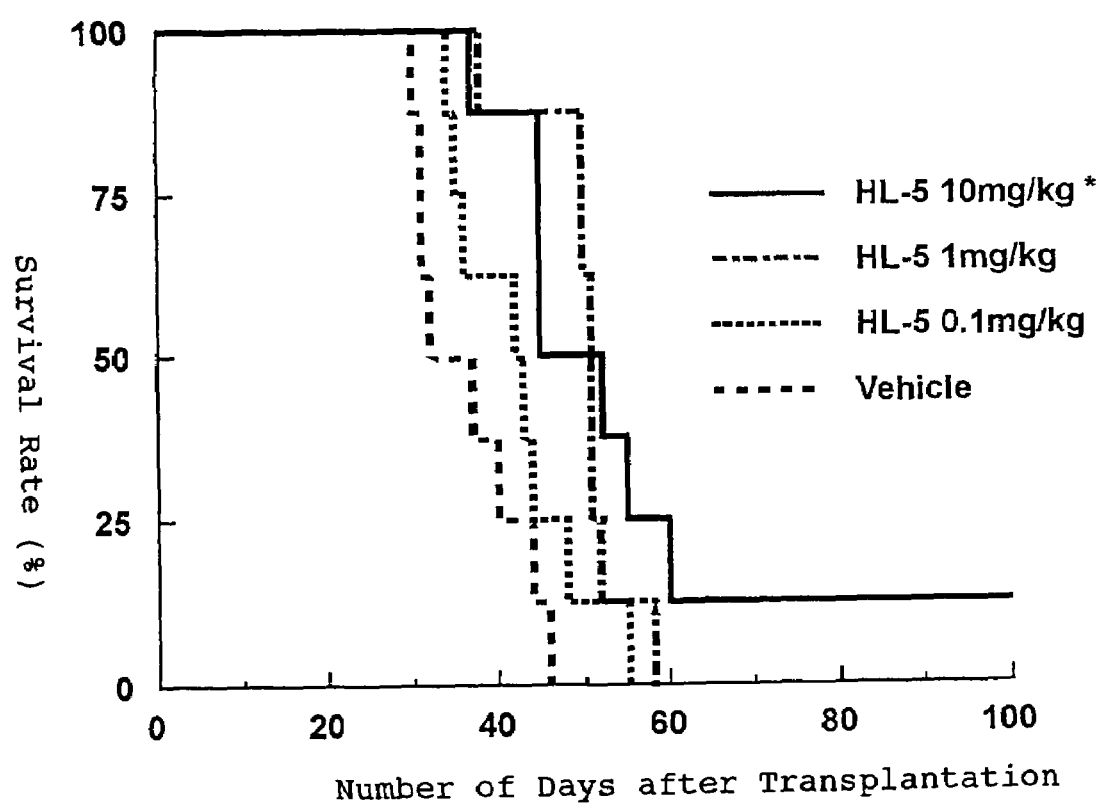
FIG. 45 shows the survival time (days) of mice after the transplantation of tumor, illustrating that the survival time of the scFv <HL5> administrated-group was remarkably prolonged.
Figure 46:
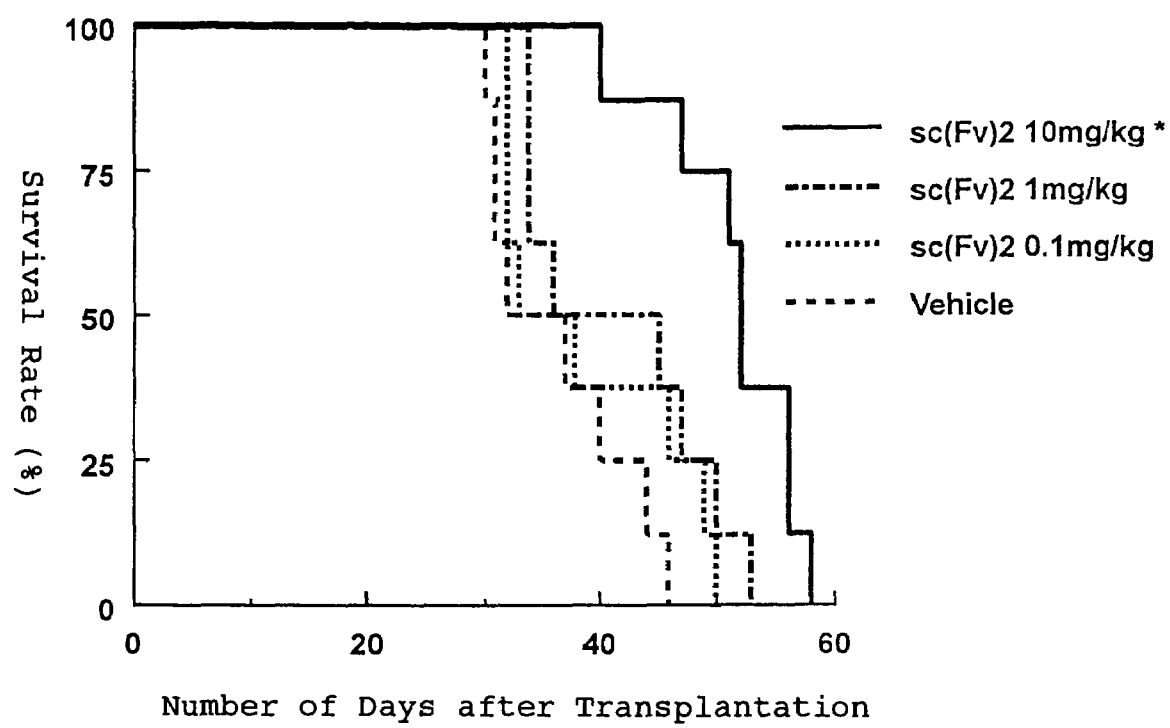
FIG. 46 shows the survival time (days) of mice after the transplantation of tumor, illustrating that the survival time of the sc(Fv)$_2$ administrated-group was remarkably prolonged.

The reconstructed polypeptides of the invention have properties of inducing apoptosis of nucleated blood cells having Integrin Associated Protein (IAP) and causing no hemagglutination, and are useful as a therapeutic agent for blood dyscrasia, for example, leukemia such as acute myeloid leukemia, chronic myelogenous leukemia, acute lymphoblastic leukemia, chronic lymphocytic leukemia, adult T-cell leukemia, multiple myeloma, mixed leukemia and hairy cell leukemia, malignant lymphoma (Hodgkin's disease, non-Hodgkin's lymphoma), aplastic anemia, myelodysplasia syndrome and polycythemia vera.

What is claimed is:

1. A reconstructed antibody which binds to Integrin Associated Protein (IAP), induces apoptosis of nucleated blood cells and causes no hemagglutination, wherein the reconstructed antibody comprises SEQ. ID NO. 101, or dimer of a sequence selected from SEQ ID NO. 95, SEQ ID NO. 96, SEQ ID NO. 97, SEQ ID NO. 98, SEQ ID NO. 100, SEQ ID NO. 102, or SEQ ID NO. 103.

2. A therapeutic agent for blood dyscrasia which comprises the reconstructed antibody of claim 1.

3. The therapeutic agent of claim 2, wherein the blood dyscrasia is leukemia.

4. The reconstructed antibody of claim 1, wherein the reconstructed antibody comprises a dimer of SEQ ID NO. 95.

5. The reconstructed antibody of claim 1, wherein the reconstructed antibody comprises a dimer of SEQ ID NO. 96.

6. The reconstructed antibody of claim 1, wherein the reconstructed antibody comprises a dimer of SEQ ID NO. 97.

7. The reconstructed antibody of claim 1, wherein the reconstructed antibody comprises a dimer of SEQ ID NO. 98.

8. The reconstructed antibody of claim 1, wherein the reconstructed antibody comprises a dimer of SEQ ID NO. 100.

9. The reconstructed antibody of claim 1, wherein the reconstructed antibody comprises SEQ ID NO. 101.

10. The reconstructed antibody of claim 1, wherein the reconstructed antibody comprises a dimer of SEQ ID NO. 102.

11. The reconstructed antibody of claim 1, wherein the reconstructed antibody comprises a dimer of SEQ ID NO. 103.

12. The therapeutic agent of claim 2, wherein the reconstructed antibody comprises a dimer of SEQ ID NO. 95.

13. The therapeutic agent of claim 2, wherein the reconstructed antibody comprises a dimer of SEQ ID NO. 96.

14. The therapeutic agent of claim 2, wherein the reconstructed antibody comprises a dimer of SEQ ID NO. 97.

15. The therapeutic agent of claim 2, wherein the reconstructed antibody comprises a dimer of SEQ ID NO. 98.

16. The therapeutic agent of claim 2, wherein the reconstructed antibody comprises a dimer of SEQ ID NO. 100.

17. The therapeutic agent of claim 2, wherein the reconstructed antibody comprises SEQ ID NO. 101.

18. The therapeutic agent of claim 2, wherein the reconstructed antibody comprises a dimer of SEQ ID NO. 102.

19. The therapeutic agent of claim 2, wherein the reconstructed antibody comprises a dimer of SEQ ID NO. 103.

* * * * *

```
                        SEQUENCE LISTING

<160> NUMBER OF SEQ ID NOS: 103

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
ccatcctaat acgactcact atagggc                                            27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 2
ggatcccggg tggatggtgg gaagatg                                            27

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 3
ggatcccggg ccagtggata gacagatg                                           28

<210> SEQ ID NO 4
<211> LENGTH: 26
```

```
<212> TYPE: DNA
<213> ORGANISM: Artificial Sequence
<220> FEATURE:
<223> OTHER INFORMATION: Description of Artificial Sequence: Primer

<400> SEQUENCE: 4
ggatcccggg agtggataga ccgatg                                            26

<210> SEQ ID NO 5
<211> LENGTH: 394
<212> TYPE: DNA
<213> ORGANISM: Mus sp.
<220> FEATURE:
<221> NAME/KEY: CDS
<222> LOCATION: (1)..(393)
<223> OTHER INFORMATION: pGEM-M1L
<220> FEATURE:
<221> NAME/KEY: sig_peptide
<222> LOCATION: (1)..(57)
<220> FEATURE:
<221> NAME/KEY: mat_peptide
<222> LOCATION: (58)..(393)

<400> SEQUENCE: 5 atg aag ttg cct gtt agg ctg ttg gtg ctg atg ttc tgg att cct gcg        48
Met Lys Leu Pro Val Arg Leu Leu Val Leu Met Phe Trp Ile Pro Ala
            -15                 -10                 -5 tcc agc agt gat gtt gtg atg acc caa act cca ctc tcc ctg cct gtc        96
Ser Ser Ser Asp Val Val Met Thr Gln Thr Pro Leu Ser Leu Pro Val
        -1   1               5                   10 agt ctt gga gat caa gcc tcc atc tct tgc aga tct agt cag agc ctt       144
Ser Leu Gly Asp Gln Ala Ser Ile Ser Cys Arg Ser Ser Gln Ser Leu
     15                  20                  25 cta cac agt aaa gga aac acc tat tta caa tgg tac cta cag aag cca       192
Leu His Ser Lys Gly Asn Thr Tyr Leu Gln Trp Tyr Leu Gln Lys Pro
 30                  35                  40                  45 ggc cag tct cca aag ctc ctg atc tac aaa gtt tcc aac cga ttt tct       240
Gly Gln Ser Pro Lys Leu Leu Ile Tyr Lys Val Ser Asn Arg Phe Ser
                 50                  55                  60 ggg gtc cca gac agg ttc agt ggc agt gga tca ggg aca gat ttc aca       288
Gly Val Pro Asp Arg Phe Ser Gly Ser Gly Ser Gly Thr Asp Phe Thr
             65                  70                  75 ctc aag atc agc aga gtg gag gct gag gat ctg gga gtt tat ttc tgc       336
Leu Lys Ile Ser Arg Val Glu Ala Glu Asp Leu Gly Val Tyr Phe Cys
         80                  85                  90 tct caa agt aca cat gtt ccg tac acg tcc gga ggg ggg acc aag ctg       384
Ser Gln Ser Thr His Val Pro Tyr Thr Ser Gly Gly Gly Thr Lys Leu
     95                  100                 105 gaa ata aaa c                                                         394
Glu Ile Lys
110

<210> SEQ ID NO 6
<211> LENGTH: 409
<212> TYPE: DNA
<213> ORGANISM: Mus sp.
<220> FEATURE:
<221> NAME/KEY: CDS
<222> LOCATION: (1)..(408)
<223> OTHER INFORMATION: pGEM-M1H
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)
```

<400> SEQUENCE: 6

```
atg gaa tgg agc tgg ata ttt ctc ttc ctc ctg tca gga act gca ggt        48
Met Glu Trp Ser Trp Ile Phe Leu Phe Leu Leu Ser Gly Thr Ala Gly
            -15                 -10                 -5 gtc cac tcc cag gtc cag ctg cag cag tct gga cct gac ctg gta aag        96
Val His Ser Gln Val Gln Leu Gln Gln Ser Gly Pro Asp Leu Val Lys
     -1   1               5                  10 cct ggg gct tca gtg aag atg tcc tgc aag gct tct gga tac acc ttc       144
Pro Gly Ala Ser Val Lys Met Ser Cys Lys Ala Ser Gly Tyr Thr Phe
         15                  20                  25 gtt aac cat gtt atg cac tgg gtg aag cag aag cca ggg cag ggc ctt       192
Val Asn His Val Met His Trp Val Lys Gln Lys Pro Gly Gln Gly Leu
     30                  35                  40                  45 gag tgg att gga tat att tat cct tac aat gat ggt act aag tac aat       240
Glu Trp Ile Gly Tyr Ile Tyr Pro Tyr Asn Asp Gly Thr Lys Tyr Asn
             50                  55                  60 gag aag ttc aag ggc aag gcc aca ctg act tca gag aaa tcc tcc agc       288
Glu Lys Phe Lys Gly Lys Ala Thr Leu Thr Ser Glu Lys Ser Ser Ser
         65                  70                  75 gca gcc tac atg gag ctc agc agc ctg gcc tct gag gac tct gcg gtc       336
Ala Ala Tyr Met Glu Leu Ser Ser Leu Ala Ser Glu Asp Ser Ala Val
     80                  85                  90 tac tac tgt gca aga ggg ggt tac tat agt tac gac gac tgg ggc caa       384
Tyr Tyr Cys Ala Arg Gly Gly Tyr Tyr Ser Tyr Asp Asp Trp Gly Gln
 95                 100                 105 ggc acc act ctc aca gtc tcc tca g                                     409
Gly Thr Thr Leu Thr Val Ser Ser
110                 115
```

<210> SEQ ID NO 7
<211> LENGTH: 394
<212> TYPE: DNA
<213> ORGANISM: Mus sp.
<220> FEATURE:
<221> NAME/KEY: CDS
<222> LOCATION: (1)..(393)
<223> OTHER INFORMATION: pGEM-M2L
<220> FEATURE:
<221> NAME/KEY: sig_peptide
<222> LOCATION: (1)..(57)
<220> FEATURE:
<221> NAME/KEY: mat_peptide
<222> LOCATION: (58)..(393)

<400> SEQUENCE: 7

```
atg aag ttg cct gtt agg ctg ttg gtg ctg atg ttc tgg att cct ggt        48
Met Lys Leu Pro Val Arg Leu Leu Val Leu Met Phe Trp Ile Pro Gly
            -15                 -10                 -5 tcc agc agt gat gtt gtg atg acc caa agt cca ctc tcc ctg cct gtc        96
Ser Ser Ser Asp Val Val Met Thr Gln Ser Pro Leu Ser Leu Pro Val
            -1   1               5                  10 agt ctt gga gat caa gcc tcc atc tct tgc aga tca agt cag agc ctt       144
Ser Leu Gly Asp Gln Ala Ser Ile Ser Cys Arg Ser Ser Gln Ser Leu
         15                  20                  25 gtg cac agt aat gga aag acc tat tta cat tgg tac ctg cag aag cca       192
Val His Ser Asn Gly Lys Thr Tyr Leu His Trp Tyr Leu Gln Lys Pro
     30                  35                  40                  45 ggc cag tct cca aaa ctc ctg atc tac aaa gtt tcc aac cga ttt tct       240
Gly Gln Ser Pro Lys Leu Leu Ile Tyr Lys Val Ser Asn Arg Phe Ser
             50                  55                  60 ggg gtc cca gac agg ttc agt ggc agt gga tca gtg aca gat ttc aca       288
Gly Val Pro Asp Arg Phe Ser Gly Ser Gly Ser Val Thr Asp Phe Thr
         65                  70                  75
```

```
ctc atg atc agc aga gtg gag gct gag gat ctg gga gtt tat ttc tgc    336
Leu Met Ile Ser Arg Val Glu Ala Glu Asp Leu Gly Val Tyr Phe Cys
        80                  85                  90 tct caa agt aca cat gtt ccg tac acg ttc gga ggg ggg acc aag ctg    384
Ser Gln Ser Thr His Val Pro Tyr Thr Phe Gly Gly Gly Thr Lys Leu
        95                 100                 105 gaa ata aaa c                                                      394
Glu Ile Lys
110

<210> SEQ ID NO 8
<211> LENGTH: 409
<212> TYPE: DNA
<213> ORGANISM: Mus sp.
<220> FEATURE:
<221> NAME/KEY: CDS
<222> LOCATION: (1)..(408)
<223> OTHER INFORMATION: pGEM-M2H
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 8 atg gaa tgg agc tgg ata ttt ctc ttc ctc ctg tca gga act gca ggt     48
Met Glu Trp Ser Trp Ile Phe Leu Phe Leu Leu Ser Gly Thr Ala Gly
                -15                 -10                  -5 gtc cac tcc cag gtc cag ctg cag cag tct gga cct gaa ctg gta aag     96
Val His Ser Gln Val Gln Leu Gln Gln Ser Gly Pro Glu Leu Val Lys
         -1  1                   5                  10 cct ggg gct tca gtg aag atg tcc tgc aag gct tct gga tac acc ttc    144
Pro Gly Ala Ser Val Lys Met Ser Cys Lys Ala Ser Gly Tyr Thr Phe
        15                  20                  25 gct aac cat gtt att cac tgg gtg aag cag aag cca ggg cag ggc ctt    192
Ala Asn His Val Ile His Trp Val Lys Gln Lys Pro Gly Gln Gly Leu
    30                  35                  40                  45 gag tgg att gga tat att tat cct tac aat gat ggt act aag tat aat    240
Glu Trp Ile Gly Tyr Ile Tyr Pro Tyr Asn Asp Gly Thr Lys Tyr Asn
                50                  55                  60 gag aag ttc aag gac aag gcc act ctg act tca gac aaa tcc tcc acc    288
Glu Lys Phe Lys Asp Lys Ala Thr Leu Thr Ser Asp Lys Ser Ser Thr
            65                  70                  75 aca gcc tac atg gac ctc agc agc ctg gcc tct gag gac tct gcg gtc    336
Thr Ala Tyr Met Asp Leu Ser Ser Leu Ala Ser Glu Asp Ser Ala Val
        80                  85                  90 tat tac tgt gca aga ggg ggt tac tat act tac gac gac tgg ggc caa    384
Tyr Tyr Cys Ala Arg Gly Gly Tyr Tyr Thr Tyr Asp Asp Trp Gly Gln
    95                 100                 105 ggc acc act ctc aca gtc tcc tca g                                  409
Gly Thr Thr Leu Thr Val Ser Ser
110                 115

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 9
cccaagcttc caccatgaag ttgcctgtta gg                                 32
```

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 10
cccaagcttc caccatggaa tggagctgga ta                          32

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 11
cgcggatcca ctcacgtttt atttccagct tggt                        34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 12
cgcggatcca ctcacctgag gagactgtga gagt                        34

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
catgccatgg cgcaggtcca gctgcagcag                             30

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
accaccacct gaggagactg tgagagt                                27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 15
gtctcctcag gtggtggtgg ttcgggt                                27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Primer -continued

<400> SEQUENCE: 16
cacaacatcc gatccgccac cacccga                                              27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 17
ggcggatcgg atgttgtgat gacccaa                                              27

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 18
ccggaattct cattatttat cgtcatcgtc tttgtagtct tttatttcca gcttggt            57

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Linker
      nucleotide sequence
<220> FEATURE:
<221> NAME/KEY: CDS
<222> LOCATION: (1)..(45)

<400> SEQUENCE: 19

```
ggt ggt ggt ggt tcg ggt ggt ggt ggt tcg ggt ggt ggc gga tcg              45
Gly Gly Gly Gly Ser Gly Gly Gly Gly Ser Gly Gly Gly Gly Ser
 1               5                  10                  15
```

<210> SEQ ID NO 20
<211> LENGTH: 828
<212> TYPE: DNA
<213> ORGANISM: Mus sp.
<220> FEATURE:
<221> NAME/KEY: CDS
<222> LOCATION: (1)..(822)
<223> OTHER INFORMATION: pscM1. MABL1-scFv

<400> SEQUENCE: 20

```
atg aaa tac cta ttg cct acg gca gcc gct gga ttg tta tta ctc gct          48
Met Lys Tyr Leu Leu Pro Thr Ala Ala Ala Gly Leu Leu Leu Leu Ala
 1               5                  10                  15 gcc caa cca gcc atg gcg cag gtc cag ctg cag cag tct gga cct gac          96
Ala Gln Pro Ala Met Ala Gln Val Gln Leu Gln Gln Ser Gly Pro Asp
                20                  25                  30 ctg gta aag cct ggg gct tca gtg aag atg tcc tgc aag gct tct gga         144
Leu Val Lys Pro Gly Ala Ser Val Lys Met Ser Cys Lys Ala Ser Gly
            35                  40                  45 tac acc ttc gtt aac cat gtt atg cac tgg gtg aag cag aag cca ggg         192
Tyr Thr Phe Val Asn His Val Met His Trp Val Lys Gln Lys Pro Gly
        50                  55                  60 cag ggc ctt gag tgg att gga tat att tat cct tac aat gat ggt act         240
Gln Gly Leu Glu Trp Ile Gly Tyr Ile Tyr Pro Tyr Asn Asp Gly Thr
    65                  70                  75                  80
```

| | | | | | | | | | | | | | | | | |
|---|---|---|---|---|---|---|---|---|---|---|---|---|---|---|---|---|
| aag | tac | aat | gag | aag | ttc | aag | ggc | aag | gcc | aca | ctg | act | tca | gag | aaa | 288 |
| Lys | Tyr | Asn | Glu | Lys | Phe | Lys | Gly | Lys | Ala | Thr | Leu | Thr | Ser | Glu | Lys | |
| | | | | 85 | | | | | 90 | | | | | 95 | | |
| tcc | tcc | agc | gca | gcc | tac | atg | gag | ctc | agc | agc | ctg | gcc | tct | gag | gac | 336 |
| Ser | Ser | Ser | Ala | Ala | Tyr | Met | Glu | Leu | Ser | Ser | Leu | Ala | Ser | Glu | Asp | |
| | | | 100 | | | | | 105 | | | | | 110 | | | |
| tct | gcg | gtc | tac | tac | tgt | gca | aga | ggg | ggt | tac | tat | agt | tac | gac | gac | 384 |
| Ser | Ala | Val | Tyr | Tyr | Cys | Ala | Arg | Gly | Gly | Tyr | Tyr | Ser | Tyr | Asp | Asp | |
| | | 115 | | | | | 120 | | | | | 125 | | | | |
| tgg | ggc | caa | ggc | acc | act | ctc | aca | gtc | tcc | tca | ggt | ggt | ggt | ggt | tcg | 432 |
| Trp | Gly | Gln | Gly | Thr | Thr | Leu | Thr | Val | Ser | Ser | Gly | Gly | Gly | Gly | Ser | |
| | 130 | | | | | 135 | | | | | 140 | | | | | |
| ggt | ggt | ggt | ggt | tcg | ggt | ggt | ggc | gga | tcg | gat | gtt | gtg | atg | acc | caa | 480 |
| Gly | Gly | Gly | Gly | Ser | Gly | Gly | Gly | Gly | Ser | Asp | Val | Val | Met | Thr | Gln | |
| 145 | | | | | 150 | | | | | 155 | | | | | 160 | |
| act | cca | ctc | tcc | ctg | cct | gtc | agt | ctt | gga | gat | caa | gcc | tcc | atc | tct | 528 |
| Thr | Pro | Leu | Ser | Leu | Pro | Val | Ser | Leu | Gly | Asp | Gln | Ala | Ser | Ile | Ser | |
| | | | | 165 | | | | | 170 | | | | | 175 | | |
| tgc | aga | tct | agt | cag | agc | ctt | cta | cac | agt | aaa | gga | aac | acc | tat | tta | 576 |
| Cys | Arg | Ser | Ser | Gln | Ser | Leu | Leu | His | Ser | Lys | Gly | Asn | Thr | Tyr | Leu | |
| | | | 180 | | | | | 185 | | | | | 190 | | | |
| caa | tgg | tac | cta | cag | aag | cca | ggc | cag | tct | cca | aag | ctc | ctg | atc | tac | 624 |
| Gln | Trp | Tyr | Leu | Gln | Lys | Pro | Gly | Gln | Ser | Pro | Lys | Leu | Leu | Ile | Tyr | |
| | | 195 | | | | | 200 | | | | | 205 | | | | |
| aaa | gtt | tcc | aac | cga | ttt | tct | ggg | gtc | cca | gac | agg | ttc | agt | ggc | agt | 672 |
| Lys | Val | Ser | Asn | Arg | Phe | Ser | Gly | Val | Pro | Asp | Arg | Phe | Ser | Gly | Ser | |
| | 210 | | | | | 215 | | | | | 220 | | | | | |
| gga | tca | ggg | aca | gat | ttc | aca | ctc | aag | atc | agc | aga | gtg | gag | gct | gag | 720 |
| Gly | Ser | Gly | Thr | Asp | Phe | Thr | Leu | Lys | Ile | Ser | Arg | Val | Glu | Ala | Glu | |
| 225 | | | | | 230 | | | | | 235 | | | | | 240 | |
| gat | ctg | gga | gtt | tat | ttc | tgc | tct | caa | agt | aca | cat | gtt | ccg | tac | acg | 768 |
| Asp | Leu | Gly | Val | Tyr | Phe | Cys | Ser | Gln | Ser | Thr | His | Val | Pro | Tyr | Thr | |
| | | | | 245 | | | | | 250 | | | | | 255 | | |
| tcc | gga | ggg | ggg | acc | aag | ctg | gaa | ata | aaa | gac | tac | aaa | gac | gat | gac | 816 |
| Ser | Gly | Gly | Gly | Thr | Lys | Leu | Glu | Ile | Lys | Asp | Tyr | Lys | Asp | Asp | Asp | |
| | | | 260 | | | | | 265 | | | | | 270 | | | |
| gat | aaa | taatga | | | | | | | | | | | | | | 828 |
| Asp | Lys | | | | | | | | | | | | | | | |

```
<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 21
acgcgtcgac tcccaggtcc agctgcagca g                              31

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
gaaggtgtat ccagaagc                                              18

<210> SEQ ID NO 23
<211> LENGTH: 819
<212> TYPE: DNA
```

<213> ORGANISM: Mus sp.
<220> FEATURE:
<221> NAME/KEY: CDS
<222> LOCATION: (1)..(813)
<223> OTHER INFORMATION: pCHOM1. MABL1-scFv

<400> SEQUENCE: 23

```
atg gga tgg agc tgt atc atc ctc ttc ttg gta gca aca gct aca ggt        48
Met Gly Trp Ser Cys Ile Ile Leu Phe Leu Val Ala Thr Ala Thr Gly
 1               5                  10                  15 gtc gac tcc cag gtc cag ctg cag cag tct gga cct gac ctg gta aag        96
Val Asp Ser Gln Val Gln Leu Gln Gln Ser Gly Pro Asp Leu Val Lys
             20                  25                  30 cct ggg gct tca gtg aag atg tcc tgc aag gct tct gga tac acc ttc       144
Pro Gly Ala Ser Val Lys Met Ser Cys Lys Ala Ser Gly Tyr Thr Phe
         35                  40                  45 gtt aac cat gtt atg cac tgg gtg aag cag aag cca ggg cag ggc ctt       192
Val Asn His Val Met His Trp Val Lys Gln Lys Pro Gly Gln Gly Leu
     50                  55                  60 gag tgg att gga tat att tat cct tac aat gat ggt act aag tac aat       240
Glu Trp Ile Gly Tyr Ile Tyr Pro Tyr Asn Asp Gly Thr Lys Tyr Asn
 65                  70                  75                  80 gag aag ttc aag ggc aag gcc aca ctg act tca gag aaa tcc tcc agc       288
Glu Lys Phe Lys Gly Lys Ala Thr Leu Thr Ser Glu Lys Ser Ser Ser
                 85                  90                  95 gca gcc tac atg gag ctc agc agc ctg gcc tct gag gac tct gcg gtc       336
Ala Ala Tyr Met Glu Leu Ser Ser Leu Ala Ser Glu Asp Ser Ala Val
            100                 105                 110 tac tac tgt gca aga ggg ggt tac tat agt tac gac gac tgg ggc caa       384
Tyr Tyr Cys Ala Arg Gly Gly Tyr Tyr Ser Tyr Asp Asp Trp Gly Gln
        115                 120                 125 ggc acc act ctc aca gtc tcc tca ggt ggt ggt ggt tcg ggt ggt ggt       432
Gly Thr Thr Leu Thr Val Ser Ser Gly Gly Gly Gly Ser Gly Gly Gly
    130                 135                 140 ggt tcg ggt ggt ggc gga tcg gat gtt gtg atg acc caa act cca ctc       480
Gly Ser Gly Gly Gly Gly Ser Asp Val Val Met Thr Gln Thr Pro Leu
145                 150                 155                 160 tcc ctg cct gtc agt ctt gga gat caa gcc tcc atc tct tgc aga tct       528
Ser Leu Pro Val Ser Leu Gly Asp Gln Ala Ser Ile Ser Cys Arg Ser
                165                 170                 175 agt cag agc ctt cta cac agt aaa gga aac acc tat tta caa tgg tac       576
Ser Gln Ser Leu Leu His Ser Lys Gly Asn Thr Tyr Leu Gln Trp Tyr
            180                 185                 190 cta cag aag cca ggc cag tct cca aag ctc ctg atc tac aaa gtt tcc       624
Leu Gln Lys Pro Gly Gln Ser Pro Lys Leu Leu Ile Tyr Lys Val Ser
        195                 200                 205 aac cga ttt tct ggg gtc cca gac agg ttc agt ggc agt gga tca ggg       672
Asn Arg Phe Ser Gly Val Pro Asp Arg Phe Ser Gly Ser Gly Ser Gly
    210                 215                 220 aca gat ttc aca ctc aag atc agc aga gtg gag gct gag gat ctg gga       720
Thr Asp Phe Thr Leu Lys Ile Ser Arg Val Glu Ala Glu Asp Leu Gly
225                 230                 235                 240 gtt tat ttc tgc tct caa agt aca cat gtt ccg tac acg tcc gga ggg       768
Val Tyr Phe Cys Ser Gln Ser Thr His Val Pro Tyr Thr Ser Gly Gly
                245                 250                 255 ggg acc aag ctg gaa ata aaa gac tac aaa gac gat gac gat aaa           813
Gly Thr Lys Leu Glu Ile Lys Asp Tyr Lys Asp Asp Asp Asp Lys
            260                 265                 270 taatga                                                                819
```

<210> SEQ ID NO 24
<211> LENGTH: 828
<212> TYPE: DNA
<213> ORGANISM: Mus sp.
<220> FEATURE:
<221> NAME/KEY: CDS
<222> LOCATION: (1)..(822)
<223> OTHER INFORMATION: pscM2. MABL2-scFv

<400> SEQUENCE: 24

```
atg aaa tac cta ttg cct acg gca gcc gct gga ttg tta tta ctc gct      48
Met Lys Tyr Leu Leu Pro Thr Ala Ala Ala Gly Leu Leu Leu Leu Ala
 1               5                  10                  15 gcc caa cca gcc atg gcg cag gtc cag ctg cag cag tct gga cct gaa      96
Ala Gln Pro Ala Met Ala Gln Val Gln Leu Gln Gln Ser Gly Pro Glu
             20                  25                  30 ctg gta aag cct ggg gct tca gtg aag atg tcc tgc aag gct tct gga     144
Leu Val Lys Pro Gly Ala Ser Val Lys Met Ser Cys Lys Ala Ser Gly
         35                  40                  45 tac acc ttc gct aac cat gtt att cac tgg gtg aag cag aag cca ggg     192
Tyr Thr Phe Ala Asn His Val Ile His Trp Val Lys Gln Lys Pro Gly
     50                  55                  60 cag ggc ctt gag tgg att gga tat att tat cct tac aat gat ggt act     240
Gln Gly Leu Glu Trp Ile Gly Tyr Ile Tyr Pro Tyr Asn Asp Gly Thr
 65                  70                  75                  80 aag tat aat gag aag ttc aag gac aag gcc act ctg act tca gac aaa     288
Lys Tyr Asn Glu Lys Phe Lys Asp Lys Ala Thr Leu Thr Ser Asp Lys
                 85                  90                  95 tcc tcc acc aca gcc tac atg gac ctc agc agc ctg gcc tct gag gac     336
Ser Ser Thr Thr Ala Tyr Met Asp Leu Ser Ser Leu Ala Ser Glu Asp
            100                 105                 110 tct gcg gtc tat tac tgt gca aga ggg ggt tac tat act tac gac gac     384
Ser Ala Val Tyr Tyr Cys Ala Arg Gly Gly Tyr Tyr Thr Tyr Asp Asp
        115                 120                 125 tgg ggc caa ggc acc act ctc aca gtc tcc tca ggt ggt ggt ggt tcg     432
Trp Gly Gln Gly Thr Thr Leu Thr Val Ser Ser Gly Gly Gly Gly Ser
    130                 135                 140 ggt ggt ggt ggt tcg ggt ggt ggc gga tcg gat gtt gtg atg acc caa     480
Gly Gly Gly Gly Ser Gly Gly Gly Gly Ser Asp Val Val Met Thr Gln
145                 150                 155                 160 agt cca ctc tcc ctg cct gtc agt ctt gga gat caa gcc tcc atc tct     528
Ser Pro Leu Ser Leu Pro Val Ser Leu Gly Asp Gln Ala Ser Ile Ser
                165                 170                 175 tgc aga tca agt cag agc ctt gtg cac agt aat gga aag acc tat tta     576
Cys Arg Ser Ser Gln Ser Leu Val His Ser Asn Gly Lys Thr Tyr Leu
            180                 185                 190 cat tgg tac ctg cag aag cca ggc cag tct cca aaa ctc ctg atc tac     624
His Trp Tyr Leu Gln Lys Pro Gly Gln Ser Pro Lys Leu Leu Ile Tyr
        195                 200                 205 aaa gtt tcc aac cga ttt tct ggg gtc cca gac agg ttc agt ggc agt     672
Lys Val Ser Asn Arg Phe Ser Gly Val Pro Asp Arg Phe Ser Gly Ser
    210                 215                 220 gga tca gtg aca gat ttc aca ctc atg atc agc aga gtg gag gct gag     720
Gly Ser Val Thr Asp Phe Thr Leu Met Ile Ser Arg Val Glu Ala Glu
225                 230                 235                 240 gat ctg gga gtt tat ttc tgc tct caa agt aca cat gtt ccg tac acg     768
Asp Leu Gly Val Tyr Phe Cys Ser Gln Ser Thr His Val Pro Tyr Thr
                245                 250                 255 ttc gga ggg ggg acc aag ctg gaa ata aaa gac tac aaa gac gat gac     816
Phe Gly Gly Gly Thr Lys Leu Glu Ile Lys Asp Tyr Lys Asp Asp Asp
            260                 265                 270
```

```
gat aaa taatga                                                               828
Asp Lys <210> SEQ ID NO 25
<211> LENGTH: 819
<212> TYPE: DNA
<213> ORGANISM: Mus sp.
<220> FEATURE:
<221> NAME/KEY: CDS
<222> LOCATION: (1)..(813)
<223> OTHER INFORMATION: pCHOM2. MABL2-scFv

<400> SEQUENCE: 25 atg gga tgg agc tgt atc atc ctc ttc ttg gta gca aca gct aca ggt    48
Met Gly Trp Ser Cys Ile Ile Leu Phe Leu Val Ala Thr Ala Thr Gly
 1               5                  10                  15 gtc gac tcc cag gtc cag ctg cag cag tct gga cct gaa ctg gta aag    96
Val Asp Ser Gln Val Gln Leu Gln Gln Ser Gly Pro Glu Leu Val Lys
            20                  25                  30 cct ggg gct tca gtg aag atg tcc tgc aag gct tct gga tac acc ttc   144
Pro Gly Ala Ser Val Lys Met Ser Cys Lys Ala Ser Gly Tyr Thr Phe
        35                  40                  45 gct aac cat gtt att cac tgg gtg aag cag aag cca ggg cag ggc ctt   192
Ala Asn His Val Ile His Trp Val Lys Gln Lys Pro Gly Gln Gly Leu
    50                  55                  60 gag tgg att gga tat att tat cct tac aat gat ggt act aag tat aat   240
Glu Trp Ile Gly Tyr Ile Tyr Pro Tyr Asn Asp Gly Thr Lys Tyr Asn
 65                 70                  75                  80 gag aag ttc aag gac aag gcc act ctg act tca gac aaa tcc tcc acc   288
Glu Lys Phe Lys Asp Lys Ala Thr Leu Thr Ser Asp Lys Ser Ser Thr
                85                  90                  95 aca gcc tac atg gac ctc agc agc ctg gcc tct gag gac tct gcg gtc   336
Thr Ala Tyr Met Asp Leu Ser Ser Leu Ala Ser Glu Asp Ser Ala Val
            100                 105                 110 tat tac tgt gca aga ggg ggt tac tat act tac gac gac tgg ggc caa   384
Tyr Tyr Cys Ala Arg Gly Gly Tyr Tyr Thr Tyr Asp Asp Trp Gly Gln
        115                 120                 125 ggc acc act ctc aca gtc tcc tca ggt ggt ggt ggt tcg ggt ggt ggt   432
Gly Thr Thr Leu Thr Val Ser Ser Gly Gly Gly Gly Ser Gly Gly Gly
    130                 135                 140 ggt tcg ggt ggt ggc gga tcg gat gtt gtg atg acc caa agt cca ctc   480
Gly Ser Gly Gly Gly Gly Ser Asp Val Val Met Thr Gln Ser Pro Leu
145                 150                 155                 160 tcc ctg cct gtc agt ctt gga gat caa gcc tcc atc tct tgc aga tca   528
Ser Leu Pro Val Ser Leu Gly Asp Gln Ala Ser Ile Ser Cys Arg Ser
                165                 170                 175 agt cag agc ctt gtg cac agt aat gga aag acc tat tta cat tgg tac   576
Ser Gln Ser Leu Val His Ser Asn Gly Lys Thr Tyr Leu His Trp Tyr
            180                 185                 190 ctg cag aag cca ggc cag tct cca aaa ctc ctg atc tac aaa gtt tcc   624
Leu Gln Lys Pro Gly Gln Ser Pro Lys Leu Leu Ile Tyr Lys Val Ser
        195                 200                 205 aac cga ttt tct ggg gtc cca gac agg ttc agt ggc agt gga tca gtg   672
Asn Arg Phe Ser Gly Val Pro Asp Arg Phe Ser Gly Ser Gly Ser Val
    210                 215                 220 aca gat ttc aca ctc atg atc agc aga gtg gag gct gag gat ctg gga   720
Thr Asp Phe Thr Leu Met Ile Ser Arg Val Glu Ala Glu Asp Leu Gly
225                 230                 235                 240 gtt tat ttc tgc tct caa agt aca cat gtt ccg tac acg ttc gga ggg   768
Val Tyr Phe Cys Ser Gln Ser Thr His Val Pro Tyr Thr Phe Gly Gly
                245                 250                 255
```

```
ggg acc aag ctg gaa ata aaa gac tac aaa gac gat gac gat aaa      813
Gly Thr Lys Leu Glu Ile Lys Asp Tyr Lys Asp Asp Asp Asp Lys
            260                 265                 270 taatga                                                            819

<210> SEQ ID NO 26
<211> LENGTH: 456
<212> TYPE: DNA
<213> ORGANISM: Mus sp.
<220> FEATURE:
<221> NAME/KEY: CDS
<222> LOCATION: (1)..(450)
<223> OTHER INFORMATION: pCHO-shIAP. Soluble human IAP

<400> SEQUENCE: 26 atg tgg ccc ctg gta gcg gcg ctg ttg ctg ggc tcg gcg tgc tgc gga   48
Met Trp Pro Leu Val Ala Ala Leu Leu Leu Gly Ser Ala Cys Cys Gly
  1               5                  10                  15 tca gct cag cta cta ttt aat aaa aca aaa tct gta gaa ttc acg ttt   96
Ser Ala Gln Leu Leu Phe Asn Lys Thr Lys Ser Val Glu Phe Thr Phe
             20                  25                  30 tgt aat gac act gtc gtc att cca tgc ttt gtt act aat atg gag gca  144
Cys Asn Asp Thr Val Val Ile Pro Cys Phe Val Thr Asn Met Glu Ala
         35                  40                  45 caa aac act act gaa gta tac gta aag tgg aaa ttt aaa gga aga gat  192
Gln Asn Thr Thr Glu Val Tyr Val Lys Trp Lys Phe Lys Gly Arg Asp
     50                  55                  60 att tac acc ttt gat gga gct cta aac aag tcc act gtc ccc act gac  240
Ile Tyr Thr Phe Asp Gly Ala Leu Asn Lys Ser Thr Val Pro Thr Asp
 65                  70                  75                  80 ttt agt agt gca aaa att gaa gtc tca caa tta cta aaa gga gat gcc  288
Phe Ser Ser Ala Lys Ile Glu Val Ser Gln Leu Leu Lys Gly Asp Ala
                 85                  90                  95 tct ttg aag atg gat aag agt gat gct gtc tca cac aca gga aac tac  336
Ser Leu Lys Met Asp Lys Ser Asp Ala Val Ser His Thr Gly Asn Tyr
            100                 105                 110 act tgt gaa gta aca gaa tta acc aga gaa ggt gaa acg atc atc gag  384
Thr Cys Glu Val Thr Glu Leu Thr Arg Glu Gly Glu Thr Ile Ile Glu
        115                 120                 125 cta aaa tat cgt gtt gtt tca tgg ttt tct cca aat gaa aat gac tac  432
Leu Lys Tyr Arg Val Val Ser Trp Phe Ser Pro Asn Glu Asn Asp Tyr
    130                 135                 140 aag gac gac gat gac aag tgatag                                   456
Lys Asp Asp Asp Asp Lys
145                 150

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 27
ggaattccat atgcaagtgc aacttcaaca gtctggacct gaactg                46

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 28
```

```
ggaattctca ttattttatt tccagcttgg t                                    31

<210> SEQ ID NO 29
<211> LENGTH: 741
<212> TYPE: DNA
<213> ORGANISM: Mus sp.
<220> FEATURE:
<221> NAME/KEY: CDS
<222> LOCATION: (1)..(735)
<223> OTHER INFORMATION: pscM2DEm02. MABL2-scFv

<400> SEQUENCE: 29 atg caa gtg caa ctt caa cag tct gga cct gaa ctg gta aag cct ggg    48
Met Gln Val Gln Leu Gln Gln Ser Gly Pro Glu Leu Val Lys Pro Gly
 1               5                  10                  15 gct tca gtg aag atg tcc tgc aag gct tct gga tac acc ttc gct aac    96
Ala Ser Val Lys Met Ser Cys Lys Ala Ser Gly Tyr Thr Phe Ala Asn
             20                  25                  30 cat gtt att cac tgg gtg aag cag aag cca ggg cag ggc ctt gag tgg   144
His Val Ile His Trp Val Lys Gln Lys Pro Gly Gln Gly Leu Glu Trp
         35                  40                  45 att gga tat att tat cct tac aat gat ggt act aag tat aat gag aag   192
Ile Gly Tyr Ile Tyr Pro Tyr Asn Asp Gly Thr Lys Tyr Asn Glu Lys
     50                  55                  60 ttc aag gac aag gcc act ctg act tca gac aaa tcc tcc acc aca gcc   240
Phe Lys Asp Lys Ala Thr Leu Thr Ser Asp Lys Ser Ser Thr Thr Ala
 65                  70                  75                  80 tac atg gac ctc agc agc ctg gcc tct gag gac tct gcg gtc tat tac   288
Tyr Met Asp Leu Ser Ser Leu Ala Ser Glu Asp Ser Ala Val Tyr Tyr
                 85                  90                  95 tgt gca aga ggg ggt tac tat act tac gac gac tgg ggc caa ggc acc   336
Cys Ala Arg Gly Gly Tyr Tyr Thr Tyr Asp Asp Trp Gly Gln Gly Thr
            100                 105                 110 act ctc aca gtc tcc tca ggt ggt ggt ggt tcg ggt ggt ggt ggt tcg   384
Thr Leu Thr Val Ser Ser Gly Gly Gly Gly Ser Gly Gly Gly Gly Ser
        115                 120                 125 ggt ggt ggc gga tcg gat gtt gtg atg acc caa agt cca ctc tcc ctg   432
Gly Gly Gly Gly Ser Asp Val Val Met Thr Gln Ser Pro Leu Ser Leu
    130                 135                 140 cct gtc agt ctt gga gat caa gcc tcc atc tct tgc aga tca agt cag   480
Pro Val Ser Leu Gly Asp Gln Ala Ser Ile Ser Cys Arg Ser Ser Gln
145                 150                 155                 160 agc ctt gta cac agt aat gga aag acc tat tta cat tgg tac ctg cag   528
Ser Leu Val His Ser Asn Gly Lys Thr Tyr Leu His Trp Tyr Leu Gln
                165                 170                 175 aag cca ggc cag tct cca aaa ctc ctg atc tac aaa gtt tcc aac cga   576
Lys Pro Gly Gln Ser Pro Lys Leu Leu Ile Tyr Lys Val Ser Asn Arg
            180                 185                 190 ttt tct ggg gtc cca gac agg ttc agt ggc agt gga tca gtg aca gat   624
Phe Ser Gly Val Pro Asp Arg Phe Ser Gly Ser Gly Ser Val Thr Asp
        195                 200                 205 ttc aca ctc atg atc agc aga gtg gag gct gag gat ctg gga gtt tat   672
Phe Thr Leu Met Ile Ser Arg Val Glu Ala Glu Asp Leu Gly Val Tyr
    210                 215                 220 ttc tgc tct caa agt aca cat gtt ccg tac acg ttc gga ggg ggg acc   720
Phe Cys Ser Gln Ser Thr His Val Pro Tyr Thr Phe Gly Gly Gly Thr
225                 230                 235                 240 aag ctg gaa ata aaa taatga                                        741
Lys Leu Glu Ile Lys
                245
```

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 30
cagacagtgg ttcaaagt                                                   18

<210> SEQ ID NO 31
<211> LENGTH: 72
<212> TYPE: DNA
<213> ORGANISM: Artificial Sequence
<220> FEATURE:
<223> OTHER INFORMATION: Description of Artificial Sequence: Primer

<400> SEQUENCE: 31
cgcgtcgacc gatccgccac cacccgaacc accaccaccc gaaccaccac cacctttat     60 ttccagcttg gt                                                         72

<210> SEQ ID NO 32
<211> LENGTH: 1605
<212> TYPE: DNA
<213> ORGANISM: Mus sp.
<220> FEATURE:
<221> NAME/KEY: CDS
<222> LOCATION: (1)..(1599)
<223> OTHER INFORMATION: pCHOM2(Fv)2. MABL2-sc(Fv)2

<400> SEQUENCE: 32

| | | |
|---|---|---|
| atg gga tgg agc tgt atc atc ctc ttc ttg gta gca aca gct aca ggt<br>Met Gly Trp Ser Cys Ile Ile Leu Phe Leu Val Ala Thr Ala Thr Gly<br>1               5                   10                  15 | | 48 |
| gtc gac tcc cag gtc cag ctg cag cag tct gga cct gaa ctg gta aag<br>Val Asp Ser Gln Val Gln Leu Gln Gln Ser Gly Pro Glu Leu Val Lys<br>            20                  25                  30 | | 96 |
| cct ggg gct tca gtg aag atg tcc tgc aag gct tct gga tac acc ttc<br>Pro Gly Ala Ser Val Lys Met Ser Cys Lys Ala Ser Gly Tyr Thr Phe<br>        35                  40                  45 | | 144 |
| gct aac cat gtt att cac tgg gtg aag cag aag cca ggg cag ggc ctt<br>Ala Asn His Val Ile His Trp Val Lys Gln Lys Pro Gly Gln Gly Leu<br>    50                  55                  60 | | 192 |
| gag tgg att gga tat att tat cct tac aat gat ggt act aag tat aat<br>Glu Trp Ile Gly Tyr Ile Tyr Pro Tyr Asn Asp Gly Thr Lys Tyr Asn<br>65                  70                  75                  80 | | 240 |
| gag aag ttc aag gac aag gcc act ctg act tca gac aaa tcc tcc acc<br>Glu Lys Phe Lys Asp Lys Ala Thr Leu Thr Ser Asp Lys Ser Ser Thr<br>                85                  90                  95 | | 288 |
| aca gcc tac atg gac ctc agc agc ctg gcc tct gag gac tct gcg gtc<br>Thr Ala Tyr Met Asp Leu Ser Ser Leu Ala Ser Glu Asp Ser Ala Val<br>            100                 105                 110 | | 336 |
| tat tac tgt gca aga ggg ggt tac tat act tac gac gac tgg ggc caa<br>Tyr Tyr Cys Ala Arg Gly Gly Tyr Tyr Thr Tyr Asp Asp Trp Gly Gln<br>        115                 120                 125 | | 384 |
| ggc acc act ctc aca gtc tcc tca ggt ggt ggt ggt tcg ggt ggt ggt<br>Gly Thr Thr Leu Thr Val Ser Ser Gly Gly Gly Gly Ser Gly Gly Gly<br>    130                 135                 140 | | 432 |
| ggt tcg ggt ggt ggc gga tcg gat gtt gtg atg acc caa agt cca ctc<br>Gly Ser Gly Gly Gly Gly Ser Asp Val Val Met Thr Gln Ser Pro Leu<br>145                 150                 155                 160 | | 480 |
| tcc ctg cct gtc agt ctt gga gat caa gcc tcc atc tct tgc aga tca<br> | | 528 |

```
                                      -continued

Ser Leu Pro Val Ser Leu Gly Asp Gln Ala Ser Ile Ser Cys Arg Ser
                165                 170                 175 agt cag agc ctt gtg cac agt aat gga aag acc tat tta cat tgg tac      576
Ser Gln Ser Leu Val His Ser Asn Gly Lys Thr Tyr Leu His Trp Tyr
            180                 185                 190 ctg cag aag cca ggc cag tct cca aaa ctc ctg atc tac aaa gtt tcc      624
Leu Gln Lys Pro Gly Gln Ser Pro Lys Leu Leu Ile Tyr Lys Val Ser
        195                 200                 205 aac cga ttt tct ggg gtc cca gac agg ttc agt ggc agt gga tca gtg      672
Asn Arg Phe Ser Gly Val Pro Asp Arg Phe Ser Gly Ser Gly Ser Val
    210                 215                 220 aca gat ttc aca ctc atg atc agc aga gtg gag gct gag gat ctg gga      720
Thr Asp Phe Thr Leu Met Ile Ser Arg Val Glu Ala Glu Asp Leu Gly
225                 230                 235                 240 gtt tat ttc tgc tct caa agt aca cat gtt ccg tac acg ttc gga ggg      768
Val Tyr Phe Cys Ser Gln Ser Thr His Val Pro Tyr Thr Phe Gly Gly
                245                 250                 255 ggg acc aag ctg gaa ata aaa ggt ggt ggt ggt tcg ggt ggt ggt ggt      816
Gly Thr Lys Leu Glu Ile Lys Gly Gly Gly Gly Ser Gly Gly Gly Gly
            260                 265                 270 tcg ggt ggt ggc gga tcg gtc gac tcc cag gtc cag ctg cag cag tct      864
Ser Gly Gly Gly Gly Ser Val Asp Ser Gln Val Gln Leu Gln Gln Ser
        275                 280                 285 gga cct gaa ctg gta aag cct ggg gct tca gtg aag atg tcc tgc aag      912
Gly Pro Glu Leu Val Lys Pro Gly Ala Ser Val Lys Met Ser Cys Lys
    290                 295                 300 gct tct gga tac acc ttc gct aac cat gtt att cac tgg gtg aag cag      960
Ala Ser Gly Tyr Thr Phe Ala Asn His Val Ile His Trp Val Lys Gln
305                 310                 315                 320 aag cca ggg cag ggc ctt gag tgg att gga tat att tat cct tac aat     1008
Lys Pro Gly Gln Gly Leu Glu Trp Ile Gly Tyr Ile Tyr Pro Tyr Asn
                325                 330                 335 gat ggt act aag tat aat gag aag ttc aag gac aag gcc act ctg act     1056
Asp Gly Thr Lys Tyr Asn Glu Lys Phe Lys Asp Lys Ala Thr Leu Thr
            340                 345                 350 tca gac aaa tcc tcc acc aca gcc tac atg gac ctc agc agc ctg gcc     1104
Ser Asp Lys Ser Ser Thr Thr Ala Tyr Met Asp Leu Ser Ser Leu Ala
        355                 360                 365 tct gag gac tct gcg gtc tat tac tgt gca aga ggg ggt tac tat act     1152
Ser Glu Asp Ser Ala Val Tyr Tyr Cys Ala Arg Gly Gly Tyr Tyr Thr
    370                 375                 380 tac gac gac tgg ggc caa ggc acc act ctc aca gtc tcc tca ggt ggt     1200
Tyr Asp Asp Trp Gly Gln Gly Thr Thr Leu Thr Val Ser Ser Gly Gly
385                 390                 395                 400 ggt ggt tcg ggt ggt ggt ggt tcg ggt ggt ggc gga tcg gat gtt gtg     1248
Gly Gly Ser Gly Gly Gly Gly Ser Gly Gly Gly Gly Ser Asp Val Val
                405                 410                 415 atg acc caa agt cca ctc tcc ctg cct gtc agt ctt gga gat caa gcc     1296
Met Thr Gln Ser Pro Leu Ser Leu Pro Val Ser Leu Gly Asp Gln Ala
            420                 425                 430 tcc atc tct tgc aga tca agt cag agc ctt gtg cac agt aat gga aag     1344
Ser Ile Ser Cys Arg Ser Ser Gln Ser Leu Val His Ser Asn Gly Lys
        435                 440                 445 acc tat tta cat tgg tac ctg cag aag cca ggc cag tct cca aaa ctc     1392
Thr Tyr Leu His Trp Tyr Leu Gln Lys Pro Gly Gln Ser Pro Lys Leu
    450                 455                 460 ctg atc tac aaa gtt tcc aac cga ttt tct ggg gtc cca gac agg ttc     1440
Leu Ile Tyr Lys Val Ser Asn Arg Phe Ser Gly Val Pro Asp Arg Phe
465                 470                 475                 480
```

-continued

```
agt ggc agt gga tca gtg aca gat ttc aca ctc atg atc agc aga gtg      1488
Ser Gly Ser Gly Ser Val Thr Asp Phe Thr Leu Met Ile Ser Arg Val
            485                 490                 495 gag gct gag gat ctg gga gtt tat ttc tgc tct caa agt aca cat gtt      1536
Glu Ala Glu Asp Leu Gly Val Tyr Phe Cys Ser Gln Ser Thr His Val
        500                 505                 510 ccg tac acg ttc gga ggg ggg acc aag ctg gaa ata aaa gac tac aaa      1584
Pro Tyr Thr Phe Gly Gly Gly Thr Lys Leu Glu Ile Lys Asp Tyr Lys
    515                 520                 525 gac gat gac gat aaa taatga                                           1605
Asp Asp Asp Asp Lys
    530
```

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 33
tgaggaattc ccaccatggg atg                                            23

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 34
cacgacgtca ctcgagactg tgagagtggt gccttggccc                          40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 35
agtctcgagt gacgtcgtga tgacccaaag tccactctcc                          40

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 36
gactggatcc tcattattta tcgtcatcgt c                                   31

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 37
cgcgtaatac gactcactat ag                                             22

<210> SEQ ID NO 38
<211> LENGTH: 46

```
<212> TYPE: DNA
<213> ORGANISM: Artificial Sequence
<220> FEATURE:
<223> OTHER INFORMATION: Description of Artificial Sequence: Primer

<400> SEQUENCE: 38
gcaattggac ctgttttatc tcgagcttgg tcccccctcc gaacgt                46

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 39
gctcgagata aaacaggtcc aattgcagca gtctggacct gaact                45

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 40
gactggatcc tcattattta tcgtcatcgt ctttgtagtc tgaggagact gtgagagtgg     60

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 41
gactgaattc ccaccatgaa gttgcctgtt ag                              32

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 42
cagtctcgag tggtggttcc gacgtcgtga tgacccaaag                       40

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 43
cagtctcgag tggtggtggt tccgacgtcg tgatgaccca aag                   43

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 44
```

<210> SEQ ID NO 45
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 45
cagtctcgag tggtggtggt ggtggttccg acgtcgtgat gacccaaag                49

<210> SEQ ID NO 46
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 46
cagtctcgag tggtggtggt ggtggtggtt ccgacgtcgt gatgacccaa ag             52

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
ggccgcatgt tgtcacgaat                                                 20

<210> SEQ ID NO 48
<211> LENGTH: 780
<212> TYPE: DNA
<213> ORGANISM: Mus sp.
<220> FEATURE:
<221> NAME/KEY: CDS
<222> LOCATION: (1)..(768)
<223> OTHER INFORMATION: CF2HL-0/pCOS1. MABL2-scFv<HL-0>

<400> SEQUENCE: 48

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
 1               5                  10                  15 gtc gac tcc cag gtc cag ctg cag cag tct gga cct gaa ctg gta aag      96
Val Asp Ser Gln Val Gln Leu Gln Gln Ser Gly Pro Glu Leu Val Lys
             20                  25                  30 cct ggg gct tca gtg aag atg tcc tgc aag gct tct gga tac acc ttc     144
Pro Gly Ala Ser Val Lys Met Ser Cys Lys Ala Ser Gly Tyr Thr Phe
         35                  40                  45 gct aac cat gtt att cac tgg gtg aag cag aag cca ggg cag ggc ctt     192
Ala Asn His Val Ile His Trp Val Lys Gln Lys Pro Gly Gln Gly Leu
     50                  55                  60 gag tgg att gga tat att tat cct tac aat gat ggt act aag tat aat     240
Glu Trp Ile Gly Tyr Ile Tyr Pro Tyr Asn Asp Gly Thr Lys Tyr Asn
 65                  70                  75                  80 gag aag ttc aag gac aag gcc act ctg act tca gac aaa tcc tcc acc     288
Glu Lys Phe Lys Asp Lys Ala Thr Leu Thr Ser Asp Lys Ser Ser Thr
                 85                  90                  95 aca gcc tac atg gac ctc agc agc ctg gcc tct gag gac tct gcg gtc     336
Thr Ala Tyr Met Asp Leu Ser Ser Leu Ala Ser Glu Asp Ser Ala Val
            100                 105                 110 tat tac tgt gca aga ggg ggt tac tat act tac gac gac tgg ggc caa     384
Tyr Tyr Cys Ala Arg Gly Gly Tyr Tyr Thr Tyr Asp Asp Trp Gly Gln
```

-continued

```
                Tyr Tyr Cys Ala Arg Gly Gly Tyr Tyr Thr Tyr Asp Asp Trp Gly Gln
                        115                 120                 125 ggc acc act ctc aca gtc tcg agt gac gtc gtg atg acc caa agt cca       432
Gly Thr Thr Leu Thr Val Ser Ser Asp Val Val Met Thr Gln Ser Pro
130                 135                 140 ctc tcc ctg cct gtc agt ctt gga gat caa gcc tcc atc tct tgc aga       480
Leu Ser Leu Pro Val Ser Leu Gly Asp Gln Ala Ser Ile Ser Cys Arg
145                 150                 155                 160 tca agt cag agc ctt gtg cac agt aat gga aag acc tat tta cat tgg       528
Ser Ser Gln Ser Leu Val His Ser Asn Gly Lys Thr Tyr Leu His Trp
                165                 170                 175 tac ctg cag aag cca ggc cag tct cca aaa ctc ctg atc tac aaa gtt       576
Tyr Leu Gln Lys Pro Gly Gln Ser Pro Lys Leu Leu Ile Tyr Lys Val
                180                 185                 190 tcc aac cga ttt tct ggg gtc cca gac agg ttc agt ggc agt gga tca       624
Ser Asn Arg Phe Ser Gly Val Pro Asp Arg Phe Ser Gly Ser Gly Ser
                195                 200                 205 gtg aca gat ttc aca ctc atg atc agc aga gtg gag gct gag gat ctg       672
Val Thr Asp Phe Thr Leu Met Ile Ser Arg Val Glu Ala Glu Asp Leu
        210                 215                 220 gga gtt tat ttc tgc tct caa agt aca cat gtt ccg tac acg ttc gga       720
Gly Val Tyr Phe Cys Ser Gln Ser Thr His Val Pro Tyr Thr Phe Gly
225                 230                 235                 240 ggg ggg acc aag ctg gaa ata aaa gac tac aaa gac gat gac gat aaa       768
Gly Gly Thr Lys Leu Glu Ile Lys Asp Tyr Lys Asp Asp Asp Asp Lys
                        245                 250                 255 taatgaggat cc                                                         780

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 49
caagctcgag ataaaatccg gaggccaggt ccaattgcag cagtc                     45

<210> SEQ ID NO 50
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 50
caagctcgag ataaaatccg gaggtggcca ggtccaattg cagcagtc                  48

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 51
caagctcgag ataaaatccg gaggtggtgg ccaggtccaa ttgcagcagt c              51

<210> SEQ ID NO 52
<211> LENGTH: 54
<212> TYPE: DNA
<213> ORGANISM: Artificial Sequence
<220> FEATURE:
```

<223> OTHER INFORMATION: Description of Artificial Sequence: Primer

<400> SEQUENCE: 52
caagctcgag ataaaatccg gaggtggtgg tggccaggtc caattgcagc agtc      54

<210> SEQ ID NO 53
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 53
caagctcgag ataaaatccg gaggtggtgg tggtggccag gtccaattgc agcagtc    57

<210> SEQ ID NO 54
<211> LENGTH: 780
<212> TYPE: DNA
<213> ORGANISM: Mus sp.
<220> FEATURE:
<221> NAME/KEY: CDS
<222> LOCATION: (1)..(768)
<223> OTHER INFORMATION: CF2LH-0/pCOS1. MABL2-scFv<LH-0>

<400> SEQUENCE: 54

| atg aag ttg cct gtt agg ctg ttg gtg ctg atg ttc tgg att cct ggt | 48 |
| Met Lys Leu Pro Val Arg Leu Leu Val Leu Met Phe Trp Ile Pro Gly | |
| 1               5                   10                  15     | |

| tcc agc agt gat gtt gtg atg acc caa agt cca ctc tcc ctg cct gtc | 96 |
| Ser Ser Ser Asp Val Val Met Thr Gln Ser Pro Leu Ser Leu Pro Val | |
|                 20                  25                  30     | |

| agt ctt gga gat caa gcc tcc atc tct tgc aga tca agt cag agc ctt | 144 |
| Ser Leu Gly Asp Gln Ala Ser Ile Ser Cys Arg Ser Ser Gln Ser Leu | |
|         35                  40                  45             | |

| gtg cac agt aat gga aag acc tat tta cat tgg tac ctg cag aag cca | 192 |
| Val His Ser Asn Gly Lys Thr Tyr Leu His Trp Tyr Leu Gln Lys Pro | |
| 50                  55                  60                     | |

| ggc cag tct cca aaa ctc ctg atc tac aaa gtt tcc aac cga ttt tct | 240 |
| Gly Gln Ser Pro Lys Leu Leu Ile Tyr Lys Val Ser Asn Arg Phe Ser | |
| 65                  70                  75                  80 | |

| ggg gtc cca gac agg ttc agt ggc agt gga tca gtg aca gat ttc aca | 288 |
| Gly Val Pro Asp Arg Phe Ser Gly Ser Gly Ser Val Thr Asp Phe Thr | |
|                 85                  90                  95     | |

| ctc atg atc agc aga gtg gag gct gag gat ctg gga gtt tat ttc tgc | 336 |
| Leu Met Ile Ser Arg Val Glu Ala Glu Asp Leu Gly Val Tyr Phe Cys | |
|         100                 105                 110            | |

| tct caa agt aca cat gtt ccg tac acg ttc gga ggg ggg acc aag ctc | 384 |
| Ser Gln Ser Thr His Val Pro Tyr Thr Phe Gly Gly Gly Thr Lys Leu | |
|     115                 120                 125                | |

| gag ata aaa cag gtc caa ttg cag cag tct gga cct gaa ctg gta aag | 432 |
| Glu Ile Lys Gln Val Gln Leu Gln Gln Ser Gly Pro Glu Leu Val Lys | |
| 130                 135                 140                    | |

| cct ggg gct tca gtg aag atg tcc tgc aag gct tct gga tac acc ttc | 480 |
| Pro Gly Ala Ser Val Lys Met Ser Cys Lys Ala Ser Gly Tyr Thr Phe | |
| 145                 150                 155                 160 | |

| gct aac cat gtt att cac tgg gtg aag cag aag cca ggg cag ggc ctt | 528 |
| Ala Asn His Val Ile His Trp Val Lys Gln Lys Pro Gly Gln Gly Leu | |
|                 165                 170                 175    | |

| gag tgg att gga tat att tat cct tac aat gat ggt act aag tat aat | 576 |
| Glu Trp Ile Gly Tyr Ile Tyr Pro Tyr Asn Asp Gly Thr Lys Tyr Asn | |
|             180                 185                 190        | |

| gag aag ttc aag gac aag gcc act ctg act tca gac aaa tcc tcc acc | 624 |

```
                Glu Lys Phe Lys Asp Lys Ala Thr Leu Thr Ser Asp Lys Ser Ser Thr
                    195                 200                 205 aca gcc tac atg gac ctc agc agc ctg gcc tct gag gac tct gcg gtc      672
Thr Ala Tyr Met Asp Leu Ser Ser Leu Ala Ser Glu Asp Ser Ala Val
    210                 215                 220 tat tac tgt gca aga ggg ggt tac tat act tac gac gac tgg ggc caa      720
Tyr Tyr Cys Ala Arg Gly Gly Tyr Tyr Thr Tyr Asp Asp Trp Gly Gln
225                 230                 235                 240 ggc acc act ctc aca gtc tcc tca gac tac aaa gac gat gac gat aaa      768
Gly Thr Thr Leu Thr Val Ser Ser Asp Tyr Lys Asp Asp Asp Asp Lys
                245                 250                 255 taatgaggat cc                                                        780

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Linker
      peptide

<400> SEQUENCE: 55

Gly Gly Gly Gly Ser Gly Gly Gly Ser Gly Gly Gly Gly Ser Val
1               5                   10                  15
Asp Ser

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(18)

<400> SEQUENCE: 56 gtc tcg agt gac gtc gtg                                               18
Val Ser Ser Asp Val Val
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 57

Val Ser Ser Asp Val Val
1               5

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(27)

<400> SEQUENCE: 58
```

```
gtc tcg agt ggt ggt tcc gac gtc gtg                              27
Val Ser Ser Gly Gly Ser Asp Val Val
 1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 59

Val Ser Ser Gly Gly Ser Asp Val Val
 1               5

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(30)

<400> SEQUENCE: 60 gtc tcg agt ggt ggt ggt tcc gac gtc gtg                          30
Val Ser Ser Gly Gly Gly Ser Asp Val Val
 1               5                  10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 61

Val Ser Ser Gly Gly Gly Ser Asp Val Val
 1               5                  10

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(33)

<400> SEQUENCE: 62 gtc tcg agt ggt ggt ggt ggt tcc gac gtc gtg                      33
Val Ser Ser Gly Gly Gly Gly Ser Asp Val Val
 1               5                  10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 63
```

```
Val Ser Ser Gly Gly Gly Gly Ser Asp Val Val
 1               5                  10
```

```
<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(36)

<400> SEQUENCE: 64
```

```
gtc tcg agt ggt ggt ggt ggt ggt tcc gac gtc gtg        36
Val Ser Ser Gly Gly Gly Gly Gly Ser Asp Val Val
 1               5                  10
```

```
<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 65
```

```
Val Ser Ser Gly Gly Gly Gly Gly Ser Asp Val Val
 1               5                  10
```

```
<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(39)

<400> SEQUENCE: 66
```

```
gtc tcg agt ggt ggt ggt ggt ggt ggt tcc gac gtc gtg    39
Val Ser Ser Gly Gly Gly Gly Gly Gly Ser Asp Val Val
 1               5                  10
```

```
<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 67
```

```
Val Ser Ser Gly Gly Gly Gly Gly Gly Ser Asp Val Val
 1               5                  10
```

```
<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(18)
```

-continued

```
<400> SEQUENCE: 68 gag ata aaa cag gtc caa                                              18
Glu Ile Lys Gln Val Gln
  1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 69

Glu Ile Lys Gln Val Gln
  1               5

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(27)

<400> SEQUENCE: 70 gag ata aaa tcc gga ggc cag gtc caa                                  27
Glu Ile Lys Ser Gly Gly Gln Val Gln
  1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 71

Glu Ile Lys Ser Gly Gly Gln Val Gln
  1               5

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(30)

<400> SEQUENCE: 72 gag ata aaa tcc gga ggt ggc cag gtc caa                              30
Glu Ile Lys Ser Gly Gly Gly Gln Val Gln
  1               5                  10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence:
      Plasmid/linker peptide sequence
```

<400> SEQUENCE: 73

Glu Ile Lys Ser Gly Gly Gly Gln Val Gln
 1               5                  10

<210> SEQ ID NO 74
<211> LENGTH: 33
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(33)

<400> SEQUENCE: 74 gag ata aaa tcc gga ggt ggt ggc cag gtc caa                          33
Glu Ile Lys Ser Gly Gly Gly Gly Gln Val Gln
 1               5                  10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 75

Glu Ile Lys Ser Gly Gly Gly Gly Gln Val Gln
 1               5                  10

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS
<222> LOCATION: (1)..(36)

<400> SEQUENCE: 76 gag ata aaa tcc gga ggt ggt ggt ggc cag gtc caa                      36
Glu Ile Lys Ser Gly Gly Gly Gly Gly Gln Val Gln
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 77

Glu Ile Lys Ser Gly Gly Gly Gly Gly Gln Val Gln
 1               5                  10

<210> SEQ ID NO 78
<211> LENGTH: 39
<212> TYPE: DNA
<213> ORGANISM: Artificial Sequence
<220> FEATURE:
<223> OTHER INFORMATION: Description of Artificial Sequence:
      Plasmid/linker nucleotide sequence
<220> FEATURE:
<221> NAME/KEY: CDS

<222> LOCATION: (1)..(39)

<400> SEQUENCE: 78

```
gag ata aaa tcc gga ggt ggt ggt ggt ggc cag gtc caa       39
Glu Ile Lys Ser Gly Gly Gly Gly Gly Gly Gln Val Gln
 1               5                  10
```

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence:
      Plasmid/linker peptide sequence

<400> SEQUENCE: 79

```
Glu Ile Lys Ser Gly Gly Gly Gly Gly Gly Gln Val Gln
 1               5                  10
```

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Linker
      peptide

<400> SEQUENCE: 80

```
Gly Gly Gly Ser
 1
```

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Linker
      peptide

<400> SEQUENCE: 81

```
Ser Gly Gly Gly
 1
```

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 82

```
Gly Gly Gly Gly Ser
 1               5
```

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 83

```
Ser Gly Gly Gly Gly
 1               5
```

```
<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 84

Gly Gly Gly Gly Gly Ser
 1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 85

Ser Gly Gly Gly Gly Gly
 1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Linker
      peptide

<400> SEQUENCE: 86

Gly Gly Gly Gly Gly Gly Ser
 1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Linker
      peptide

<400> SEQUENCE: 87

Ser Gly Gly Gly Gly Gly Gly
 1               5

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Linker
      peptide
<220> FEATURE:
<223> OTHER INFORMATION: this sequence may encompass 5-15 residues; for
      preferred embodiments see specification as filed

<400> SEQUENCE: 88

Gly Gly Gly Gly Ser Gly Gly Gly Gly Ser Gly Gly Gly Gly Ser
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Linker
```

```
            peptide
<220> FEATURE:
<223> OTHER INFORMATION: this sequence may encompass 5-15 residues; for
      preferred embodiments see specification as filed

<400> SEQUENCE: 89

Ser Gly Gly Gly Gly Ser Gly Gly Gly Gly Ser Gly Gly Gly Gly
 1               5                  10                  15

<210> SEQ ID NO 90
<211> LENGTH: 131
<212> TYPE: PRT
<213> ORGANISM: Mus sp.
<220> FEATURE:
<223> OTHER INFORMATION: pGEM-M1L

<400> SEQUENCE: 90

Met Lys Leu Pro Val Arg Leu Leu Val Leu Met Phe Trp Ile Pro Ala
                -15                 -10                 -5

Ser Ser Ser Asp Val Val Met Thr Gln Thr Pro Leu Ser Leu Pro Val
            -1   1               5                  10

Ser Leu Gly Asp Gln Ala Ser Ile Ser Cys Arg Ser Ser Gln Ser Leu
         15                  20                  25

Leu His Ser Lys Gly Asn Thr Tyr Leu Gln Trp Tyr Leu Gln Lys Pro
 30                  35                  40                  45

Gly Gln Ser Pro Lys Leu Leu Ile Tyr Lys Val Ser Asn Arg Phe Ser
                 50                  55                  60

Gly Val Pro Asp Arg Phe Ser Gly Ser Gly Ser Gly Thr Asp Phe Thr
             65                  70                  75

Leu Lys Ile Ser Arg Val Glu Ala Glu Asp Leu Gly Val Tyr Phe Cys
         80                  85                  90

Ser Gln Ser Thr His Val Pro Tyr Thr Ser Gly Gly Thr Lys Leu
     95                 100                 105

Glu Ile Lys
110

<210> SEQ ID NO 91
<211> LENGTH: 136
<212> TYPE: PRT
<213> ORGANISM: Mus sp.
<220> FEATURE:
<223> OTHER INFORMATION: pGEM-M1H

<400> SEQUENCE: 91

Met Glu Trp Ser Trp Ile Phe Leu Phe Leu Leu Ser Gly Thr Ala Gly
                -15                 -10                 -5

Val His Ser Gln Val Gln Leu Gln Gln Ser Gly Pro Asp Leu Val Lys
            -1   1               5                  10

Pro Gly Ala Ser Val Lys Met Ser Cys Lys Ala Ser Gly Tyr Thr Phe
         15                  20                  25

Val Asn His Val Met His Trp Val Lys Gln Lys Pro Gly Gln Gly Leu
 30                  35                  40                  45

Glu Trp Ile Gly Tyr Ile Tyr Pro Tyr Asn Asp Gly Thr Lys Tyr Asn
                 50                  55                  60

Glu Lys Phe Lys Gly Lys Ala Thr Leu Thr Ser Glu Lys Ser Ser Ser
             65                  70                  75

Ala Ala Tyr Met Glu Leu Ser Ser Leu Ala Ser Glu Asp Ser Ala Val
         80                  85                  90

Tyr Tyr Cys Ala Arg Gly Gly Tyr Tyr Ser Tyr Asp Asp Trp Gly Gln
```

```
                 95                 100                 105
Gly Thr Thr Leu Thr Val Ser Ser
110                 115

<210> SEQ ID NO 92
<211> LENGTH: 131
<212> TYPE: PRT
<213> ORGANISM: Mus sp.
<220> FEATURE:
<223> OTHER INFORMATION: pGEM-M2L

<400> SEQUENCE: 92

Met Lys Leu Pro Val Arg Leu Leu Val Leu Met Phe Trp Ile Pro Gly
                -15                 -10                  -5

Ser Ser Ser Asp Val Val Met Thr Gln Ser Pro Leu Ser Leu Pro Val
             -1   1                  5                  10

Ser Leu Gly Asp Gln Ala Ser Ile Ser Cys Arg Ser Ser Gln Ser Leu
         15                  20                  25

Val His Ser Asn Gly Lys Thr Tyr Leu His Trp Tyr Leu Gln Lys Pro
 30                  35                  40                  45

Gly Gln Ser Pro Lys Leu Leu Ile Tyr Lys Val Ser Asn Arg Phe Ser
                 50                  55                  60

Gly Val Pro Asp Arg Phe Ser Gly Ser Gly Ser Val Thr Asp Phe Thr
             65                  70                  75

Leu Met Ile Ser Arg Val Glu Ala Glu Asp Leu Gly Val Tyr Phe Cys
         80                  85                  90

Ser Gln Ser Thr His Val Pro Tyr Thr Phe Gly Gly Gly Thr Lys Leu
     95                 100                 105

Glu Ile Lys
110

<210> SEQ ID NO 93
<211> LENGTH: 136
<212> TYPE: PRT
<213> ORGANISM: Mus sp.
<220> FEATURE:
<223> OTHER INFORMATION: pGEM-M2H

<400> SEQUENCE: 93

Met Glu Trp Ser Trp Ile Phe Leu Phe Leu Leu Ser Gly Thr Ala Gly
                -15                 -10                  -5

Val His Ser Gln Val Gln Leu Gln Gln Ser Gly Pro Glu Leu Val Lys
             -1   1                  5                  10

Pro Gly Ala Ser Val Lys Met Ser Cys Lys Ala Ser Gly Tyr Thr Phe
         15                  20                  25

Ala Asn His Val Ile His Trp Val Lys Gln Lys Pro Gly Gln Gly Leu
 30                  35                  40                  45

Glu Trp Ile Gly Tyr Ile Tyr Pro Tyr Asn Asp Gly Thr Lys Tyr Asn
                 50                  55                  60

Glu Lys Phe Lys Asp Lys Ala Thr Leu Thr Ser Asp Lys Ser Ser Thr
             65                  70                  75

Thr Ala Tyr Met Asp Leu Ser Ser Leu Ala Ser Glu Asp Ser Ala Val
         80                  85                  90

Tyr Tyr Cys Ala Arg Gly Gly Tyr Tyr Thr Tyr Asp Asp Trp Gly Gln
     95                 100                 105

Gly Thr Thr Leu Thr Val Ser Ser
110                 115
```

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Linker
      peptide

<400> SEQUENCE: 94

Gly Gly Gly Gly Ser Gly Gly Gly Gly Ser Gly Gly Gly Gly Ser
 1               5                  10                  15

<210> SEQ ID NO 95
<211> LENGTH: 271
<212> TYPE: PRT
<213> ORGANISM: Mus sp.
<220> FEATURE:
<223> OTHER INFORMATION: pscM1. MABL1-scFv

<400> SEQUENCE: 95

Met Lys Tyr Leu Leu Pro Thr Ala Ala Ala Gly Leu Leu Leu Ala
 1               5                  10                  15

Ala Gln Pro Ala Met Ala Gln Val Gln Leu Gln Gln Ser Gly Pro Asp
             20                  25                  30

Leu Val Lys Pro Gly Ala Ser Val Lys Met Ser Cys Lys Ala Ser Gly
         35                  40                  45

Tyr Thr Phe Val Asn His Val Met His Trp Val Lys Gln Lys Pro Gly
     50                  55                  60

Gln Gly Leu Glu Trp Ile Gly Tyr Ile Tyr Pro Tyr Asn Asp Gly Thr
 65                  70                  75                  80

Lys Tyr Asn Glu Lys Phe Lys Gly Lys Ala Thr Leu Thr Ser Glu Lys
                 85                  90                  95

Ser Ser Ser Ala Ala Tyr Met Glu Leu Ser Ser Leu Ala Ser Glu Asp
            100                 105                 110

Ser Ala Val Tyr Tyr Cys Ala Arg Gly Gly Tyr Tyr Ser Tyr Asp Asp
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Gly Ser Asp Val Val Met Thr Gln
145                 150                 155                 160

Thr Pro Leu Ser Leu Pro Val Ser Leu Gly Asp Gln Ala Ser Ile Ser
                165                 170                 175

Cys Arg Ser Ser Gln Ser Leu Leu His Ser Lys Gly Asn Thr Tyr Leu
            180                 185                 190

Gln Trp Tyr Leu Gln Lys Pro Gly Gln Ser Pro Lys Leu Leu Ile Tyr
        195                 200                 205

Lys Val Ser Asn Arg Phe Ser Gly Val Pro Asp Arg Phe Ser Gly Ser
    210                 215                 220

Gly Ser Gly Thr Asp Phe Thr Leu Lys Ile Ser Arg Val Glu Ala Glu
225                 230                 235                 240

Asp Leu Gly Val Tyr Phe Cys Ser Gln Ser Thr His Val Pro Tyr Thr
                245                 250                 255

Ser Gly Gly Gly Thr Lys Leu Glu Ile Lys Asp Tyr Lys Asp Asp
            260                 265                 270

<210> SEQ ID NO 96
<211> LENGTH: 271
<212> TYPE: PRT

<213> ORGANISM: Mus sp.
<220> FEATURE:
<223> OTHER INFORMATION: pCHOM1. MABL1-scFv

<400> SEQUENCE: 96

Met Gly Trp Ser Cys Ile Ile Leu Phe Leu Val Ala Thr Ala Thr Gly
1               5                   10                  15

Val Asp Ser Gln Val Gln Leu Gln Gln Ser Gly Pro Asp Leu Val Lys
            20                  25                  30

Pro Gly Ala Ser Val Lys Met Ser Cys Lys Ala Ser Gly Tyr Thr Phe
        35                  40                  45

Val Asn His Val Met His Trp Val Lys Gln Lys Pro Gly Gln Gly Leu
    50                  55                  60

Glu Trp Ile Gly Tyr Ile Tyr Pro Tyr Asn Asp Gly Thr Lys Tyr Asn
65                  70                  75                  80

Glu Lys Phe Lys Gly Lys Ala Thr Leu Thr Ser Glu Lys Ser Ser Ser
                85                  90                  95

Ala Ala Tyr Met Glu Leu Ser Ser Leu Ala Ser Glu Asp Ser Ala Val
            100                 105                 110

Tyr Tyr Cys Ala Arg Gly Gly Tyr Tyr Ser Tyr Asp Asp Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Val Val Met Thr Gln Thr Pro Leu
145                 150                 155                 160

Ser Leu Pro Val Ser Leu Gly Asp Gln Ala Ser Ile Ser Cys Arg Ser
                165                 170                 175

Ser Gln Ser Leu Leu His Ser Lys Gly Asn Thr Tyr Leu Gln Trp Tyr
            180                 185                 190

Leu Gln Lys Pro Gly Gln Ser Pro Lys Leu Leu Ile Tyr Lys Val Ser
        195                 200                 205

Asn Arg Phe Ser Gly Val Pro Asp Arg Phe Ser Gly Ser Gly Ser Gly
    210                 215                 220

Thr Asp Phe Thr Leu Lys Ile Ser Arg Val Glu Ala Glu Asp Leu Gly
225                 230                 235                 240

Val Tyr Phe Cys Ser Gln Ser Thr His Val Pro Tyr Thr Ser Gly Gly
                245                 250                 255

Gly Thr Lys Leu Glu Ile Lys Asp Tyr Lys Asp Asp Asp Asp Lys
            260                 265                 270

<210> SEQ ID NO 97
<211> LENGTH: 274
<212> TYPE: PRT
<213> ORGANISM: Mus sp.
<220> FEATURE:
<223> OTHER INFORMATION: pscM2. MABL2-scFv

<400> SEQUENCE: 97

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Pro Glu
            20                  25                  30

Leu Val Lys Pro Gly Ala Ser Val Lys Met Ser Cys Lys Ala Ser Gly
        35                  40                  45

Tyr Thr Phe Ala Asn His Val Ile His Trp Val Lys Gln Lys Pro Gly
    50                  55                  60

-continued

```
Gln Gly Leu Glu Trp Ile Gly Tyr Ile Tyr Pro Tyr Asn Asp Gly Thr
 65                  70                  75                  80

Lys Tyr Asn Glu Lys Phe Lys Asp Lys Ala Thr Leu Thr Ser Asp Lys
                 85                  90                  95

Ser Ser Thr Thr Ala Tyr Met Asp Leu Ser Ser Leu Ala Ser Glu Asp
            100                 105                 110

Ser Ala Val Tyr Tyr Cys Ala Arg Gly Gly Tyr Tyr Thr Tyr Asp Asp
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Asp Val Val Met Thr Gln
145                 150                 155                 160

Ser Pro Leu Ser Leu Pro Val Ser Leu Gly Asp Gln Ala Ser Ile Ser
                165                 170                 175

Cys Arg Ser Ser Gln Ser Leu Val His Ser Asn Gly Lys Thr Tyr Leu
            180                 185                 190

His Trp Tyr Leu Gln Lys Pro Gly Gln Ser Pro Lys Leu Leu Ile Tyr
        195                 200                 205

Lys Val Ser Asn Arg Phe Ser Gly Val Pro Asp Arg Phe Ser Gly Ser
    210                 215                 220

Gly Ser Val Thr Asp Phe Thr Leu Met Ile Ser Arg Val Glu Ala Glu
225                 230                 235                 240

Asp Leu Gly Val Tyr Phe Cys Ser Gln Ser Thr His Val Pro Tyr Thr
                245                 250                 255

Phe Gly Gly Gly Thr Lys Leu Glu Ile Lys Asp Tyr Lys Asp Asp Asp
            260                 265                 270

Asp Lys
```

<210> SEQ ID NO 98
<211> LENGTH: 271
<212> TYPE: PRT
<213> ORGANISM: Mus sp.
<220> FEATURE:
<223> OTHER INFORMATION: pCHOM2. MABL2-scFv

<400> SEQUENCE: 98

```
Met Gly Trp Ser Cys Ile Ile Leu Phe Leu Val Ala Thr Ala Thr Gly
  1               5                  10                  15

Val Asp Ser Gln Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Ala Asn His Val Ile His Trp Val Lys Gln Lys Pro Gly Gln Gly Leu
     50                  55                  60

Glu Trp Ile Gly Tyr Ile Tyr Pro Tyr Asn Asp Gly Thr Lys Tyr Asn
 65                  70                  75                  80

Glu Lys Phe Lys Asp Lys Ala Thr Leu Thr Ser Asp Lys Ser Ser Thr
                 85                  90                  95

Thr Ala Tyr Met Asp Leu Ser Ser Leu Ala Ser Glu Asp Ser Ala Val
            100                 105                 110

Tyr Tyr Cys Ala Arg Gly Gly Tyr Tyr Thr Tyr Asp Asp Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Val Val Met Thr Gln Ser Pro Leu
```

145                 150                 155                 160

Ser Leu Pro Val Ser Leu Gly Asp Gln Ala Ser Ile Ser Cys Arg Ser
                165                 170                 175

Ser Gln Ser Leu Val His Ser Asn Gly Lys Thr Tyr Leu His Trp Tyr
            180                 185                 190

Leu Gln Lys Pro Gly Gln Ser Pro Lys Leu Leu Ile Tyr Lys Val Ser
            195                 200                 205

Asn Arg Phe Ser Gly Val Pro Asp Arg Phe Ser Gly Ser Gly Ser Val
        210                 215                 220

Thr Asp Phe Thr Leu Met Ile Ser Arg Val Glu Ala Glu Asp Leu Gly
225                 230                 235                 240

Val Tyr Phe Cys Ser Gln Ser Thr His Val Pro Tyr Thr Phe Gly Gly
                245                 250                 255

Gly Thr Lys Leu Glu Ile Lys Asp Tyr Lys Asp Asp Asp Lys
            260                 265                 270

<210> SEQ ID NO 99
<211> LENGTH: 150
<212> TYPE: PRT
<213> ORGANISM: Mus sp.
<220> FEATURE:
<223> OTHER INFORMATION: pCHO-shIAP. Soluble human IAP

<400> SEQUENCE: 99

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Asp Tyr
    130                 135                 140

Lys Asp Asp Asp Lys
145                 150

<210> SEQ ID NO 100
<211> LENGTH: 245
<212> TYPE: PRT
<213> ORGANISM: Mus sp.
<220> FEATURE:
<223> OTHER INFORMATION: pscM2DEm02. MABL2-scFv

<400> SEQUENCE: 100

Met Gln Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Ala Asn
            20                  25                  30

```
His Val Ile His Trp Val Lys Gln Lys Pro Gly Gln Gly Leu Glu Trp
            35                  40                  45
Ile Gly Tyr Ile Tyr Pro Tyr Asn Asp Gly Thr Lys Tyr Asn Glu Lys
        50                  55                  60
Phe Lys Asp Lys Ala Thr Leu Thr Ser Asp Lys Ser Ser Thr Thr Ala
 65                  70                  75                  80
Tyr Met Asp Leu Ser Ser Leu Ala Ser Glu Asp Ser Ala Val Tyr Tyr
                85                  90                  95
Cys Ala Arg Gly Gly Tyr Tyr Thr Tyr Asp Asp Trp Gly Gln Gly Thr
            100                 105                 110
Thr Leu Thr Val Ser Ser Gly Gly Gly Gly Ser Gly Gly Gly Gly Ser
        115                 120                 125
Gly Gly Gly Gly Ser Asp Val Val Met Thr Gln Ser Pro Leu Ser Leu
    130                 135                 140
Pro Val Ser Leu Gly Asp Gln Ala Ser Ile Ser Cys Arg Ser Ser Gln
145                 150                 155                 160
Ser Leu Val His Ser Asn Gly Lys Thr Tyr Leu His Trp Tyr Leu Gln
                165                 170                 175
Lys Pro Gly Gln Ser Pro Lys Leu Leu Ile Tyr Lys Val Ser Asn Arg
            180                 185                 190
Phe Ser Gly Val Pro Asp Arg Phe Ser Gly Ser Gly Ser Val Thr Asp
        195                 200                 205
Phe Thr Leu Met Ile Ser Arg Val Glu Ala Glu Asp Leu Gly Val Tyr
    210                 215                 220
Phe Cys Ser Gln Ser Thr His Val Pro Tyr Thr Phe Gly Gly Gly Thr
225                 230                 235                 240
Lys Leu Glu Ile Lys
                245

<210> SEQ ID NO 101
<211> LENGTH: 533
<212> TYPE: PRT
<213> ORGANISM: Mus sp.
<220> FEATURE:
<223> OTHER INFORMATION: pCHOM2(Fv)2. MABL2-sc(Fv)2

<400> SEQUENCE: 101

Met Gly Trp Ser Cys Ile Ile Leu Phe Leu Val Ala Thr Ala Thr Gly
 1               5                  10                  15
Val Asp Ser Gln Val Gln Leu Gln Gln Ser Gly Pro Glu Leu Val Lys
            20                  25                  30
Pro Gly Ala Ser Val Lys Met Ser Cys Lys Ala Ser Gly Tyr Thr Phe
        35                  40                  45
Ala Asn His Val Ile His Trp Val Lys Gln Lys Pro Gly Gln Gly Leu
    50                  55                  60
Glu Trp Ile Gly Tyr Ile Tyr Pro Tyr Asn Asp Gly Thr Lys Tyr Asn
 65                  70                  75                  80
Glu Lys Phe Lys Asp Lys Ala Thr Leu Thr Ser Asp Lys Ser Ser Thr
                85                  90                  95
Thr Ala Tyr Met Asp Leu Ser Ser Leu Ala Ser Glu Asp Ser Ala Val
            100                 105                 110
Tyr Tyr Cys Ala Arg Gly Gly Tyr Tyr Thr Tyr Asp Asp Trp Gly Gln
        115                 120                 125
Gly Thr Thr Leu Thr Val Ser Ser Gly Gly Gly Gly Ser Gly Gly Gly
    130                 135                 140
```

-continued

```
Gly Ser Gly Gly Gly Ser Asp Val Val Met Thr Gln Ser Pro Leu
145                 150                 155                 160

Ser Leu Pro Val Ser Leu Gly Asp Gln Ala Ser Ile Ser Cys Arg Ser
            165                 170                 175

Ser Gln Ser Leu Val His Ser Asn Gly Lys Thr Tyr Leu His Trp Tyr
        180                 185                 190

Leu Gln Lys Pro Gly Gln Ser Pro Lys Leu Leu Ile Tyr Lys Val Ser
    195                 200                 205

Asn Arg Phe Ser Gly Val Pro Asp Arg Phe Ser Gly Ser Gly Ser Val
210                 215                 220

Thr Asp Phe Thr Leu Met Ile Ser Arg Val Glu Ala Glu Asp Leu Gly
225                 230                 235                 240

Val Tyr Phe Cys Ser Gln Ser Thr His Val Pro Tyr Thr Phe Gly Gly
            245                 250                 255

Gly Thr Lys Leu Glu Ile Lys Gly Gly Gly Ser Gly Gly Gly
            260                 265                 270

Ser Gly Gly Gly Ser Val Asp Ser Gln Val Gln Leu Gln Gln Ser
    275                 280                 285

Gly Pro Glu Leu Val Lys Pro Gly Ala Ser Val Lys Met Ser Cys Lys
    290                 295                 300

Ala Ser Gly Tyr Thr Phe Ala Asn His Val Ile His Trp Val Lys Gln
305                 310                 315                 320

Lys Pro Gly Gln Gly Leu Glu Trp Ile Gly Tyr Ile Pro Tyr Asn
            325                 330                 335

Asp Gly Thr Lys Tyr Asn Glu Lys Phe Lys Asp Lys Ala Thr Leu Thr
            340                 345                 350

Ser Asp Lys Ser Ser Thr Thr Ala Tyr Met Asp Leu Ser Ser Leu Ala
    355                 360                 365

Ser Glu Asp Ser Ala Val Tyr Tyr Cys Ala Arg Gly Gly Tyr Tyr Thr
    370                 375                 380

Tyr Asp Asp Trp Gly Gln Gly Thr Thr Leu Thr Val Ser Ser Gly Gly
385                 390                 395                 400

Gly Gly Ser Gly Gly Gly Ser Gly Gly Gly Ser Asp Val Val
            405                 410                 415

Met Thr Gln Ser Pro Leu Ser Leu Pro Val Ser Leu Gly Asp Gln Ala
            420                 425                 430

Ser Ile Ser Cys Arg Ser Ser Gln Ser Leu Val His Ser Asn Gly Lys
    435                 440                 445

Thr Tyr Leu His Trp Tyr Leu Gln Lys Pro Gly Gln Ser Pro Lys Leu
    450                 455                 460

Leu Ile Tyr Lys Val Ser Asn Arg Phe Ser Gly Val Pro Asp Arg Phe
465                 470                 475                 480

Ser Gly Ser Gly Ser Val Thr Asp Phe Thr Leu Met Ile Ser Arg Val
            485                 490                 495

Glu Ala Glu Asp Leu Gly Val Tyr Phe Cys Ser Gln Ser Thr His Val
            500                 505                 510

Pro Tyr Thr Phe Gly Gly Gly Thr Lys Leu Glu Ile Lys Asp Tyr Lys
            515                 520                 525

Asp Asp Asp Asp Lys
            530
```

<210> SEQ ID NO 102
<211> LENGTH: 256
<212> TYPE: PRT

<213> ORGANISM: Mus sp.
<220> FEATURE:
<223> OTHER INFORMATION: CF2HL-0/pCOS1. MABL2-scFv<HL-0>

<400> SEQUENCE: 102

```
Met Gly Trp Ser Cys Ile Ile Leu Phe Leu Val Ala Thr Ala Thr Gly
 1               5                  10                  15

Val Asp Ser Gln Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Ala Asn His Val Ile His Trp Val Lys Gln Lys Pro Gly Gln Gly Leu
    50                  55                  60

Glu Trp Ile Gly Tyr Ile Tyr Pro Tyr Asn Asp Gly Thr Lys Tyr Asn
65                  70                  75                  80

Glu Lys Phe Lys Asp Lys Ala Thr Leu Thr Ser Asp Lys Ser Ser Thr
                85                  90                  95

Thr Ala Tyr Met Asp Leu Ser Ser Leu Ala Ser Glu Asp Ser Ala Val
            100                 105                 110

Tyr Tyr Cys Ala Arg Gly Gly Tyr Tyr Thr Tyr Asp Asp Trp Gly Gln
        115                 120                 125

Gly Thr Thr Leu Thr Val Ser Ser Asp Val Val Met Thr Gln Ser Pro
    130                 135                 140

Leu Ser Leu Pro Val Ser Leu Gly Asp Gln Ala Ser Ile Ser Cys Arg
145                 150                 155                 160

Ser Ser Gln Ser Leu Val His Ser Asn Gly Lys Thr Tyr Leu His Trp
                165                 170                 175

Tyr Leu Gln Lys Pro Gly Gln Ser Pro Lys Leu Leu Ile Tyr Lys Val
            180                 185                 190

Ser Asn Arg Phe Ser Gly Val Pro Asp Arg Phe Ser Gly Ser Gly Ser
        195                 200                 205

Val Thr Asp Phe Thr Leu Met Ile Ser Arg Val Glu Ala Glu Asp Leu
    210                 215                 220

Gly Val Tyr Phe Cys Ser Gln Ser Thr His Val Pro Tyr Thr Phe Gly
225                 230                 235                 240

Gly Gly Thr Lys Leu Glu Ile Lys Asp Tyr Lys Asp Asp Asp Asp Lys
                245                 250                 255
```

<210> SEQ ID NO 103
<211> LENGTH: 256
<212> TYPE: PRT
<213> ORGANISM: Mus sp.
<220> FEATURE:
<223> OTHER INFORMATION: CF2LH-0/pCOS1. MABL2-scFv<LH-0>

<400> SEQUENCE: 103

```
Met Lys Leu Pro Val Arg Leu Leu Val Leu Met Phe Trp Ile Pro Gly
 1               5                  10                  15

Ser Ser Ser Asp Val Val Met Thr Gln Ser Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Lys Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80
```

```
                        -continued

Gly Val Pro Asp Arg Phe Ser Gly Ser Val Thr Asp Phe Thr
                85              90              95

Leu Met Ile Ser Arg Val Glu Ala Glu Asp Leu Gly Val Tyr Phe Cys
            100             105             110

Ser Gln Ser Thr His Val Pro Tyr Thr Phe Gly Gly Gly Thr Lys Leu
        115                 120                 125

Glu Ile Lys Gln Val Gln Leu Gln Gln Ser Gly Pro Glu Leu Val Lys
    130                 135                 140

Pro Gly Ala Ser Val Lys Met Ser Cys Lys Ala Ser Gly Tyr Thr Phe
145                 150                 155                 160

Ala Asn His Val Ile His Trp Val Lys Gln Lys Pro Gly Gln Gly Leu
                165                 170                 175

Glu Trp Ile Gly Tyr Ile Tyr Pro Tyr Asn Asp Gly Thr Lys Tyr Asn
            180                 185                 190

Glu Lys Phe Lys Asp Lys Ala Thr Leu Thr Ser Asp Lys Ser Ser Thr
        195                 200                 205

Thr Ala Tyr Met Asp Leu Ser Ser Leu Ala Ser Glu Asp Ser Ala Val
    210                 215                 220

Tyr Tyr Cys Ala Arg Gly Gly Tyr Tyr Thr Tyr Asp Asp Trp Gly Gln
225                 230                 235                 240

Gly Thr Thr Leu Thr Val Ser Ser Asp Tyr Lys Asp Asp Asp Lys
                245                 250                 255
```